(12) United States Patent
Brueggemeier et al.

(10) Patent No.: US 7,741,520 B2
(45) Date of Patent: Jun. 22, 2010

(54) SULFONANILIDE ANALOGS AS SELECTIVE AROMATASE MODULATORS (SAMS)

(75) Inventors: Robert W Brueggemeier, Dublin, OH (US); Bin Su, Columbus, OH (US); Edgar S Diaz-Cruz, Columbus, OH (US); Serena Landini, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 26 days.

(21) Appl. No.: 11/702,276

(22) Filed: Feb. 5, 2007

(65) Prior Publication Data

US 2008/0045598 A1 Feb. 21, 2008

Related U.S. Application Data

(60) Provisional application No. 60/764,993, filed on Feb. 3, 2006.

(51) Int. Cl.
C07C 311/10 (2006.01)
A61K 31/18 (2006.01)

(52) U.S. Cl. .............................. 564/99; 564/84; 564/97; 514/602; 514/605

(58) Field of Classification Search .................. None
See application file for complete search history.

(56) References Cited

FOREIGN PATENT DOCUMENTS

| DE | 4026544 A1 | 2/1991 |
|---|---|---|
| FR | 760212 A | 2/1934 |
| JP | 58024138 A | 2/1983 |
| JP | 02138168 A | 5/1990 |
| WO | WO 2007/120379 | 10/2007 |

OTHER PUBLICATIONS

Database CAPLUS on STN, Acc. No. 1970:43492, Jones et al., GB 1168105 (Oct. 22, 1969) (abstract).*
International Search Report and Written Opinion in PCT/US07/03152, dated Dec. 17, 2007 (20 pages).
Adams et al., "Quinone imides. XXIII. Addition reactions of p-quinonedibenzimide and related compounds," J. Am. Chem. Soc. (1952), vol. 74, pp. 5872-5876.
Berkade, et al., "Alkoxyaminonitrobenzenes. III. Nitration of 1-alkoxy-2-aminobenzenes and 1-alkoxy-2-acetamidobenzenes," Recueil des Travaux Chimiques de Pays-Bas et de la Belgique (1947), vol. 66, pp. 374-382.
Jacobson, P., "Behavior of ethers of o-oxyazo compounds on reduction with stannous chloride and hydrochloric acid," Ann. (1910), vol. 369, pp. 1-40.
Weigel, W., "Special substitution phenomena in the nitration of phenol ethers," J. de Physiologie (Paris, 1946-1992) (1956), vol. 4, pp. 79-88.
Su et al., "Novel sulfonanilide analogues suppress aromatase expression and activity in breast cancer cells independent of COX-2 inhibition," J. Med. Chem., 2006, 49, 1413-1419.

Su et al., "Synthesis and Biological Evaluation of Selective Aromatase Expression Regulators in Breast Cancer Cells," J. Med. Chem. 2007, 50, 1635-1644.
Su et al., "Suppression of aromatase in human breast cells by a cyclooxygenase-2 inhibitor and its analog involves multiple mechanisms independent of cyclooxygenase-2 inhibition," Steroids 73 (2008) 104-111.
Kellis, Jr. et al., "Purification and Characterization of Human Placental Aromatase Cytochrome P-450", J. Biological Chemistry, vol. 262, No. 9, Mar. 25, 1987, pp. 4413-4420.
Diaz-Cruz et al., "Cyclooxygenase Inhibitors Suppress Aromatase Expression and Activity in Breast Cancer Cells", J Clinical Endocrinology & Metabolism, 90(5) 2563-2570, 2005.
Baum et al. ATAC Trialists' Group, Anastrozole alone or in combination with tamoxifen versus tamoxifen alone for adjuvant treatment of postmenopausal women with early breast cancer: first results of the ATAC randomised trial. Lancet 2002, 359, 2131-2139.
Bergman, et al. Risk and prognosis of endometrial cancer after tamoxifen for breast cancer. Lancet 2000, 356, 881-887.
Brueggemeier, R. W.; Hackett, J. C.; Diaz-Cruz, E. S. "Aromatase inhibitors in the treatment of breast cancer" Endocr. ReV. 2005, 26, 331-345.

(Continued)

Primary Examiner—Brian J Davis
(74) Attorney, Agent, or Firm—Calfee, Halter & Griswold LLP

(57) ABSTRACT

Compounds and methods suppressing aromatase activity expression in cancer cells. Provided are compounds are those of formula I:

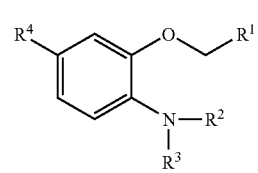

wherein $R^1$ may be alkyl, cycloalkyl, haloalkyl, aryl, substituted aryl, haloaryl, alkoxy, alkylaryl, and arylalkyl; $R^2$ is H, alkyl, aryl, alkylaryl, arylalkyl, and cycloalkyl; $R^3$, with the base nitrogen, forms an amide or sulfonamide; $R^4$ is selected from nitro, amine, amide, and benzamide; or a pharmaceutically acceptable salts thereof. Also provided are small molecule selective aromatase inhibitors having a molecular weight of less 500 g/mol. In some embodiments, the small molecule selective aromatase inhibitors described herein have a molecular weight of less than 450 g/mol. Also provided are methods for suppressing aromatase activity expression in cancer cells comprising the step of administering a pharmaceutically effective amount of a small molecule aromatase inhibitor to a subject in need of such treatment. In one embodiment, the cancer cells are breast cancer cells.

19 Claims, 16 Drawing Sheets

OTHER PUBLICATIONS

Chen, S. Aromatase and breast cancer. Frontiers Biosci. 1998, 3, 922-33.

Chen et al., Transcriptional regulation of aromatase expression in human breast tissue. J. Steroid Biochem. Mol. Biol. 2002, 83, 93-99.

Chen et al., Positive and negative transcriptional regulation of aromatase expression in human breast cancer tissue. J. Steroid Biochem. Mol. Biol. 2005, 95, 17-23.

Cignarella et al., Synthesis and pharmacological evaluation of derivatives structurally related to nimesulide. Eur. J. Med. Chem. 1996, 31, 359-364.

Hackett et al., Synthesis and characterization of azole isoflavone inhibitors of aromatase. Bioorg. Med. Chem. 2005, 13, 4063-4070.

Harada, N.; Honda, S. I.; Hatano, O. Aromatase inhibitors and enzyme stability. Endocr.-Rel. Cancer 1999, 6, 211-218.

Heshmati et al., Role of low levels of endogenous estrogen in regulation of bone resorption in late postmenopausal women. J. Bone Miner. Res. 2002, 17, 172-178.

Hiroya et al., New synthetic method for indole-2-carboxylate and its application to the total synthesis of duocarmycin SA. Org. Lett. 2004, 6, 2953-2956.

Julemont et al., Spectral and crystallographic study of pyridinic analogues of nimesulide: determination of the active form of methanesulfonamides as COX-2 selective inhibitors. J. Med. Chem. 2002, 45, 5182-5185.

Kinoshita et al., Induction of Aromatase (CYP19) Expression in Breast Cancer Cells through a Nongenomic Action of Estrogen Receptor alpha. Cancer Res. 2003, 63, 3546-3455.

Richards et al., Prostaglandin E2 regulates aromatase activity and expression in human adipose stromal cells via two distinct receptor subtypes. J. Clin. Endocrinol. Metab. 2003, 88, 2810-2816.

Simpson, E. R. Aromatase: biologic relevance of tissue-specific expression. Semin. Reprod. Med. 2004, 22, 11-23.

Smith, I. E.; Dowsett, M. Aromatase inhibitors in breast cancer. N. Engl. J. Med. 2003, 348, 2431-2442.

Zhao et al., Characterization of the sequences of the human CYP19 (aromatase) gene that mediate regulation by glucocorticoids in adipose stromal cells and fetal hepatocytes. Mol. Endocrinol. 1995, 9, 340-349.

Zhao et al., Estrogen biosynthesis proximal to a breast tumor is stimulated by PGE2 via cyclic AMP, leading to activation of promoter II of the CYP19 (aromatase) gene. Endocrinology 1996, 137, 5739-5742.

Zhou et al., Aromatase gene expression and its exon I usage in human breast tumors. Detection of aromatase messenger RNA by reverse transcription-polymerase chain reaction (RT-PCR). J. Steroid Biochem. Mol. Biol. 1996, 59, 163-171.

Zhou et al., Identification of a promoter that controls aromatase expression in human breast cancer and adipose stromal cells. J. Biol. Chem. 1996, 271, 15191-15202.

Zhou et al., Gene regulation studies of aromatase expression in breast cancer and adipose stromal cells. J. Steroid Biochem. Mol. Biol. 1997, 61, 273-280.

American Cancer Society, Cancer Facts and Figures, 2005, American Cancer Society, Atlanta, 2005 , p. 1-28.

Natarajan, et al., "Adaptation of the diphenylamine (DPA) assay to a 96-well plate tissue culture format and comparison with the MTT assay", Biotechniques, 1994, 17, 166-171.

* cited by examiner

SULFONANILIDE ANALOGS AS SELECTIVE AROMATASE MODULATORS (SAMS)

CROSS-REFERENCE TO RELATED APPLICATIONS

This application claims priority to, and any benefit of, U.S. Provisional Patent Application Ser. No. 60/764,993, filed Feb. 3, 2006, the entirety of which is incorporated herein by reference.

STATEMENT ON FEDERALLY FUNDED RESEARCH

This invention was funded at least in part by National Institutes of Health Grant No. R01 CA073698. The federal government may have certain rights in this invention.

BACKGROUND OF THE INVENTION

In the United States, breast cancer is the most common cancer diagnosed in women and is the second leading cause of death in women after lung cancer. It is estimated that 212,920 new cases of invasive breast cancer will be detected among women in the United States in the 2006 and 40,970 women will die from this disease in the same year. Approximately 60% of premenopausal and 75% of postmenopausal breast cancer patients have estrogen-dependent carcinoma. Hormone-dependent breast tumors require estrogens for their growth and are characterized by high expression of estrogen receptors (ERs). As a result, efforts to block estrogen action by interfering with the binding to its receptor or by decreasing estrogen production are used as strategies to treat hormone-dependent breast cancer. The first approach involves antiestrogen molecules that can compete with estrogen for binding to the ERs. The second method utilizes aromatase inhibitors (AIs) that inhibit the enzyme catalyzing the final rate-limiting step of the estrogen biosynthesis.

Significant research has focused on developing antiestrogens that can selectively inhibit the estrogen effects in breast tissue without antagonizing the physiological roles of estrogens in other tissues. Agents that exhibit such tissue-specific antiestrogenic/estrogenic activities have been termed selective estrogen receptor modulators (SERMs). Tamoxifen is the most widely used SERM in hormone-dependent breast cancer therapy and has made a substantial contribution to the reduced mortality rate in many developed countries since 1990. Although tamoxifen is still considered the "gold standard" for endocrine therapy in hormone-dependent breast cancer, its use is associated with tumor resistance and increased risk of endometrial cancer. Aromatase inhibitors, such as anastrozole, letrozole, and exemestane, significantly decrease plasma estrogen levels, are emerging as alternatives to tamoxifen due to their clinical efficacy, and have favorable safety profiles for the treatment of hormone-dependent breast cancer in postmenopausal women. However, since the AIs inhibit aromatase enzyme in a global fashion, a major long term side effect of the AIs is the reduction of the bone density which can lead to osteoporosis.

To reduce the risk of the long term side effects, a new pharmacological approach in the treatment of estrogen dependent postmenopausal breast cancer is the use of tissue-specific inhibitors of aromatase. This concept is based on the tissue-specific regulation of aromatase expression. Ten different promoter regions have been identified upstream of the coding region of the aromatase gene (CYP19). The employment of alternative promoters results in tissue specific regulation of the CYP19 expression. Each promoter is regulated by distinct hormones and second messenger pathways. In postmenopausal women, estrogens are produced by adipose tissue, including breast tissue and skin. In these tissues aromatase expression is directed by promoter 1.4 that is regulated by the synergistic actions of glucocorticoids and class I cytokines such interleukin (IL)-6, IL-11 and tumor necrosis factor alpha (TNFα). In breast adenocarcinoma, aromatase expression and activity increase significantly compare to normal breast tissue. Breast tumors produce factors that stimulate aromatase expression locally. This stimulation is associated with switching of aromatase gene promoter from promoter I.4 to c-AMP dependent promoter I.3 and promoter II in breast cancer and surrounding adipose stromal cells. Current evidences suggest that tumor-derived factors, including the cyclooxygenase (COX) product prostaglandin $E_2$ ($PGE_2$), can mediate the induction of aromatase expression via promoter II by stimulating adenylate cyclase in adipose stromal cells. This biochemical mechanism may explain epidemiological observations of the beneficial effect of nonsteroidal anti-inflammatory drugs (NSAIDs) on breast cancer.

There exists a need for new compounds for treating breast cancers and other cancers as well as new synthetic approaches to making such compounds.

SUMMARY OF THE INVENTION

Compounds and methods for suppressing aromatase activity expression in cancer cells. The compounds are those of formula I:

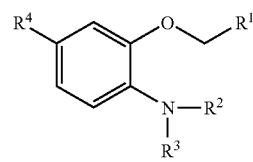

wherein $R^1$ may be alkyl, cycloakyl, haloalkyl, aryl, substituted aryl, haloaryl, alkoxy, alkylaryl, and arylalkyl; $R^2$ is H, alkyl, aryl, alkylaryl, arylalkyl, and cycloalkyl; $R^3$, with the base nitrogen, forms an amide or sulfonamide; $R^4$ is selected from nitro, amine, amide, and benzamide; or a pharmaceutically acceptable salts thereof. The compounds of formula I may be substituted at any substitutable position with one or more functional groups selected from the group consisting of alkyl, aryl, halo, alkylaryl, arylalkyl, and combinations thereof.

Also provided are small molecule selective aromatase inhibitors having a molecular weight of less 500 g/mol. In some embodiments, the small molecule selective aromatase inhibitors described herein have a molecular weight of less than 450 g/mol.

Also provided are methods for suppressing aromatase activity expression in cancer cells comprising the step of administering a pharmaceutically effective amount of a small molecule aromatase inhibitor to a subject in need of such treatment. In one embodiment, the cancer cells are breast cancer cells.

BRIEF DESCRIPTION OF THE DRAWINGS

FIG. 7 shows synthetic scheme 3, preparation of compounds 5a-15a.

DETAILED DESCRIPTION OF THE INVENTION

Figure 1:
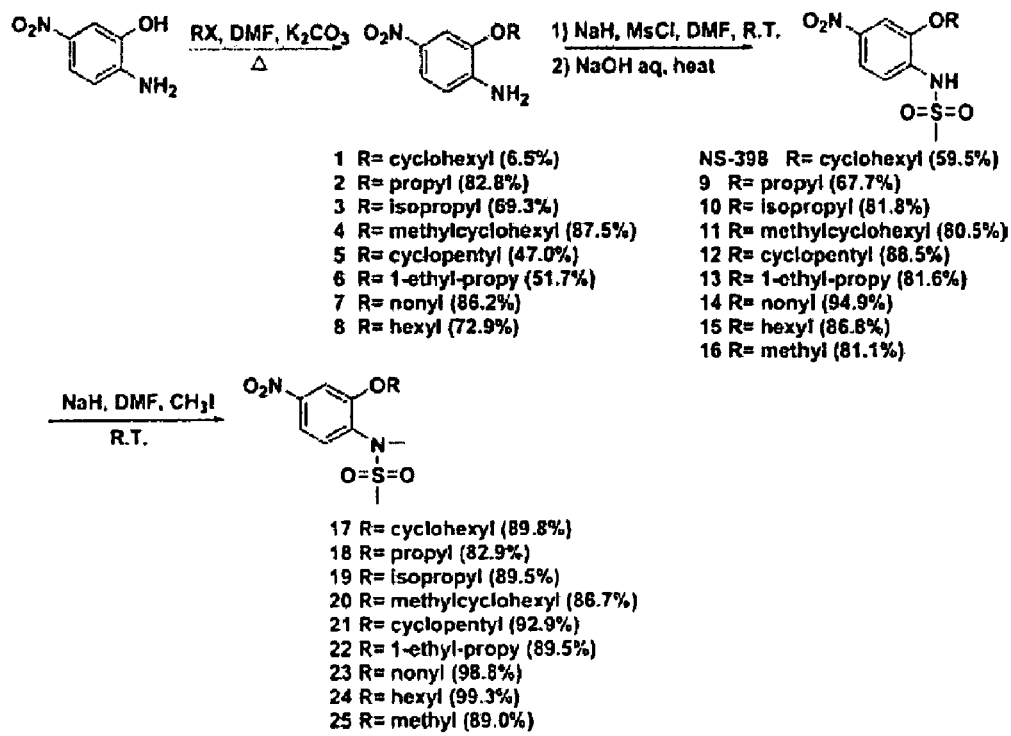
FIG. 1 shows the synthetic scheme for several sulfonalide analogues.

Research in our laboratory demonstrates that the COX-2 selective inhibitor NS-398 is significantly stronger in suppression of aromatase activity than other COX-2 inhibitors in breast cancer cells. Described herein is the synthesis of a small library of novel sulfonanilide analogues and their biological activity on aromatase and COX-2 in breast cancer cells.

Synthetic approaches were used to produce a novel series of sulfonanilide compounds. The effect of these compounds on aromatase and COX-2 inhibition were investigated in breast cancer cells. Structure activity analysis did not show a correlation between aromatase suppression and COX-2 inhibition. Time course studies show that the novel sulfonanilide analogs suppress aromatase activity in a prolonged reversible manner. Microsomal aromatase inhibition studies illustrate that the supression is not due to direct enzyme inhibition. Real-time PCR analysis of aromatase gene expression proves that novel sulfonanilide analogs do not decrease mRNA levels at concentrations near the $IC_{50}$ value for enzyme suppression in SK-BR-3 cells. All of these results suggest that novel sulfonanilide analogs suppress aromatase with a post-transcriptional mechanism in a COX-2 independent manner.

Aromatase is a particularly attractive target in the treatment of estrogen receptor positive breast cancer. Aromatase levels in breast cancer cells are enhanced by prostaglandins and reduced by COX inhibitors. The synthesis and biological evaluation of a novel series of sulfonanilide analogues derived from the COX-2 selective inhibitor NS-398 are described. The compounds suppress aromatase enzyme activity in SK-BR-3 breast cancer cells in a dose- and time-dependent manner. The effect of these compounds on COX-2 inhibition is investigated in breast cancer cells as well. Structure-activity analysis does not find a correlation between aromatase suppression and COX-2 inhibition. Microsomal aromatase inhibition studies rule out the possibility of direct enzyme inhibition. Real-time PCR analysis demonstrates that the sulfonanilide analogues decrease aromatase gene transcription in SK-BR-3 cells. These studies suggest that the novel sulfonanilide compounds suppress aromatase activity and transcription in SK-BR-3 breast cancer cells independent of COX-2 inhibition.

By "treating" is meant curing, ameliorating or tempering the severity of the cancer or the symptoms associated there-with. The terms "treating," "treatment," and "therapy" as used herein refer to curative therapy, prophylactic therapy, and preventative therapy.

"Preventing" or "prevention" means preventing the occurrence of the cancer, or tempering the severity of the cancer if it is develops subsequent to the administration of the instant compositions. This preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those at risk of developing precancers and cancers.

The terms "therapeutically effective" and "pharmacologically effective" are intended to qualify the amount of each agent which will achieve the goal of improvement in disease severity and the frequency of incidence over treatment of each agent by itself, while avoiding adverse side effects typically associated with alternative therapies.

The term "subject" for purposes of treatment includes any human or animal subject having a neoplasia, such as cancer or precancer. For methods of prevention the subject is any human or animal subject, and preferably is a human subject who is at risk of developing a cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

The term "derivative" is intended to encompass compounds which are structurally related to the present invention or which possess the substantially equivalent activity to the parent compound, as measured by the derivative's ability to inhibit activity in an in vitro cell proliferation assay using human breast cells, for example. By way of example, such compounds may include, but are not limited to, esters, metabolic products, and prodrugs thereof. Such compounds can be formed in vivo, such as by metabolic mechanisms.

Where the term alkyl is used, either alone or with other terms, such as haloalkyl or alkylaryl, it includes $C_1$ to $C_{10}$ linear or branched alkyl radicals, examples include methyl, ethyl, propyl, isopropyl, butyl, tert-butyl, and so forth. The term "haloalkyl" includes $C_1$ to $C_{10}$ linear or branched alkyl radicals substituted with one or more halo radicals. Some examples of haloalkyl radicals include trifluoromethyl, 1,2-dichloroethyl, 3-bromopropyl, and so forth. The term "halo" includes radicals selected from F, Cl, Br, and I.

The term aryl, used alone or in combination with other terms such as alkylaryl, haloaryl, or haloalkylaryl, includes such aromatic radicals as phenyl, biphenyl, and benzyl, as well as fused aryl radicals such as naphthyl, anthryl, phenanthrenyl, fluorenyl, and indenyl on so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. "Alkylaryl" or "arylalkyl" refers to alkyl-substituted aryl groups such as butylphenyl, propylphenyl, ethylphenyl, methylphenyl, 3,5-dimethylphenyl, tert-butylphenyl and so forth.

The agents of the present invention may be administered orally, intravenously, intranasally, rectally, or by any means which delivers an effective amount of the active agent to the tissue or site to be treated. It will be appreciated that different dosages may be required for treating different disorders. An effective amount of an agent is that amount which causes a statistically significant decrease in neoplastic cell count, growth, or size. Neoplastic disorders responsive to the agents of the present invention include, but are not limited to, breast cancer.

The dosage form and amount can be readily established by reference to known treatment or prophylactic regiments. The amount of therapeutically active compound that is administered and the dosage regimen for treating a disease condition with the compounds and/or compositions of this invention depends on a variety of factors, including the age, weight, sex, and medical condition of the subject, the severity of the disease, the route and frequency of administration, the particular compound employed, the location of the unwanted proliferating cells, as well as the pharmacokinetic properties of the individual treated, and thus may vary widely. The dosage will generally be lower if the compounds are administered locally rather than systemically, and for prevention rather than for treatment. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

The active agents may be administered along with a pharmaceutical carrier and/or diluent. The agents of the present invention may also be administered in combination with other agents, for example, in association with other chemotherapeutic or immunostimulating drugs or therapeutic agents. Examples of pharmaceutical carriers or diluents useful in the present invention include any physiological buffered medium, i.e., about pH 7.0 to 7.4 comprising a suitable water soluble organic carrier. Suitable water soluble organic carriers include, but are not limited to corn oil, dimethylsulfoxide, gelatin capsules, etc.

Also included in the family of sulfonanilide compounds are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable.

Suitable pharmaceutically acceptable acid addition salts of sulfonanilide compounds may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids.

Suitable pharmaceutically acceptable base addition salts of sulfonanilide compounds include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the sulfonanilide compounds. All of these salts may be prepared by conventional means from the corresponding sulfonanilide compounds by reacting, for example, the appropriate acid or base with the sulfonanilide compound.

The phrase "adjunct therapy" (or "combination therapy"), in defining use of a compound of the present invention and one or more other pharmaceutical agent, is intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations for each agent.

There are large numbers of antineoplastic agents available in commercial use, in clinical evaluation and in pre-clinical development, which could be selected for treatment of cancers or other neoplasias by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents. Alternatively, other anti-neoplastic agents, such as metallomatrix proteases inhibitors may be used. Suitable agents which may be used in combination therapy will be recognized by those of skill in the art.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

In one embodiment, the compound is that of formula I:

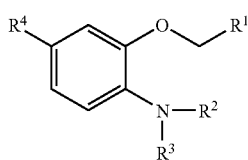

I wherein $R^1$ is selected from the group consisting of alkyl, including straight-chain alkyl, branched alkyl, cycloakyl, and haloalkyl, aryl, substituted aryl, haloaryl, alkoxy, alkylaryl, arylalkyl, and combinations thereof. In some embodiments, $R^1$ is selected from the group consisting of $C_1$ to $C_{10}$ alkyl, cyclopentyl, cyclohexyl, methylcyclohexyl, benzyl, nitrobenzyl, alkylbenzyl, dialkylbenzyl, alkoxybenzyl, halobenzyl, phenylalkyl, phenylbenzyl, phenylbenzyloxy, naphthyl, and naphthylmethyl. In some embodiments, $R^1$ is selected from the group consisting of methyl, ethyl, propyl, isopropyl, butyl, pentyl, hexyl, heptyl, octyl, nonyl, decyl, cyclopentyl, cyclohexyl, methylcyclohexyl, ethylcyclohexyl, 1-methoxypropyl, and 1-ethoxypropyl. In some embodiments, $R^1$ is selected from nitrobenzyl, phenylbenzyl, naphthyl, naphthylmethyl, methoxybenzyl, isopropylbenzyl, fluorobenzyl, chlorobenzyl, bromobenzyl, dimethylbenzyl, and phenylethyl. In some embodiments, $R^1$ is selected from 4-nitrobenzyl, 2-phenylbenzyl, naphthyl, α-naphthylmethyl, β-naphthylmethyl, 4-methoxybenzyl, 4-isopropylbenzyl, 4-fluorobenzyl, 4-chlorobenzyl, 4-bromobenzyl, 3,6-dimethylbenzyl, and phenylethyl. In some embodiments, $R^1$ is further substituted with one or more functional groups; some exemplary functional groups include, but are not limited to, alkyl, aryl, halo, alkylaryl, arylalkyl, and combinations thereof. In one exemplary embodiment, $R^1$ is a larger aryl functionality. In another exemplary embodiment, $R^1$ is phenylbenzyl; in another exemplary embodiment, $R^1$ is naphthylmethyl. In some embodiments, $R^1$ is further substituted with one or more functional groups selected from the group consisting of alkyl, aryl, halo, alkylaryl, arylalkyl, and combinations thereof.

$R^2$ is selected from the group consisting of H, $C_1$ to $C_{10}$ alkyl, aryl, alkylaryl, arylalkyl, and cycloalkyl, wherein $R^2$ may be further substituted with one or more suitable functional group such as alkyl, aryl, halo, alkylaryl, arylalkyl, and combinations thereof. In one exemplary embodiment, $R^2$ is selected from $C_1$ to $C_{10}$ alkyl, wherein the alkyl group may be straight chain, branched, or cyclic, or a combination thereof. In some embodiments, $R^2$ may be H, methyl ethyl, n-propyl, isopropyl, pentyl, hexyl or cyclohexyl. In another exemplary embodiment, $R^2$ is methyl. In another exemplary embodiment, $R^2$ is selected from the group consisting of alkylaryl, benzyl, alkoxybenzyl, alkylbenzyl, halobenzyl, biphenyl, and naphthyl. In another exemplary embodiment, $R^2$ is selected from the group consisting of benzyl, methoxybenzyl, methylbenzyl, fluorobenzyl, chlorobenzyl, bromobenzyl, isopropylbenzyl, dimethylbenzyl, phenylbenzyl, and naphthyl. In another exemplary embodiment, $R^2$ is selected from the group consisting of benzyl, 4-methoxybenzyl, 4-methylbenzyl, 4-fluorobenzyl, 4-chlorobenzyl, 4-bromobenzyl, 4-isopropylbenzyl, 2,5-dimethylbenzyl, 4-phenylbenzyl, and 2-naphthyl. In another exemplary embodiment, $R^2$ is methyl.

Modifications of $R^2$

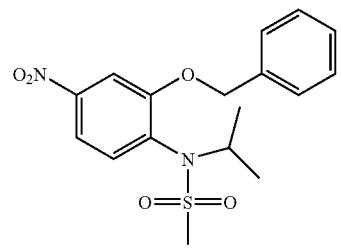

-continued
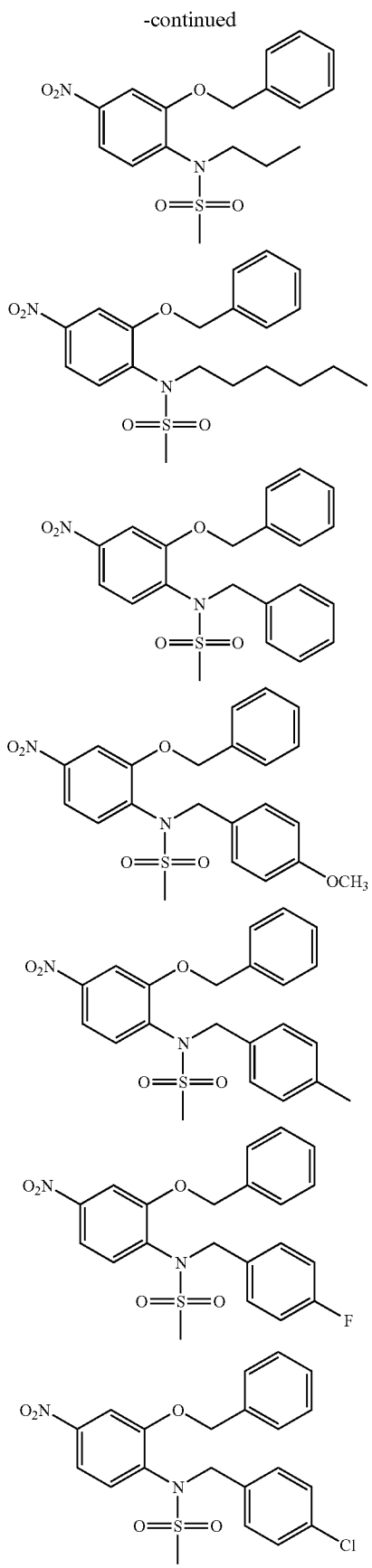
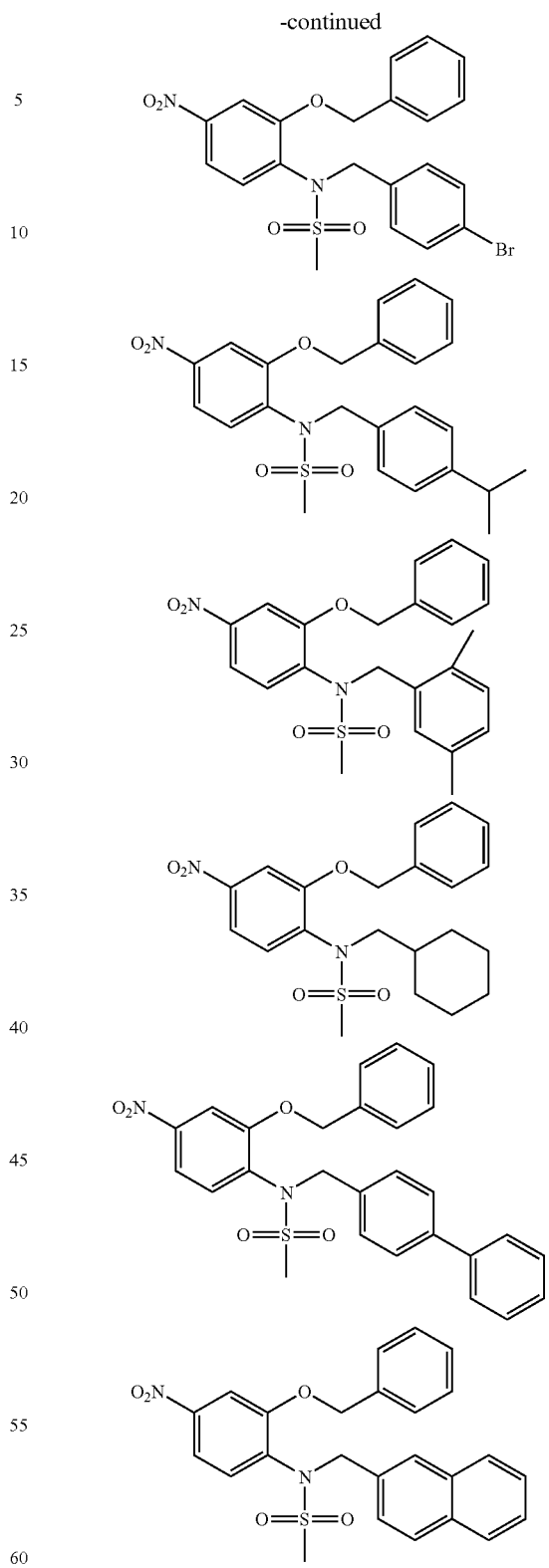
$R^3$, with the N base, forms an amide or a sulfonamide. In some exemplary embodiments, $R^3$, with the base N, is selected from the group consisting of methylamide, ethylamide, propylamide, butylamide, pentylamide, hexylamide, heptylamide, octylamide, nonylamide, cyclopentylamide, and cyclohexylamide; and combinations thereof. In some exemplary embodiment, $R^3$, with the base N, is selected from phenylamido, nitrophenylamido, haloamido, cyanoamido, naphthylamido, biphenylamido, and alkylphenylamido; and combinations thereof. In some additional exemplary embodiments, $R^3$, with the base N, is selected from the group consisting of 4-nitrophenylamido, 3-nitrophenylamido, 2-nitro-3-chloroamido, 3,4-dichloroamido, 4-cyanoamido, 2-naphthylamido, biphenylamido; or a pharmaceutically acceptable salt thereof.

Modifications of $R^3$

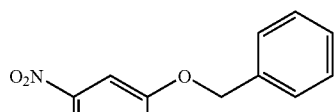

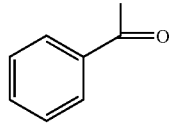

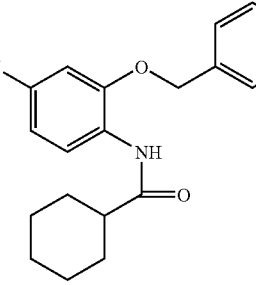

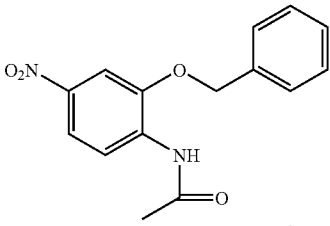

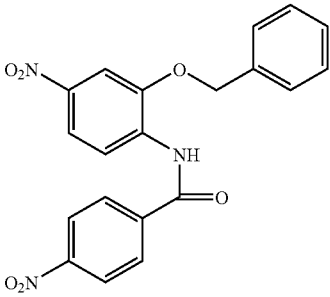

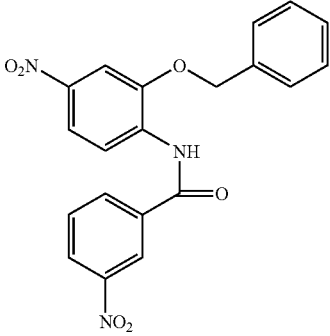

-continued

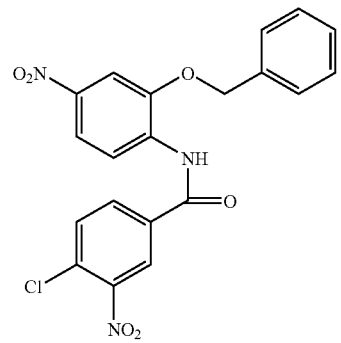

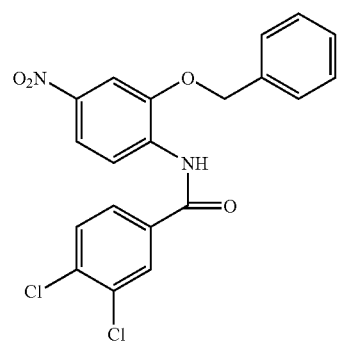

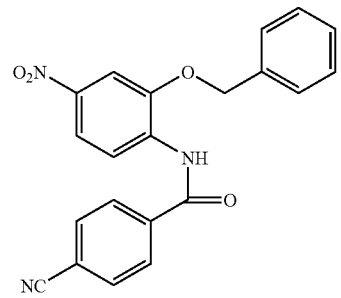

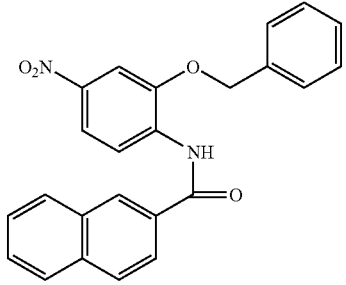

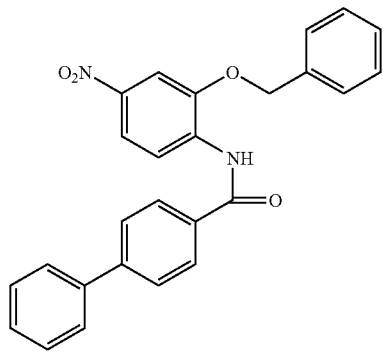

-continued

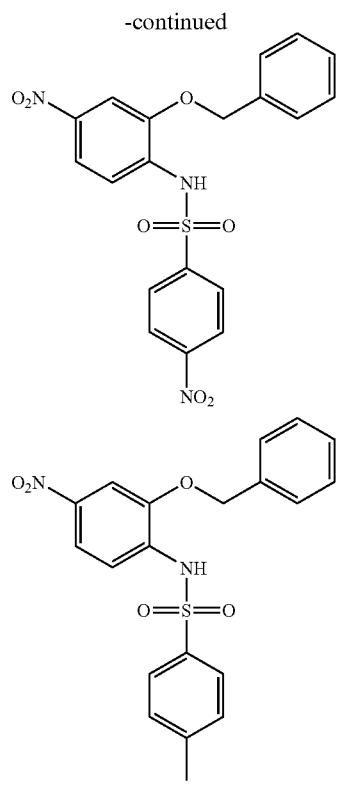

R[4] is selected from the group consisting of nitro, amine, amide, and benzamide. In an exemplary embodiment, R[4] is benzamide. In other exemplary embodiments, R[4] is selected from cyanobenzamide, halobenzamide, dihalobenzamide, nitrobenzamide. In further exemplary embodiments, R[4] is selected from 4-cyanobenzamide, 3,4-dichlorobenzamide, and 3-nitrobenzamide. In another exemplary embodiment, R[4] is naphthylamide. In another exemplary embodiment, R[4] is 2-naphthylamide. In another exemplary embodiment, R[4] is an alkylamide. In another embodiment, R[4] is a cyclohexylamide. In any of these embodiments, R[4] may be substituted at any substitutable position with one or more substituents such as alkyl, aryl, halo, nitro, cyano and so forth.

Modifications of R[4]

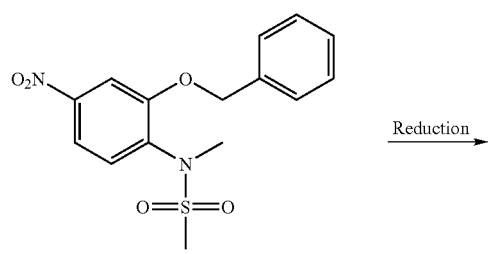

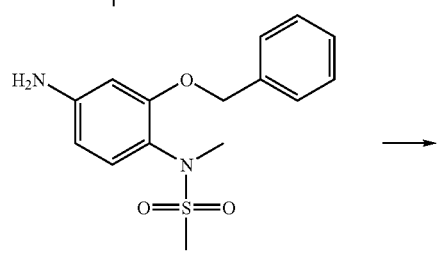

-continued

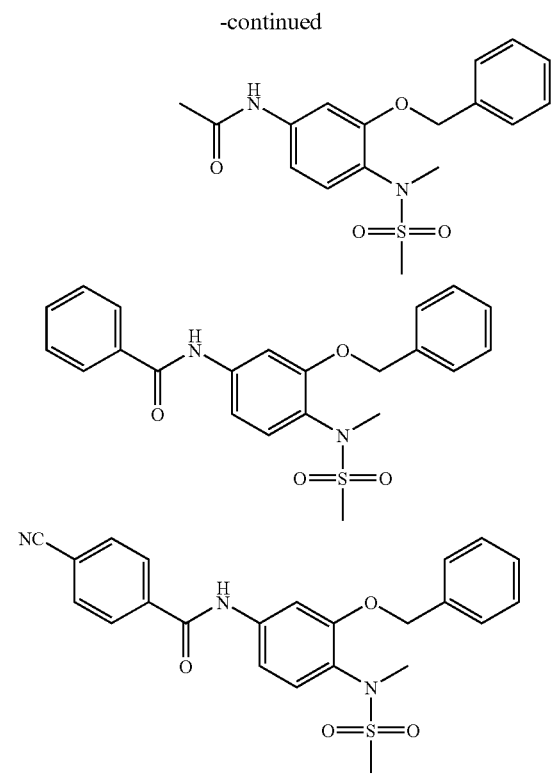

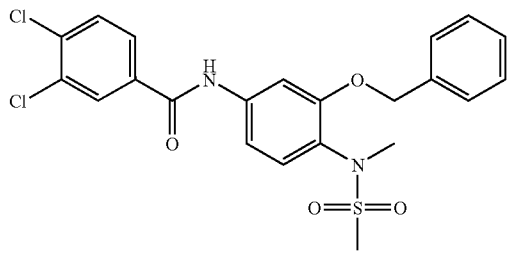

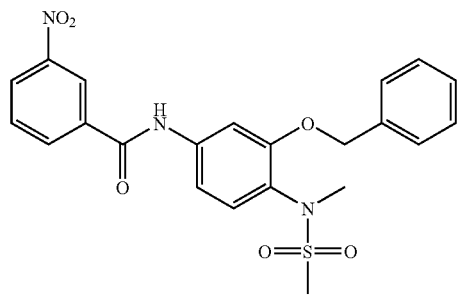

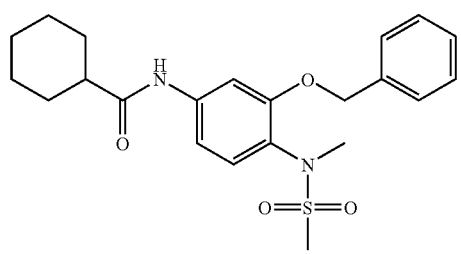

-continued

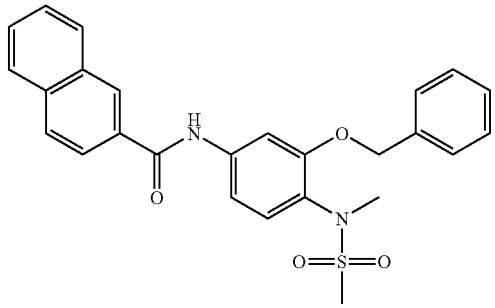

One exemplary embodiment is that of formula II:

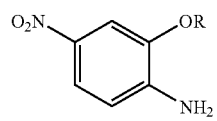

II wherein R is selected from the group consisting of straight-chained alkyl, branched alkyl, cycloalkyl, alkoxy, aryl, substituted aryl, alkylaryl, arylalkyl, haloaryl, and combinations thereof, wherein R may be further substituted with alkyl, aryl, and halo groups, and derivatives thereof. In another exemplary embodiment, the compound is that of formula III:

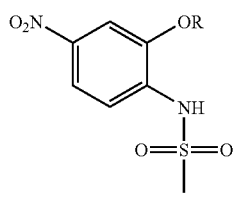

III wherein R is selected from the group consisting of straight-chained alkyl, branched alkyl, cycloalkyl, alkoxy, aryl, substituted aryl, alkylaryl, arylalkyl, haloaryl, and combinations thereof, wherein R may be further substituted with alkyl, aryl, and halo groups, and derivatives thereof. In another exemplary embodiment, the compound is that of formula IV:

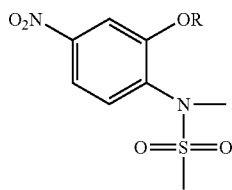

Figure 6:
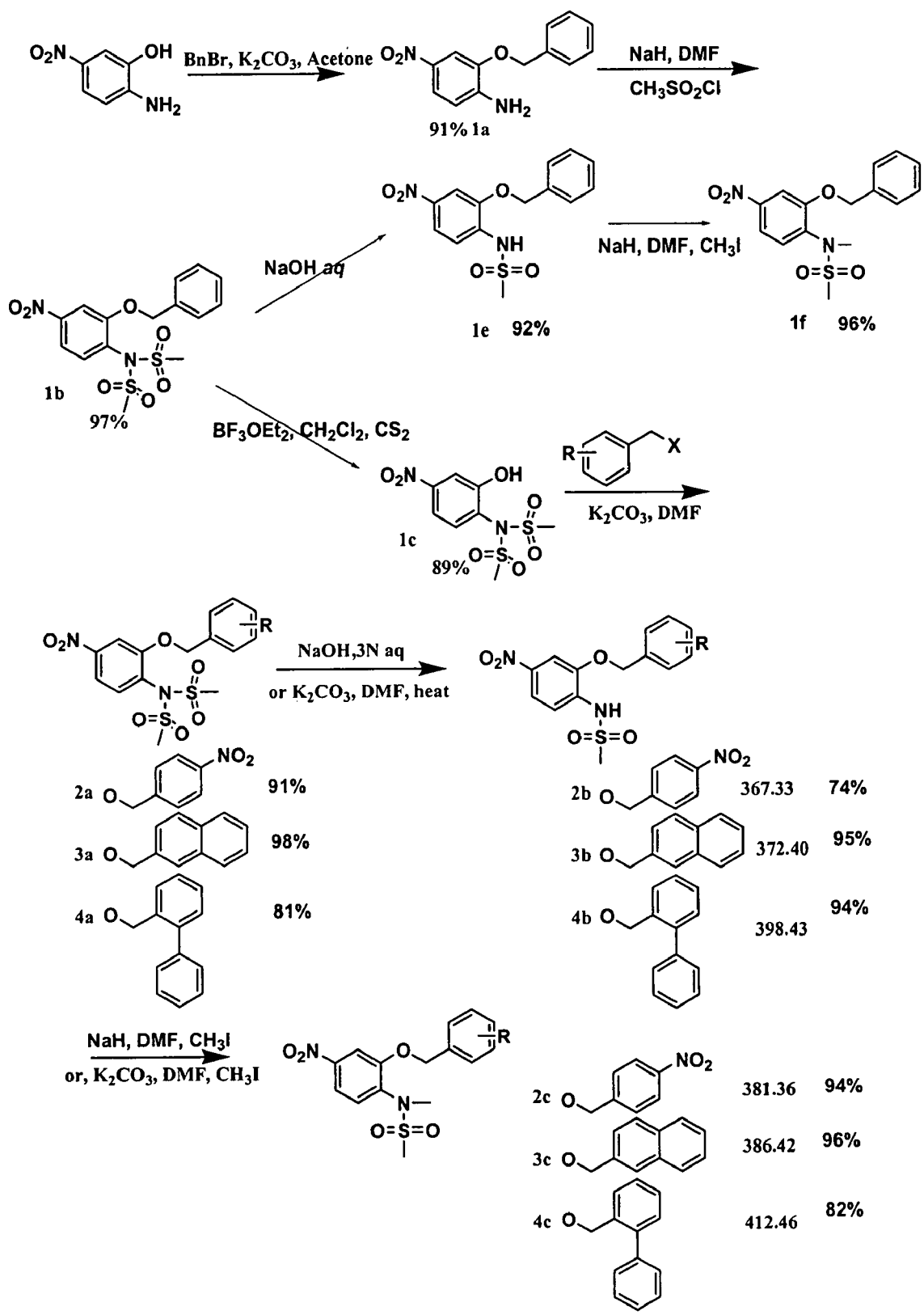
FIG. 6 shows synthetic scheme 2, preparation of compounds 1a-4c.
Figure 7:
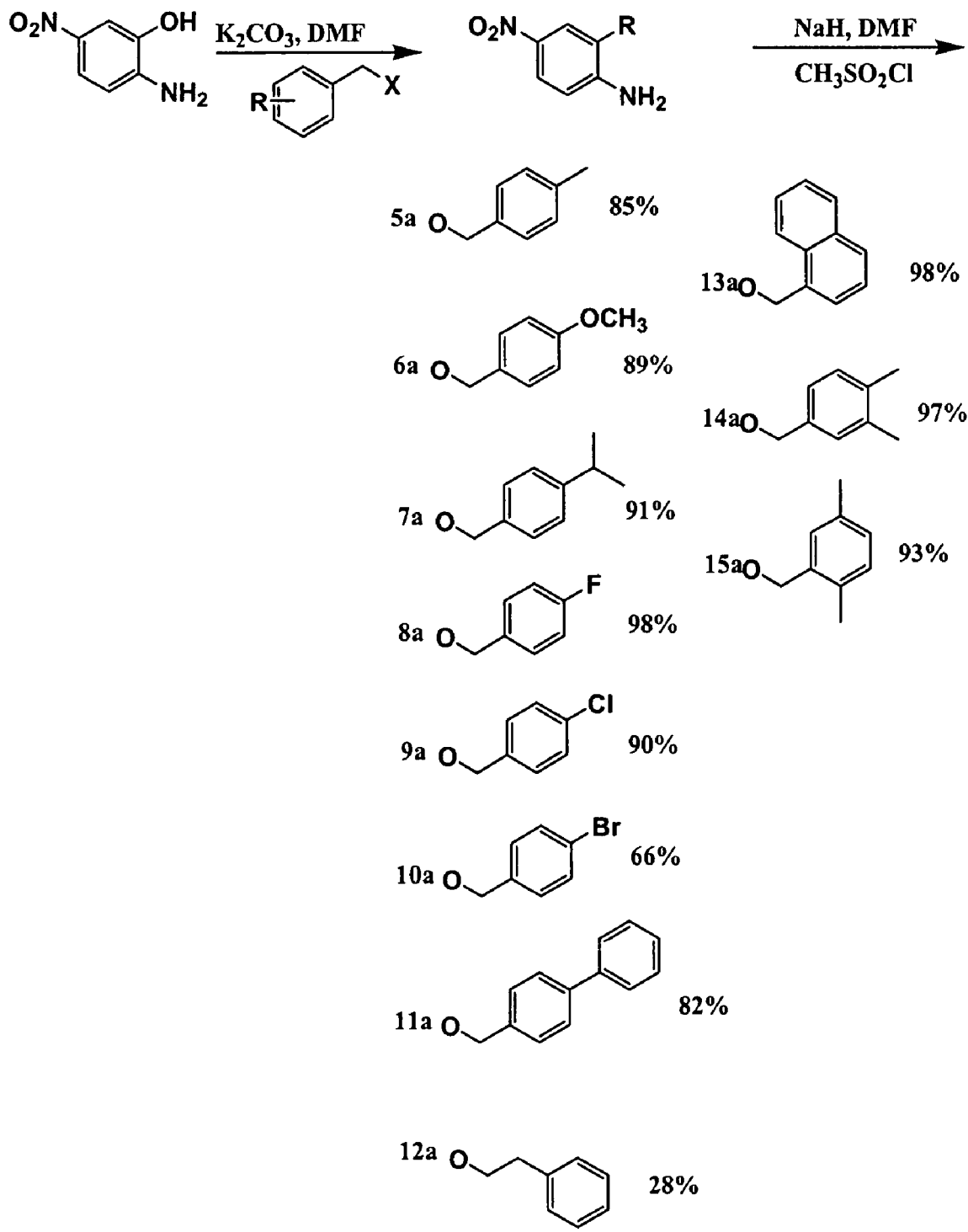
Figure 8:
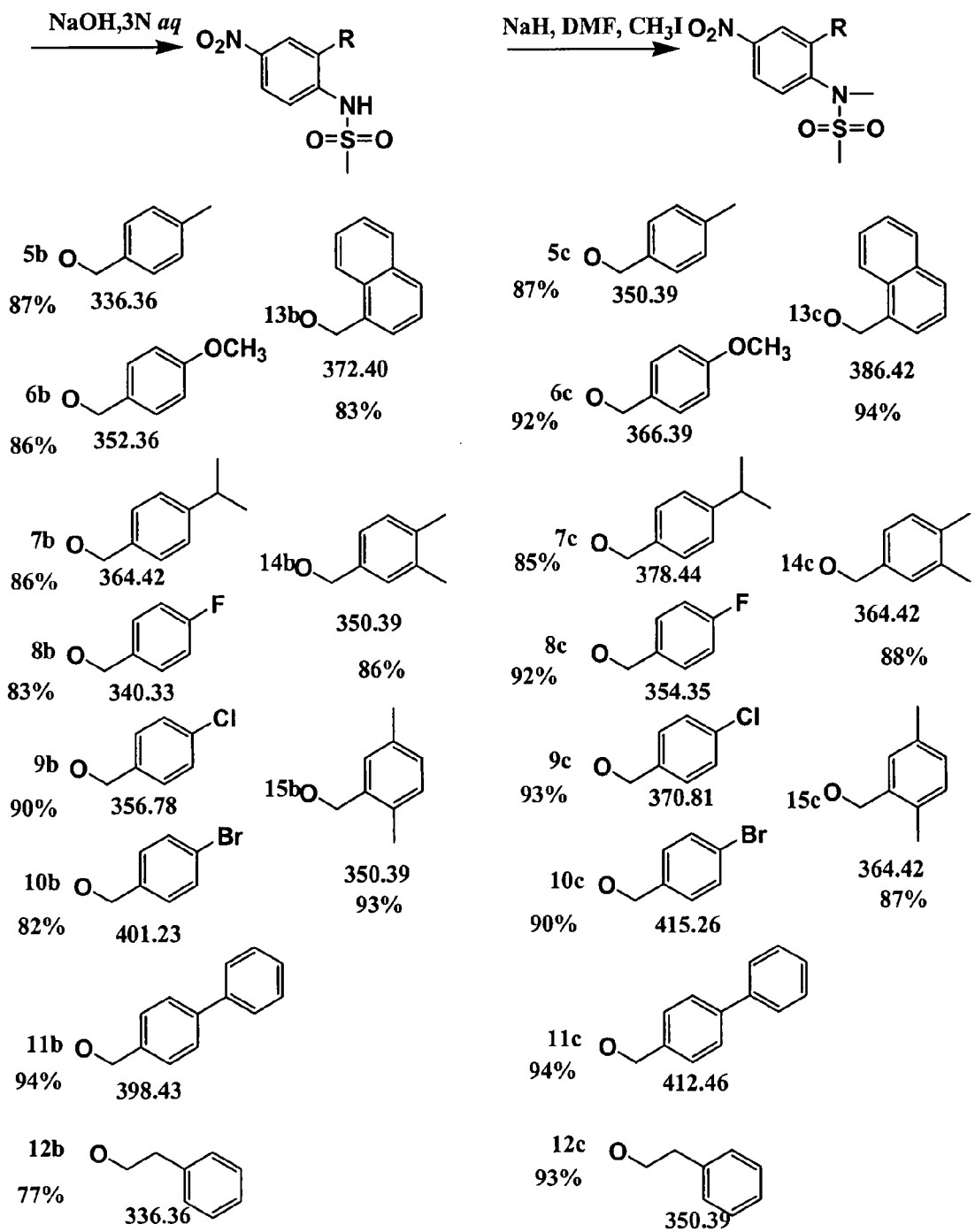
FIG. 8 shows preparation of compounds 5b-15c.
Figure 9:
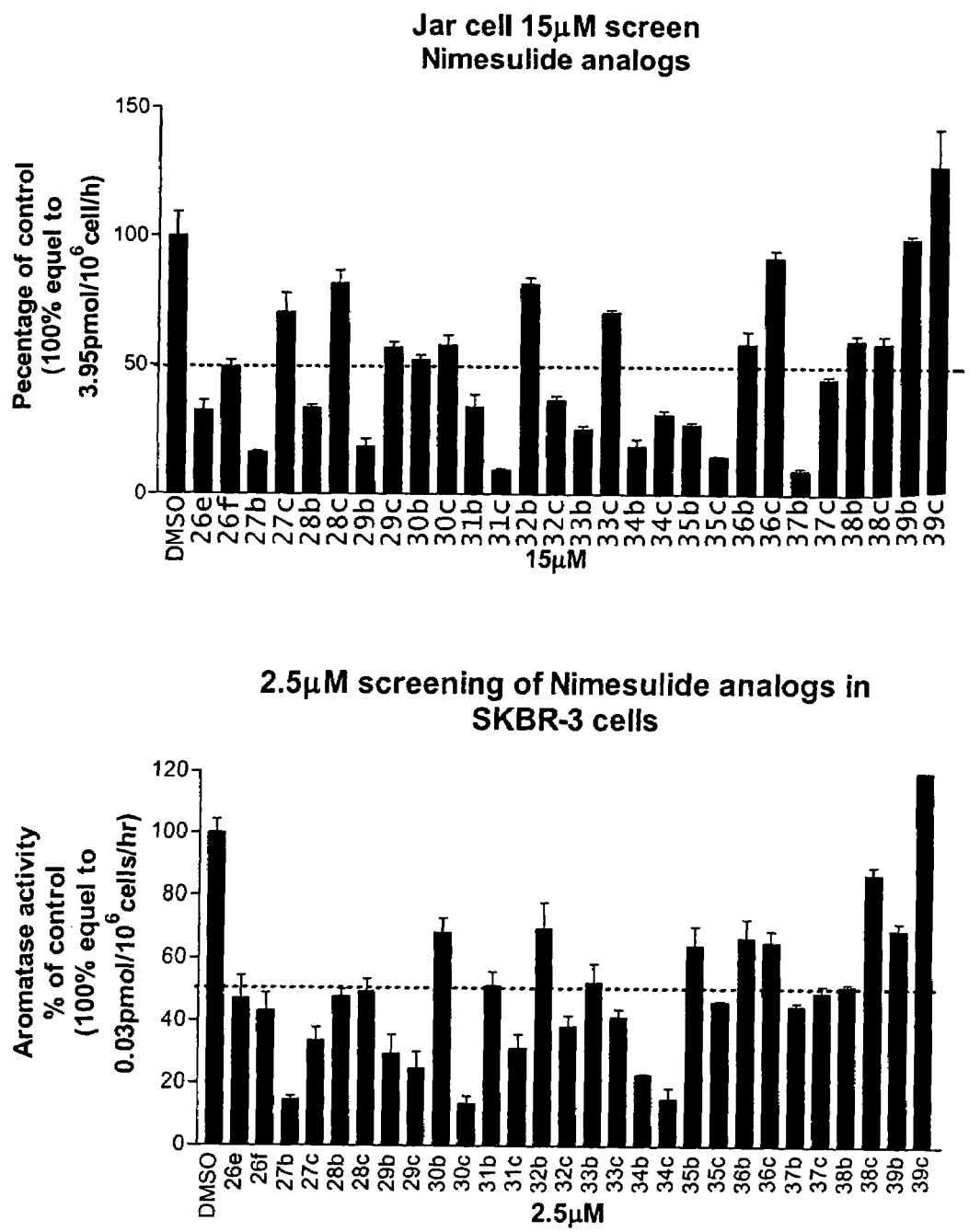
FIG. 9 shows aromatase activity in Jar cells and SK-BR-3 cells.
Figure 10:
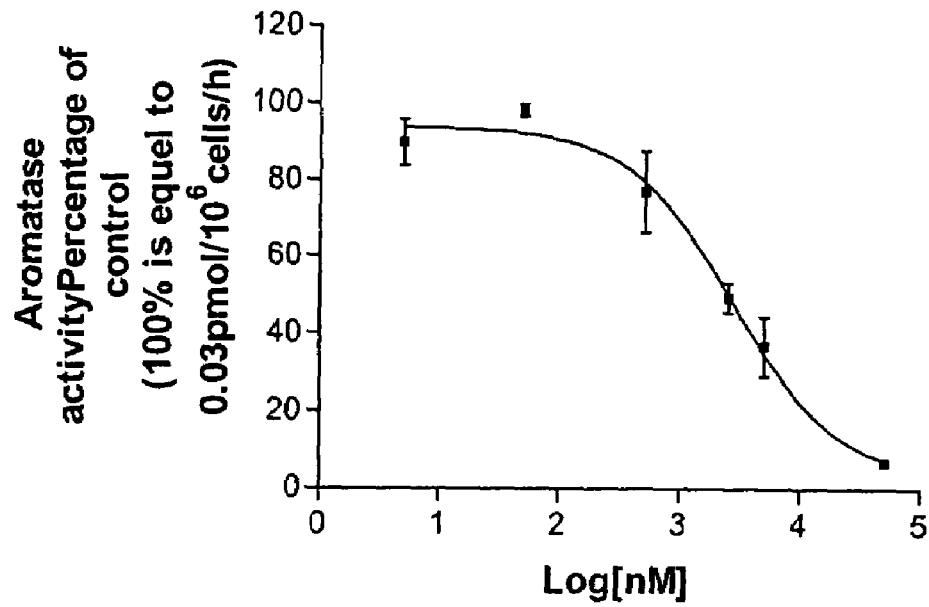
FIG. 10 shows the $IC_{50}$ of compounds 3c and 1f, respectively. $IC_{50}$ of 1f and 2C are 6.65 µM and 2.66 µM respectively
Figure 10:
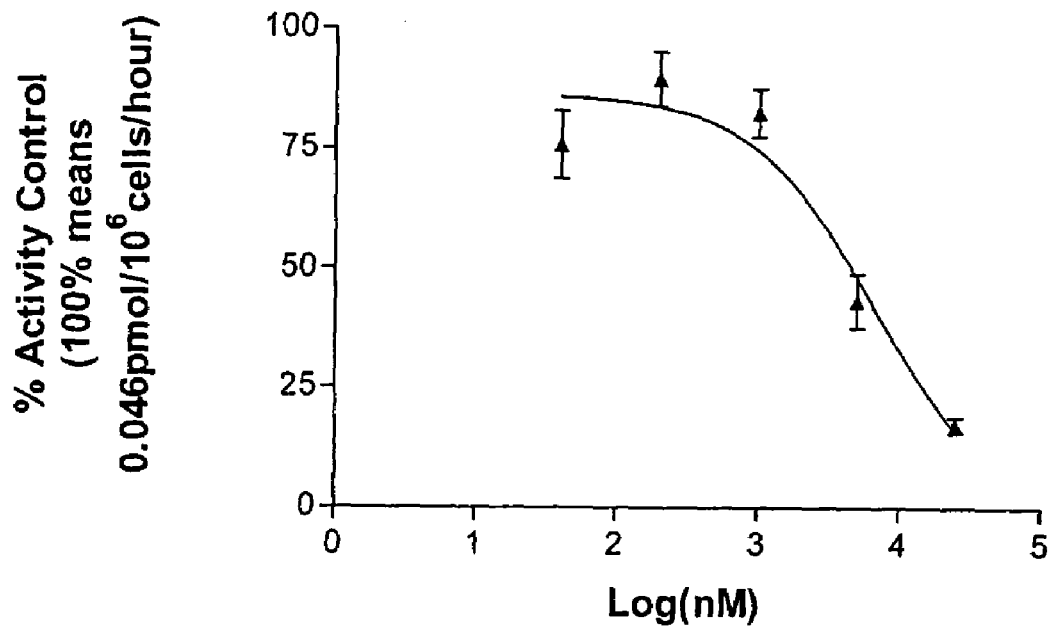

IV wherein R is selected from the group consisting of straight-chained alkyl, branched alkyl, cycloalkyl, alkoxy, aryl, substituted aryl, alkylaryl, arylalkyl, haloaryl, and combinations thereof, wherein R may be further substituted with alkyl, aryl, and halo groups, and derivatives thereof. In still other embodiments, the compounds are those shown in FIG. 6-8, and derivatives and prodrugs thereof.

Unique to the compounds provided herein, the small molecules of formula I may be used effective to regulate aromatase activity expression in cancer cells. In non-brominated embodiments, the compounds of formula I may weigh less than 450 g/mol. In brominated embodiments, the compounds of formula I may weigh less than 500 g/mol.

Further provided are methods for using the compounds of formula I for suppressing aromatase activity expression in cancer cells. According to the method provided herein, a pharmaceutically effective amount of an aromatase inhibitor formula I is administered to a subject in need of such treatment. In some embodiments, the cancer cells are breast cancer cells.

Drug Design. Previously we studied different COX-2 inhibitors with similar $IC_{50}$ values (concentration for 50% inhibition) for COX-2 inhibition differ significantly in their ability to suppress aromatase activity. This observation suggests differences in the mechanisms by which these COX inhibitors modulate aromatase expression in SK-BR-3 cells. To determine whether the modulation of aromatase expression by COX-2 inhibitors required the inhibition of COX-2 enzyme activity, we designed and synthesized several analogues with no COX-2 inhibitory activity. Introduction of a methyl group at the N atom of the sulfonamide group to the COX-2 inhibitor nimesulide resulted in no COX-2 inhibitory activity. This structural modification was utilized in our drug design. The nitrate group at the 4 position of the base compound was retained and modifications of the sulfonamide and of the 2 position alkyl group were made to generate the new compounds.

Figure 17:
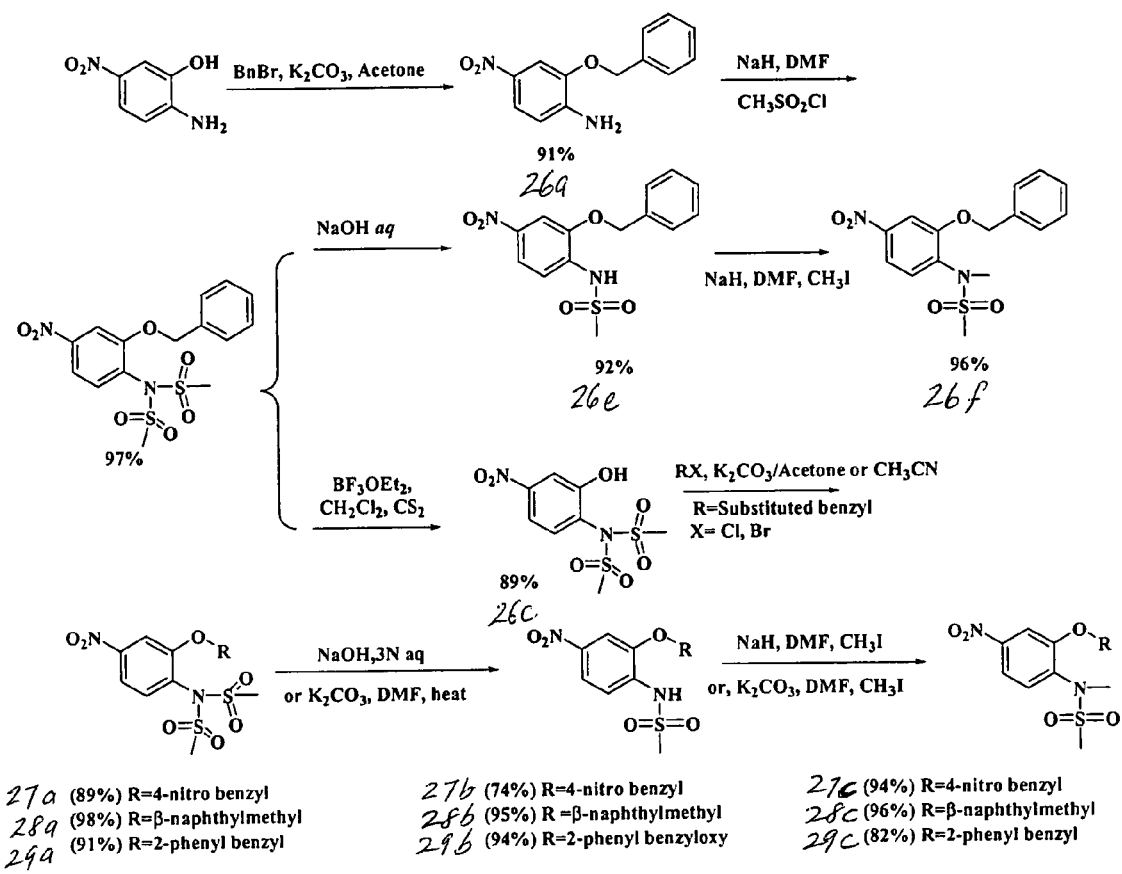
FIG. 17 shows the synthesis of compounds 26-29c.
Figure 18:
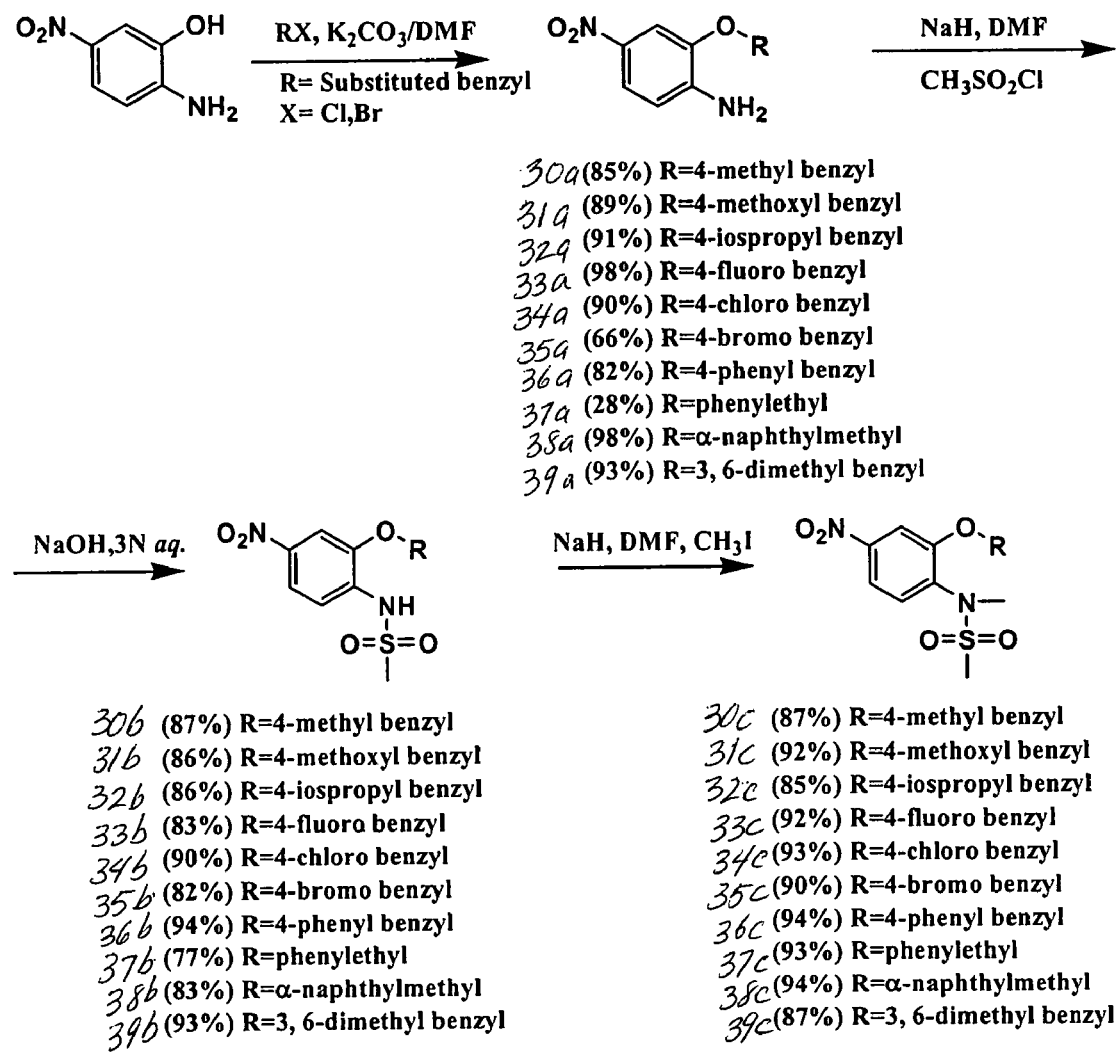
FIG. 18 shows the synthesis of compounds 30a-39c.
Figure 19:
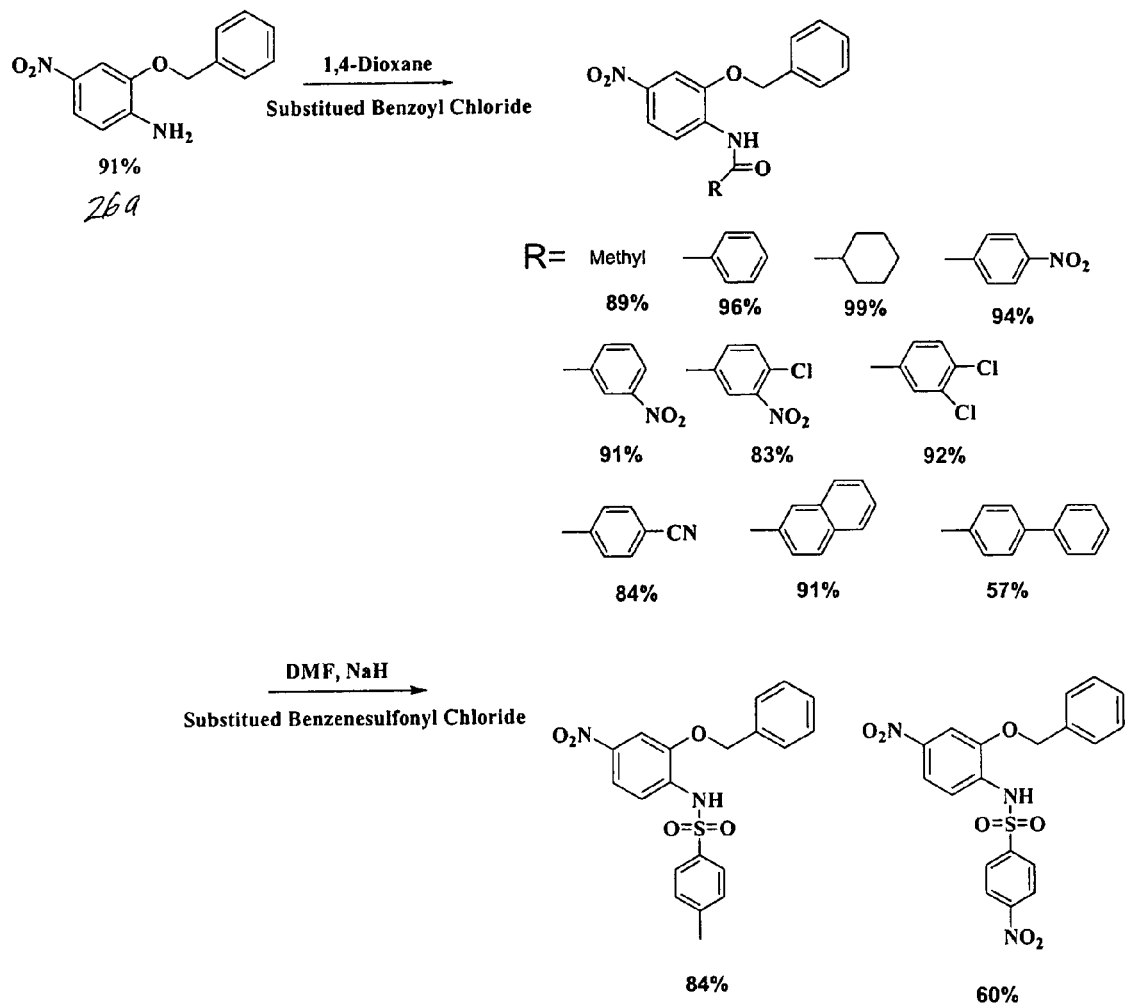
FIG. 19 shows the synthesis of compounds having different substituents at position $R^3$.
Figure 20:
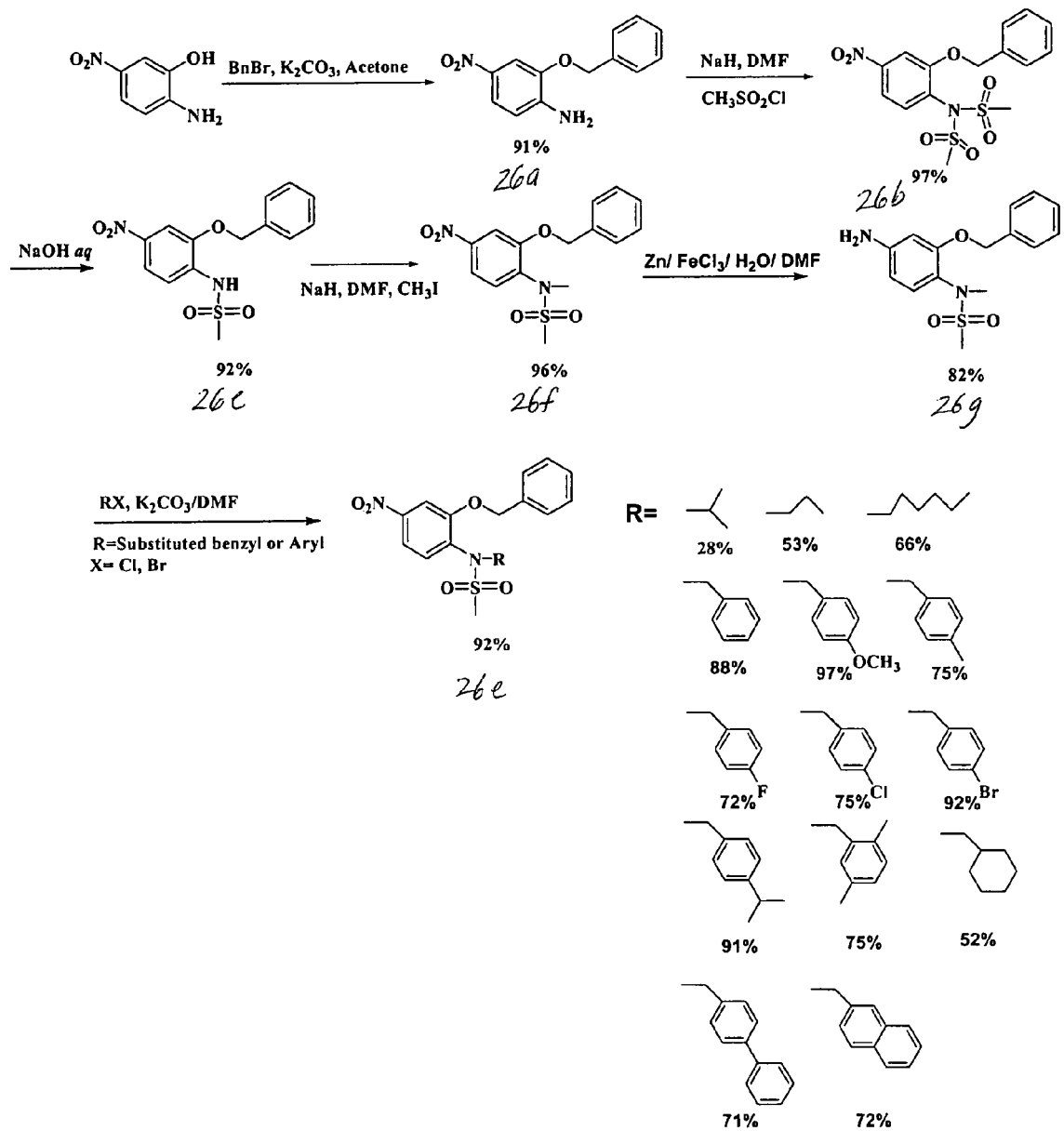
FIG. 20 shows the synthesis of compounds having different substituents at position $R^2$.
Figure 21:
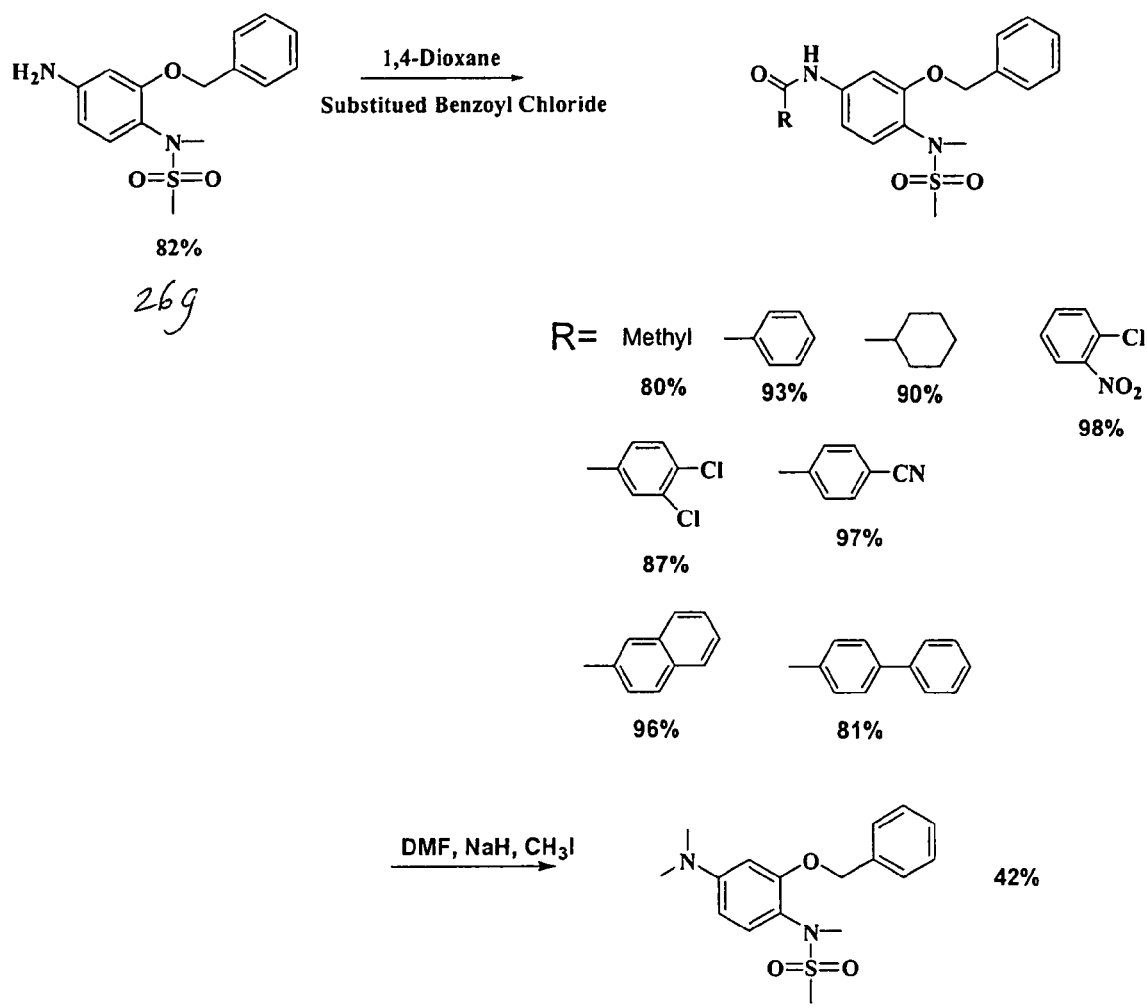
FIG. 21 shows the synthesis of compounds having different substituents at position $R^4$.

The synthesis of the next set of target compounds was carried out in FIGS. 17 and 18, in which R represents substituted benzyl moieties and X represents chloride or bromide. The starting material 2-amino-5-nitrophenol was commercially available. In FIG. 17, 2-amino-5-nitrophenol was refluxed with $K_2CO_3$ and benzyl chloride to obtain compounds 26a. Sodium hydride and methanesulfonyl chloride were added to compound 26a in dry dimethylformamide (DMF) at room temperature and the reaction mixture was stirred at room temperature overnight to obtain the N,N-bimethanesulfonamido (26b). Dealkylation reaction of compound 26b was performed with $BF_3.OEt_2-Me_2S$ in dichloromethane yielding hydroxy compound 26c. In addition, 26b can be hydrolyzed with 10% NaOH solution to generate 26e as a monomethanesulfonamido compound. Compound 26e was treated with $K_2CO_3$ and substituted benzyl chloride/bromide in acetone or $CH_3CN$ at room temperature or refluxed to obtain 27a-29a. Hydrolyzation of 27a-29a generated 27b-29b. Methylation of 26e and 27b-29b gave compounds 26f, 27c-29c, respectively. In FIG. 18, 2-amino-5-nitrophenol was treated with $K_2CO_3$ and substituted benzyl chloride/bromide in DMF to obtain compounds 30a-39a. Sodium hydride and methanesulfonyl chloride were added and resulted in a mixture of N,N-bimethane-sulfonamido and N-methanesulfonamido compounds. The mixture was hydrolyzed with 10% NaOH solution to generate monomethanesulfonamido compounds 30b-39b respectively. Methylation of 30b-39b gave compounds 30c-39c respectively. The structures of all the synthesized compounds were confirmed by $^1HNMR$, $^{13}CNMR$, HRMS, and the composition of key compounds in the biological studies were also confirmed by elemental analysis.

EXAMPLES

Chemistry. Chemicals were commercially available and used as received without further purification unless otherwise noted. Moisture sensitive reactions were carried out under a dry argon atmosphere in flame-dried glassware. Solvents were distilled before use under argon. Thin-layer chromatography was performed on precoated silica gel F254 plates (Whatman). Silica gel column chromatography was performed using silica gel 60A (Merck, 230-400 Mesh). High-resolution electrospray ionization mass spectra were obtained on the Micromass QTOF Electrospray mass spectrometer at The Ohio State Chemical Instrumentation Center. All the NMR spectra were recorded on a Bruker DPX 250 and 400 MHz in either DMSO-d6 or $CDCl_3$. Chemical shifts ($\delta$) for $^1H$ NMR spectra are reported in parts per million to residual solvent protons.

Synthesis. All the compounds were synthesized according to a general procedure described in Scheme 1 (FIG. 1), in which R represents alkyl structures and X represents halogen atom. The starting material 2-amino-5-nitrophenol is commercially available and was treated with $K_2CO_3$ and alkyl halide in DMF at room temperature or refluxed to obtain compounds 1-8. Powder sodium hydride is added to compounds 1-8 in dry dimethylformamide (DMF) at room temperature. After the evolution of hydrogen ended, methanesulfonyl chloride was added and the reaction mixture was stirred at room-temperature overnight. After workup, the resulting mixture of N,Nbimethanesulfonamido and N-methanesulfonamido was hydrolyzed with 10% NaOH solution to generate the base compound and compounds 9-16 as monomethanesulfonamido compounds. Methylation of the base compound and compounds 9-16 yielded compounds 17-25, respectively. All the synthesized compounds tested in the following biological study are confirmed by $^1H$ NMR and HRMS. Key compounds are also confirmed by elemental analysis.

A. General Procedure for the Preparation of 1-8. The halohydrocarbon (6 mmol, 1.2 equiv) and $K_2CO_3$ (0.69 g, 5 mmol) were successively added to a solution of 2-amino-5-nitrophenol (0.77 g, 5 mmol) in DMF (10 mL), and the mixture was refluxed from 2 h to 7 days. After being cooled, 20 mL of $H_2O$ and 5 of mL saturated aqueous $Na_2CO_3$ was added to the mixture, and the aqueous phase was extracted with $CH_2Cl_2$. The organic solution was washed with saturated aqueous $Na_2CO_3$ solution and $H_2O$, dried over anhydrous $MgSO_4$, and concentrated. The residue was chromatographed on silica gel [AcOEt-hexane (1:5)] to afford desired compounds.

2-Cyclohexyloxy-4-nitroaniline (1). Cyclohexyl iodide was used and it was refluxed for 7 days. Yellow oil, 6.5%: 1H NMR (400 MHz, $CDCl_3$) $\delta$ 7.76 (1H, dd, J) 8.7, 2.3 Hz), 7.66 (1H, d, J) 2.1 Hz), 6.64 (1H, d, J) 8.8 Hz), 4.66 (2H, br), 4.34 (1H, m), 2.00 (2H, m), 1.78 (2H, m), 1.56 (3H, m), 1.38 (3H, m).

2-Propyloxy-4-nitroaniline (2). 1-Iodopropane was used and it was refluxed for 2 h. Yellow solid, 82.8%: mp 59-61° C.; $^1H$ NMR (400 MHz, $CDCl_3$) $\delta$ 7.81 (1H, dd, J) 8.7, 2.3 Hz), 7.67 (1H, d, J) 2.1 Hz), 6.65 (1H, d, J) 8.7 Hz), 4.58 (2H, br), 4.05 (2H, dd, J) 6.5, 6.5 Hz), 1.87 (2H, m), 1.08 (3H, dd, J) 7.5, 7.5 Hz).

2-Isopropyloxy-4-nitroaniline (3). 2-Iodopropane was used and it was refluxed for 24 h. Yellow oil, 69.3%: $^1H$ NMR (400 MHz, $CDCl_3$) $\delta$ 7.73 (1H, dd, J) 8.7, 2.4 Hz), 7.62 (1H, d, J) 2.3 Hz), 6.63 (1H, d, J) 8.8 Hz), 4.77 (2H, br), 4.59 (1H, m), 1.34 (6H, d, J) 6.0 Hz).

2-Methylcyclohexyloxy-4-nitroaniline (4). Bromoethyl cyclohexane was used and it was refluxed for 6 h. Yellow solid, 87.5%: mp 54-56° C.; $^1H$ NMR (400 MHz, $CDCl_3$) $\delta$ 7.79 (1H, dd, J) 8.7, 1.9 Hz), 7.64 (1H, d, J) 1.9 Hz), 6.64 (1H, d, J) 8.7 Hz), 4.62 (2H, br), 3.86 (2H, d, J) 6.1 Hz), 1.78 (6H, m), 1.08 (5H, m).

2-Cyclopentyloxy-4-nitroaniline (5). Cyclopentyl iodide was used and it was refluxed for 3 days. Red oil, 47%; $^1H$ NMR (400 MHz, $CDCl_3$) $\delta$ 7.78 (1H, dd, J) 8.7, 2.3 Hz), 7.66 (1H, d, J) 2.3 Hz), 6.63 (1H, d, J) 8.6 Hz), 4.87 (1H, m), 4.56 (2H, br), 1.68-2.02 (8H, m).

2-(1-Ethyl-propyloxy)-4-nitroaniline (6). 3-Bromopentane was used and it was refluxed for 5 days. Yellow solid, 51.7%: mp 62-63° C.; $^1H$ NMR (400 MHz, $CDCl_3$) $\delta$ 7.79 (1H, dd, J) 8.7, 2.3 Hz), 7.67 (1H, d, J) 2.2 Hz), 6.65 (1H, d, J) 8.7 Hz), 4.58 (2H, br), 4.29 (1H, m), 1.72 (4H, m), 0.98 (6H, dd, J) 7.4, 7.4 Hz).

2-Nonyloxy-4-nitroaniline (7). 1-Iodononane was used and it was refluxed for 24 h. Yellow solid, 86.2%: mp 74-75° C.; $^1H$ NMR (400 MHz, $CDCl_3$) $\delta$ 7.80 (1H, dd, J) 8.7, 2.4 Hz), 7.67 (1H, d, J) 2.3 Hz), 6.64 (1H, d, J) 8.7 Hz), 4.57 (2H, br), 4.07 (2H, dd, J) 6.6, 6.6 Hz), 1.84 (2H, m), 1.31 (14H, m), 0.89 (3H, dd, J) 6.7, 6.7 Hz).

2-Hexyloxy-4-nitroaniline (8). 1-Iodohexane was used and it was refluxed for 6 h. Yellow solid, 72.9%: mp 101-104° C.; $^1H$ NMR (400 MHz, $CDCl_3$) $\delta$ 7.81 (1H, dd, J) 8.7, 2.4 Hz), 7.67 (1H, d, J) 2.3 Hz), 6.64 (1H, d, J) 8.7 Hz), 4.58 (2H, br), 4.08 (2H, dd, J) 6.5, 6.5 Hz), 1.85 (2H, m), 1.48 (2H, m), 1.35 (4H, m), 0.92 (3H, dd, J) 6.9, 6.9 Hz).

General Procedure for the Preparation of the base compound and Compounds 9-16. NaH (95% powder, 0.265 g, 10.5 mmol, 3.5 equiv) was added to a solution of alkyl instituted 2-amino-5-nitrophenol (3.0 mmol) in anhydrous DMF (8 mL) at room temperature. After being stirred at the same temperature for 30 min, MsCl (1.031 g, 9.0 mmol, 3 equiv) was added to the mixture, and the stirring was continued overnight at room temperature. $H_2O$ was added to the mixture, and then it was neutralized with 5 N HCl until pH=1-2. The intermediate precipitated as a yellow solid. It was collected by filtration and washed with $H_2O$, which was used to the next reaction without further purification. The intermediate was added to a 3 N NaOH aq solution and was stirred at 80-90° C. overnight. After being cooled, it was neutralized with 5 N HCl until pH=1-2. The precipitated solid was collected and washed with H2O and cold ether to provide the desired product, and then it was recrystallized from ethyl acetate/hexane.

N-(2-Cyclohexyloxy-4-nitrophenyl)methanesulfonamide (base compound). Pale yellow powder, 59.5%: mp 124-126° C.; $^1H$ NMR (250 MHz, $CDCl_3$) $\delta$ 7.89 (dd, J) 2.3, 8.9 Hz, 1H), 7.79 (d, J) 2.4 Hz, 1H), 7.66 (d, J) 8.9 Hz, 1H), 7.24 (br, 1H), 4.44 (m, 1H), 3.12 (s, 3H), 2.06 (m, 2H), 1.84 (m, 2H), 1.41 (m, 6H). Anal. Calcd for $C_{13}H_{18}N_2O_5S$: C, 49.67; H, 5.77; N, 8.91. Found: C, 49.75; H, 5.77; N, 8.80.

N-(2-Propyloxy-4-nitrophenyl)methanesulfonamide (9). Yellow powder, 67.7%: mp 117-119° C.; $^1H$ NMR (250 MHz, $CDCl_3$) $\delta$ 7.92 (dd, J) 2.4, 8.9 Hz, 1H), 7.79 (d, J) 2.4 Hz, 1H), 7.66 (d, J) 8.9 Hz, 1H), 7.25 (br, 1H), 4.12 (t, J) 6.6, 6.6 Hz 2H), 3.13 (s, 3H), 1.89 (m, 2H), 1.08 (t, J) 7.4, 7.4 Hz, 3H); HRMS calculated for $C_{10}H_{14}N_2NaO_5S$ (M+Na)+ 297.0521, found 297.0533.

N-(2-Isopropyloxy-4-nitrophenyl)methanesulfonamide (10). Yellow solid, 81.8%: mp 128-131° C.; $^1H$ NMR (400 MHz, $CDCl_3$) $\delta$ 7.90 (dd, J) 2.3, 9.0 Hz, 1H), 7.79 (d, J) 2.3 Hz, 1H), 7.66 (d, J) 9.0 Hz, 1H), 7.26 (br, 1H), 4.77 (m, 1H), 3.12 (s, 3H), 1.45 (d, J) 6.1 Hz, 6H); HRMS calculated for $C_{10}H_{14}N_2$—$NaO_5S$ (M+Na)+ 297.0521, found 297.0501.

N-(2-Methylcyclohexyloxy-4-nitrophenyl)methanesulfonamide (11). Yellow powder, 80.5%: mp 138-142° C.; $^1H$ NMR (250 MHz, DMSO-d6) $\delta$ 7.64 (dd, J) 2.6, 9.1 Hz, 1H), 7.41 (d, J) 2.7 Hz, 1H), 7.13 (d, J) 9.2 Hz, 1H), 3.72 (d, J) 6.4 Hz 2H), 2.71 (s, 3H), 1.69 (m, 6H), 0.99 (m, 5H); HRMS calculated for C14H20N2NaO5S (M+Na)+ 351.0991, found 351.1017. Anal. Calcd for $C_{14}H_{20}N_2O_5S$: C, 51.21; H, 6.14; N, 8.53. Found: C, 51.08; H, 6.10; N, 8.34.

N-(2-Cyclopentyloxy-4-nitrophenyl)methanesulfonamide (12). Yellow solid 88.5%: mp 139-140° C.; $^1$H NMR (400 MHz, CDCl$_3$) δ 7.90 (dd, J) 2.3, 8.9 Hz, 1H), 7.79 (d, J) 2.3 Hz, 1H), 7.65 (d, J) 8.9 Hz, 1H), 7.19 (br, 1H), 4.95 (m, 1H), 3.12 (s, 3H), 2.06 (m, 2H), 1.59 (m, 6H); HRMS calculated for C12H16N2NaO5S (M+Na)+ 323.0678, found 323.0673. Anal. Calcd for $C_{12}H_{16}N_2O_5S$: C, 47.99; H, 5.37; N, 9.33. Found: C, 47.76; H, 5.45; N, 9.14.

N-(2-(1-Ethyl-propyloxy-4-nitrophenyl))methanesulfonamide (13). Yellow solid, 81.6%: mp 100-102° C.; $^1$H NMR (400 MHz, CDCl$_3$) δ 7.89 (dd, J) 2.4, 9.0 Hz, 1H), 7.78 (d, J) 2.3 Hz, 1H), 7.67 (d, J) 8.9Hz, 1H), 4.38 (m, 1H), 3.12 (s, 3H), 1.75 (m, 4H), 0.98 (t, J) 7.4, 7.4 Hz, 6H); HRMS calculated for $C_{12}H_{18}N_2NaO_5S$ (M+Na)+ 325.0834, found 325.0823. Anal. Calcd for C12H18N2O5S: C, 47.67; H, 6.00; N, 9.27. Found: C, 47.78; H, 6.11; N, 9.22.

N-(2-Nonyloxy-4-nitrophenyl)methanesulfonamide (14). Yellow solid, 94.9%: mp 70-71° C.; $^1$H NMR (400 MHz, CDCl$_3$) δ 7.92 (dd, J) 2.3, 8.9 Hz, 1H), 7.79 (d, J) 2.4 Hz, 1H), 7.66 (d, J) 8.9 Hz, 1H), 7.24 (br, 1H), 4.14 (t, J) 6.7, 6.7 Hz, 2H), 3.12 (s, 3H), 1.86 (m, 2H), 1.31 (m, 12H), 0.89 (t, J) 6.4, 6.4 Hz, 3H); HRMS calculated for $C_{16}H_{26}N_2NaO_5S$ (M+Na)+ 381.1460, found 381.1482.

N-(2-Hexyloxy-4-nitrophenyl)methanesulfonamide (15). Pale yellow solid, 86.8%: mp 74-76° C.; $^1$H NMR (400 MHz, CDCl$_3$) δ 7.92 (dd, J) 2.5, 8.6 Hz, 1H), 7.78 (d, J) 2.5 Hz, 1H), 7.65 (d, J) 8.7 Hz, 1H), 7.23 (br, 1H), 4.14 (t, J) 6.5, 6.5 Hz, 2H), 3.12 (s, 3H), 1.85 (m, 2H), 1.38 (m, 6H), 0.93 (t, J) 6.8, 6.8 Hz, 3H); HRMS calculated for $C_{13}H_{20}N_2NaO_5S$ (M+Na)+339.0991, found 339.0986.

N-(2-Methoxy-4-nitrophenyl)methanesulfonamide (16). Yellow solid, 81.1%: mp 128-130° C.; $^1$H NMR (250 MHz, DMSO-d6) δ 7.83 (dd, J) 2.5, 8.9 Hz, 1H), 7.72 (d, J) 2.5 Hz, 1H), 7.46 (d, J) 8.9 Hz, 1H), 3.90 (s 3H), 3.06 (s, 3H); HRMS calculated for $C_8H_{10}N_2NaO_5S$ (M+Na)+ 269.0208, found 269.0223.

General Procedure for the Preparation of 17-25. The methanesulfonamide compound (0.5 mmol) was dissolved in 3 mL of dry DMF, and NaH powder (15.2 mg 95%, 0.6 mmol, 1.2 equiv) was added. The mixture was stirred at room temperature for 10 min, and iodomethane (0.6 mmol, 1.2 eq) was added; the stirring was kept for 2 h at room temperature. Then the mixture was taken up with 7 mL of water and 2 mL of Na$_2$CO$_3$ aq solution. The precipitated solid was collected by filtration and washed with water and cold ether to afford the desired product, and then it was recrystallized from ethyl acetate/hexane. If oil precipitated, it was extracted by using CH$_2$Cl$_2$. The organic phase was washed with water and Na$_2$CO$_3$ aq solution, dried over anhydrous MgSO$_4$, and concentrated. The residue was chromatographed on silica gel [AcOEt-hexane (1:5)] to afford the product.

N-Methyl-N-(2-cyclohexyloxy-4-nitrophenyl)methanesulfonamide (17). White solid, 89.8%: mp 129-132° C.; $^1$H NMR (400 MHz, CDCl$_3$) δ 7.82 (dd, J) 2.4, 8.6 Hz, 1H), 7.80 (d, J) 2.2 Hz, 1H), 7.55 (d, J) 8.6 Hz, 1H), 4.49 (m, 1H), 3.30 (s, 3H), 2.99 (s, 3H), 2.11 (m, 2H), 1.85 (m, 2H), 1.50 (m, 6H); HRMS calculated for $C_{14}H_{20}N_2NaO_5S$ (M+Na)+ 351.0991, found 351.0970. Anal. Calcd for $C_{14}H_{20}N_2O_5S$: C, 51.21; H, 6.14; N, 8.53. Found: C, 51.23; H, 6.16; N, 8.41.

N-Methyl-N-(2-propyloxy-4-nitrophenyl)methanesulfonamide (18). Pale yellow solid, 82.9%: mp 66-69° C.; $^1$H NMR (400 MHz, CDCl$_3$) δ 7.86 (dd, J) 2.5, 8.6 Hz, 1H), 7.83 (d, J) 2.5 Hz, 1H), 7.55 (d, J) 8.5 Hz, 1H), 4.12 (t, J) 6.6, 6.6 Hz, 2H), 3.32 (s, 3H), 2.99 (s, 3H), 1.92 (m, 2H), 1.12 (t, J) 7.5, 7.5 Hz, 3H); HRMS calculated for $C_{11}H_{16}N_2NaO_5S$ (M+Na)+ 311.0678, found 311.0658.

N-Methyl-N-(2-isopropyloxy-4-nitrophenyl)methanesulfonamide (19). Yellow solid, 89.5%: mp 99-100° C.; $^1$H NMR (400 MHz, CDCl$_3$) δ 7.83 (dd, J) 2.5, 8.5 Hz, 1H), 7.81 (d, J) 2.5 Hz, 1H), 7.55 (d, J) 8.6 Hz, 1H), 4.80 (m, 1H), 3.30 (s, 3H), 2.99 (s, 3H), 1.47 (d, J) 6.1 Hz, 6H); HRMS calculated for $C_{11}H_{16}N_2NaO_5S$ (M+Na)+ 311.0678, found 311.0661.

N-Methyl-N-(2-methylcyclohexyloxy-4-nitrophenyl)methanesulfonamide (20). Yellow powder, 86.7%: mp 105-107° C.; $^1$H NMR (400 MHz, CDCl$_3$) δ 7.86 (dd, J) 2.5, 8.6 Hz, 1H), 7.83 (d, J) 2.4 Hz, 1H), 7.56 (d, J) 8.6 Hz, 1H), 3.96 (d, J) 6.0 Hz 2H), 3.33 (s, 3H), 2.98 (s, 3H), 1.76 (m, 6H), 1.13 (m, 5H); HRMS calculated for C15H22N2NaO5S (M+Na)+ 365.1147, found 365.1169. Anal. Calcd for $C_{15}H_{22}N_2O_5S$: C, 52.62; H, 6.48; N, 8.18. Found: C, 52.62; H, 6.55; N, 8.11.

N-Methyl-N-(2-cyclopentyloxy-4-nitrophenyl)methanesulfonamide (21). Yellow solid 92.9%: mp 102-104° C.; $^1$H NMR (400 MHz, CDCl$_3$) δ 7.90 (dd, J) 2.3, 8.5 Hz, 1H), 7.82 (d, J) 2.5 Hz, 1H), 7.54 (d, J) 8.5 Hz, 1H), 4.98 (m, 1H), 3.29 (s, 3H), 2.97 (s, 3H), 2.08 (m, 2H), 1.78 (m, 6H); HRMS calculated for $C_{13}H_{18}N_2NaO_5S$ (M+Na)+ 337.0834, found 337.0824. Anal. Calcd for $C_{13}H_{18}N_2O_5S$: C, 49.67; H, 5.77; N, 8.91. Found: C, 49.87; H, 5.93; N, 8.78.

N-Methyl-N-(2-(1-ethyl-propyloxy-4-nitrophenyl))methanesulfonamide (22). Yellow solid, 89.5%: mp 89-90° C.; $^1$H NMR (400 MHz, CDCl$_3$) δ 7.82 (dd, J) 2.5, 8.6 Hz, 1H), 7.80 (d, J) 2.4 Hz, 1H), 7.55 (d, J) 8.6 Hz, 1H), 4.42 (m, 1H), 3.31 (s, 3H), 2.98 (s, 3H), 1.77 (m, 4H), 1.02 (t, J) 7.4, 7.4 Hz, 6H); HRMS calculated for $C_{13}H_{20}N_2NaO_5S$ (M+Na)+ 339.0991, found 339.0967. Anal. Calcd for $C_{13}H_{20}N_2O_5S$: C, 49.35; H, 6.37; N, 8.85. Found: C, 49.55; H, 6.43; N, 8.74.

N-Methyl-N-(2-nonyloxy-4-nitrophenyl)methanesulfonamide (23). Yellow solid, 98.8%: mp 83-84° C.; $^1$H NMR (400 MHz, CDCl$_3$) δ 7.85 (dd, J) 2.5, 8.6 Hz, 1H), 7.82 (d, J) 2.5 Hz, 1H), 7.55 (d, J) 8.6 Hz, 1H), 4.14 (t, J) 6.6, 6.6 Hz, 2H), 3.31 (s, 3H), 2.99 (s, 3H), 1.88 (m, 2H), 1.50 (m, 2H), 1.31 (m, 10H), 0.89 (t, J) 6.6, 6.6 Hz, 3H); HRMS calculated for $C_{17}H_{28}N_2$—NaO$_5$S (M+Na)+ 395.1617, found 395.1612.

N-Methyl-N-(2-hexyloxy-4-nitrophenyl)methanesulfonamide (24). Yellow oil, 99.3%: mp 44-46° C.; $^1$H NMR (400 MHz, CDCl$_3$) δ 7.84 (dd, J) 2.5, 8.6 Hz, 1H), 7.82 (d, J) 2.5 Hz, 1H), 7.54 (d, J) 8.7 Hz, 1H), 4.15 (t, J) 6.6, 6.6 Hz, 2H), 3.31 (s, 3H), 2.98 (s, 3H), 1.88 (m, 2H), 1.52 (m, 2H), 1.37 (m, 4H), 0.92 (t, J) 7.0, 7.0 Hz, 3H); HRMS calculated for $C_{14}H_{22}N_2$—NaO$_5$S (M+Na)+ 353.1147, found 353.1178.

N-Methyl-N-(2-methoxy-4-nitrophenyl)methanesulfonamide (25). Pale yellow solid, 89%: mp 125-126° C.; $^1$H NMR (400 MHz, DMSO-d6) δ 7.87 (d, J) 2.1 Hz, 1H), 7.84 (dd, J) 2.1, 8.5 Hz, 1H), 7.56 (d, J) 8.5 Hz, 1H), 3.98 (s, 3H), 3.18 (s, 3H), 3.09 (s, 3H); HRMS calculated for $C_9H_{12}N_2NaO_5S$ (M+Na)+ 283.0365, found 283.0373.

Biological Study Preparation of Human Placental Microsomes. Human term placentas were processed immediately after delivery from The Ohio State University Hospitals at 4° C. The placenta was washed with normal saline, and connective and vascular tissue was removed. Microsomes were prepared from the remaining tissue using the method previously described. (Kellis, J. T., Jr.; Vickery, L. E. Purification and characterization of human placental aromatase cytochrome P-450. J. Biol. Chem. 1987, 262, 4413-4420; incorporated herein by reference). Microsomal suspensions were stored at −80° C. until required.

Inhibition Study. Inhibition of human placental aromatase was determined by monitoring the amount of 3H2O released as the enzyme converts [1β-$^3$H]androst-4-ene-3,17-dione to estrone. All the compounds were tested at 5 µM for their potential aromatase inhibitory activity. Aromatase activity assays were carried in 0.1 M potassium phosphate buffer (pH 7.0) with 5% propylene glycol. All samples contained a NADPH regenerating system consisting of 2.85 mM glucose-6-phosphate, 1.8 mM NADP$^+$, and 1.5 units of glucose-6-phosphate dehydrogenase (Sigma, St. Louis, Mo.). Samples contained 100 nM androst-4-ene-3,17-dione (400 000-450 000 dpm). Reactions were initiated with the addition of 50 µg microsomal protein. The total incubation volume was 2.0 mL. Incubations were allowed to proceed for 15 min in a shaking water bath at 37° C. Reactions were quenched by the addition of 2.0 mL of chloroform. Samples were then vortexed and centrifuged for 5 min, and the aqueous layer was removed. The aqueous layer was subsequently extracted twice in the same manner with 2.0 mL of chloroform. A 0.5 mL aliquot of the final aqueous layer was combined with 5 mL of 3a70B scintillation cocktail (Research Products International Corp., Mt. Prospect, Ill.) and the amount of radioactivity determined. Each sample was run in triplicate, and background values were determined with microsomal protein inactivated by boiling. Samples containing 50 µM (±)-aminoglutethimide (Sigma, St. Louis, Mo.) were used a positive control. The data were analyzed with the Graphpad Prism (Version 3.0) program.

Aromatase Tritiated Water-Release Assay in SK-BR-3 Cell Lines. SK-BR-3 cells were obtained from ATCC (Rockville, Md.). Cell cultures were maintained in phenol red-free custom media (MEM, Earle's salts, 1.5× amino acids, 2× nonessential amino acids, L-glutamine, 1.5× vitamins, Gibco BRL) supplemented with 10% fetal bovine serum (FBS), 2 mM L-glutamine, and 20 mg/L gentamycin. Measurement of aromatase enzyme activity was based on the tritium water release assay. 24 Cells in 100 mm Petri dish were treated with 0.1% DMSO (control), and inhibitors at the indicated concentrations. After 24 h, the media was changed and the cells were incubated with 100 nM [1â-3H]-androst-4-ene-3,17-dione (2 Ci) for 3 h. Subsequently, the reaction mixture was removed, and proteins were precipitated using 10% trichloroacetic acid at 42° C. for 20 min. After a brief centrifugation, the media was extracted three times with an equal amount of chloroform to extract unused substrate and further dextran-treated charcoal. After centrifugation, a 250-µL aliquot containing the product was counted in 5 mL of liquid scintillation mixture. Results were corrected for blanks and for the cell contents of culture flasks, and results were expressed as picomoles of $3H_2O$ formed per hour incubation time per million live cells (pmol/h/$10^6$ cells). To determine the amount of cells in each flask, the cells were trypsinized and analyzed using the diphenylamine DNA assay adapted to a 96-well plate. (Natarajan N.; Shambaugh, G. E., 3rd; Elseth K. M.; Haines G. K.; Radosevich J. A. Adaptation of the diphenylamine (DPA) assay to a 96-well plate tissue culture format and comparison with the MTT assay. Biotechniques 1994, 17, 166-171; incorporated herein by reference). IC$_{50}$ sigmoidal dose-response data were analyzed with Microsoft Excel and the Graphpad Prism (Version 3.0) program.

Enzyme Immunoassay of PGE2 in MDA-MB-231 Cells. MDA-MB-231 cells were obtained from ATCC (Rockville, Md.). Cell cultures were maintained in phenol red-free custom media (MEM, Earle's salts, 1.5× amino acids, 2× nonessential amino acids, L-glutamine, 1.5× vitamins, Gibco BRL) supplemented with 10% fetal bovine serum (FBS), 2 mM L-glutamine and 20 mg/L gentamycin. To study PGE2 synthesis in cell culture media, experiments were performed in 6015 mm Petri dishes. An aliquot of MDA-MB-231 cells (15×10$^4$ cells) were added to each dish and then incubated overnight to allow the cells to adhere to the dish. After that, cells were serum starved in defined media for 24 h. This step was followed by replacement of media with fresh media containing either vehicle (DMSO) or the indicated concentration of agents. After 24 h incubation at 37° C. the media were collected and the amount of PGE$_2$ was determined by ELISA (Cayman Chemical) according to the protocol provided by the manufacturer. PGE$_2$ concentration was normalized to total protein. Total proteins were extracted from adhered cells by 30 min treatment with 0.5 M NaOH at room temperature and shaking. Protein concentrations in these extracts were determined using a protein assay method (Bio-Rad Laboratories, Inc., Hercules, Calif.).

RNA Extraction. Total RNA was isolated using the TRIzol reagent according to the manufacturer's protocol. Total RNA pellets were dissolved in DNase- and RNase-free water and quantitated using a spectrophotometer. The quality of RNA samples was determined by electrophoresis through agarose gels and staining with ethidium bromide; the 18S and 28S rRNA bands were visualized under ultraviolet light.

cDNA Synthesis. Isolated total RNA (2 µg) was treated with DNase I Amplification grade, according to the recommended protocol to eliminate any DNA before reverse transcription. Treated total RNA was denatured at 65° C. for 5 min in the presence of 2.5 ng/µL random hexamers and 0.5 mM dNTP mix. The samples were snap-cooled on ice and centrifuged briefly. Complementary DNA (cDNA) was synthesized using Superscript II reverse transcriptase according to the recommended protocol. Briefly, the reactions were conducted in the presence of 1× First-Strand Buffer and 20 mM DTT at 42° C. for 50 min and consequently inactivated at 70° C. for 15 min. The cDNA generated was used as a template in realtime PCR reactions.

Real-Time PCR. Real-time PCR was performed using the Opticon 2 system from MJ Research (Waltham, Mass.). For the CYP19 total gene the PCR reaction mixture consisted of Taqman Universal PCR Master Mix (Applied Biosystems), 600 nM of CYP19 primer (sense: 5'-TGT CTC TTT GTT CTT CAT GCT ATT TCT C-3' (SEQ ID NO: 1); antisense: 5'-TCA CCA ATA ACA GTC TGG ATT TCC-3') (SEQ ID NO: 2); 250 nM Taqman probe (6FAM 5'-TGC AAA GCA CCC TAA TGT TGA AGA GGC AAT-3'TAMRA) (SEQ ID NO: 3) (Invitrogen), 18S rRNA (Applied Biosystems, Foster City, Calif.), and 2.0 µL of each RT sample in a final volume of 20 µL. The Taqman probe was designed to anneal to a specific sequence of the aromatase gene between the forward and the reverse primers. Cycling conditions were 50° C. for 2 mm and 95° C. for 10 mm, followed by 50 cycles at 95° C. for 15 s and 60° C. for 1 mm.

Figure 2:
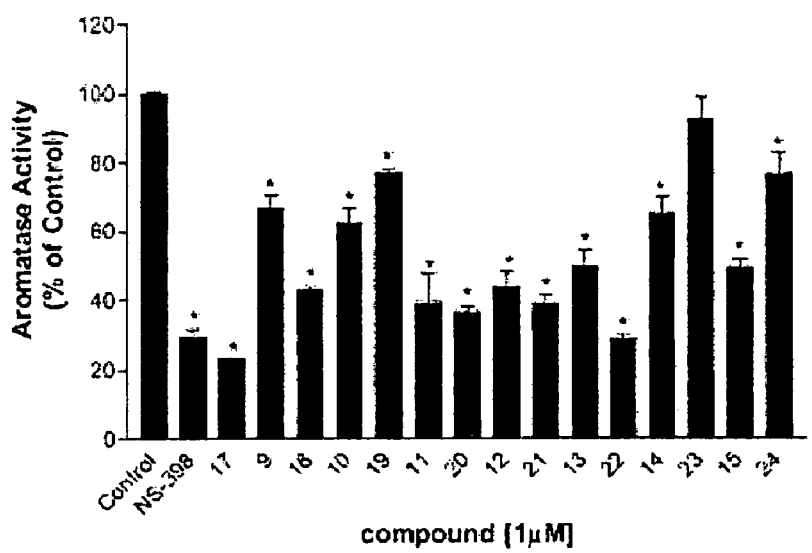
FIG. 2 shows suppression of aromatase activity in SK-BR-3 breast cancer cells. SK-BR-3 cells were treated with indicated compounds (1 µM), aromatase activity was measured as described herein. Values are expressed as picomoles $^3H_2O$ formed per hour incubation time per million cells, the results were normalized against a control treatment with vehicle. The value of 100% is equal to 0.03 pmol/h/$10^6$. Each data bar represents the mean results of three independent determinations. *P<0.05 vs control by unpaired t test.
Figure 3:
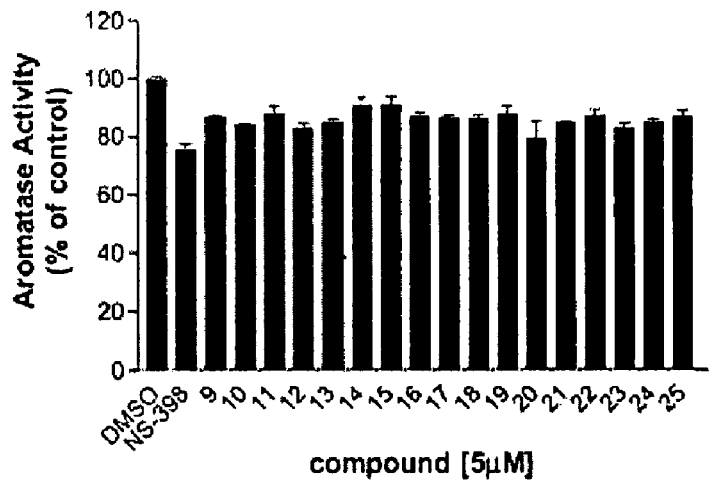
FIG. 3 shows microsomal aromatase activities of the base compound and several of the compounds described herein. The results were normalized against a control treatment with vehicle. Each data bar represents the mean results of three independent determinations.

Biological Evaluation. Aromatase Activity Assay in SK-BR-3 Breast Cancer Cell Line. To investigate whether these compounds decrease aromatase activity in breast cancer cells, we first performed a 25 µM bioassay in SK-BR-3 breast cancer cells (data not show). All the compounds tested, with the exception of 16 and 25, suppressed aromatase activity by almost 80-90%. At 1 µM, most compounds still significantly decrease aromatase activity (FIG. 2). In an effort to discriminate among compounds in this library, dose-response studies of the active compounds were performed, and the resulting IC$_{50}$ values of the compounds are listed in Table 1. Our results suggest that the length of the group on position 2 of the compounds is important for the suppression of aromatase activity. Compounds containing a methoxy (16 and 25) or an isopropyloxy (10 and 19), which are relatively short, have low ability to suppress aromatase activity. Extremely long chain substituents (15, 24, 14, and 23) have reduced activity as well, which may also be due to the poor solubility of the compounds. All the N-methyl compounds exhibited better activity than their corresponding unsubstituted compounds with the exception of compounds 23 and 24. One possible explanation is the pKa value of the reagents. Compounds without N-methyl group have low pKa (3-4) and are deprotonated very easily in the cell culture media. The negative charge may reduce the ability of the drug to penetrate the cell membrane. For compounds 23 and 24, the phenomenon is reversed. They are less effective than their corresponding unsubstituted compounds 14 and 15, respectively. The possible reason is the large side chain on the four compounds, which imparts low water solubility due to their hydrophobic effect. However, compounds 14 and 15 are easily deprotonated in cell culture media; the resulting negative charge may increase the solubility of the drugs to enhance their activity. The best compounds from the first set, 17, 12 and 21, 13 and 22, have a medium-sized side chain, which may bind more effectively to the target molecule. Compounds 13 and 22 with more flexible side chains are the best compounds in this library for suppression of aromatase activity.

TABLE 1

Suppression of Aromatase Activity in SK-BR-3 Breast Cancer Cells[a]

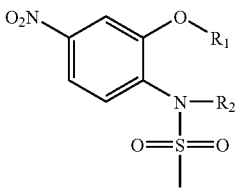

| Compound | | | | IC$_{50}$ (µM) |
|---|---|---|---|---|
| NS-398 | R$_1$ = | 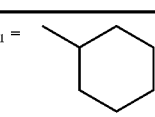 | R$_2$ = H | 0.68 |
| 17 | R$_1$ = | 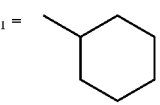 | R$_2$ = CH$_3$ | 0.47 |
| 9 | R$_1$ = |  | R$_2$ = H | 2.51 |
| 18 | R$_1$ = |  | R$_2$ = CH$_3$ | 0.76 |
| 10 | R$_1$ = | 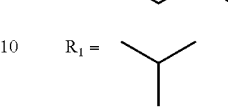 | R$_2$ = H | 5.87 |
| 19 | R$_1$ = | 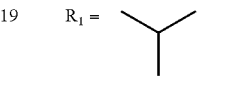 | R$_2$ = CH$_3$ | 2.81 |
| 11 | R$_1$ = | 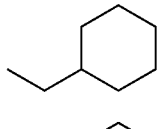 | R$_2$ = H | 1.21 |
| 20 | R$_1$ = | 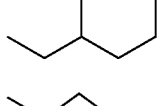 | R$_2$ = CH$_3$ | 0.96 |
| 12 | R$_1$ = | 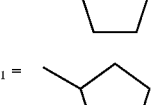 | R$_2$ = H | 0.87 |
| 21 | R$_1$ = | 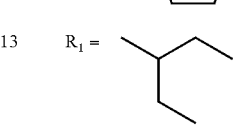 | R$_2$ = CH$_3$ | 0.44 |
| 13 | R$_1$ = |  | R$_2$ = H | 0.30 |

TABLE 1-continued

Suppression of Aromatase Activity in SK-BR-3 Breast Cancer Cells[a]

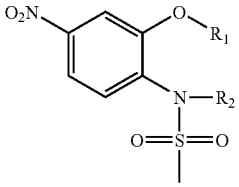

| Compound | | | IC$_{50}$ (µM) |
|---|---|---|---|
| 22 | R$_1$ = 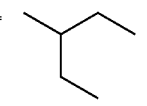 | R$_2$ = CH$_3$ | 0.23 |
| 14 | R$_1$ = 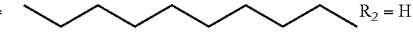 | R$_2$ = H | 0.91 |
| 23 | R$_1$ = 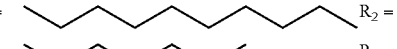 | R$_2$ = CH$_3$ | 3.96 |
| 15 | R$_1$ =  | R$_2$ = H | 2.67 |
| 24 | R$_1$ =  | R$_2$ = CH$_3$ | 4.49 |
| 16 | R$_1$ = CH$_3$ | R$_2$ = H | >25 |
| 25 | R$_1$ = CH$_3$ | R$_2$ = CH$_3$ | >25 |

[a]IC$_{50}$ values were calculated by a nonlinear regression analysis (Graph-Pad Prism).
Each dose-response curve contained five concentrations, each in triplicate.

Time-Course Studies for Suppression of Aromatase Activity in SK-BR-3 Cells. Time-course studies in SK-BR-3 cells demonstrated a prolonged reversible suppression of aromatase by the base compound (2 µM) and compound 17 (2 µM) in a time dependent manner. Cycloheximide (10 µM), which blocks de novo protein synthesis, showed similar results, whereas the aromatase inhibitor letrozole (10 nM) showed an acute inhibition (data not shown). In a separate time-course study, the suppression of aromatase activity of the four agents were shown to be reversible (data not shown). After removal of the drugs, aromatase activity returned in a time-dependent manner. However, in letrozole treatment, aromatase activity returned and resulted in a 150% increase after removing the drug. This is consistent with the finding that aromatase inhibitors can stabilize aromatase enzyme and thus reduce enzyme degradation. In brief, timecourse studies demonstrated a prolonged, reversible suppression of aromatase by the base compound and compound 17 in SK-BR-3 cells.

Figure 4:
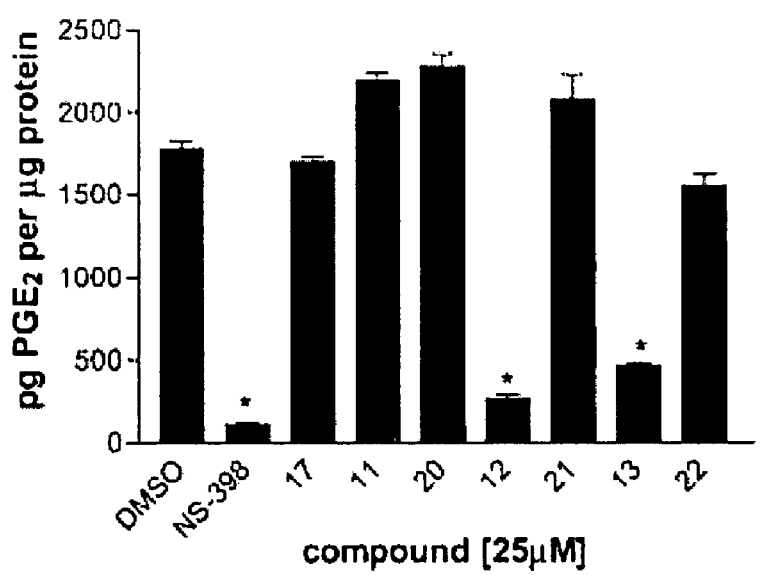
FIG. 4 shows the effect of the base compound and compounds 17, 11, 20, 12, 21, 13, and 22 on $PGE_2$ production of MB-231 cells. Cells were treated for 24 h with the indicated agents at 25 µM. Results are expressed as means of the concentration of $PGE_2$ produced per microgram protein±SEM., *P<0.05 vs control by unpaired t test (n=6).

Level of PGE2 Production in MDA-MB-231 Cell Line. The production of PGE2 was measured in cells treated with the base compound and the novel sulfonanilide derivatives. MDAMB-231 cell line was chosen because of its high cyclooxygenase activity. Cells were treated for 24 h with the indicated concentration (25 µM) of the agents. The base compound, compound 12 and 13 resulted in a significantly decrease in PGE2 production. Compounds 17, 20, 21, and 22 did not show any inhibitory activity (FIG. 4). This is consistent with our design approach that the introduction of a methyl group in to the N atom of the sulfonamide group results in analogues that cannot be deprotonated and thus loses COX-2 inhibitory activity. In addition, compound 11 did not show any COX-2 inhibitory activity, and compound 11 has one carbon longer side chain comparing with the base compound. This result suggests that the size of the side chain is important for the COX-2 inhibitory activity and that this extension affects the binding of the compound with COX-2 and results in no COX-2 inhibitory activity.

Figure 5:
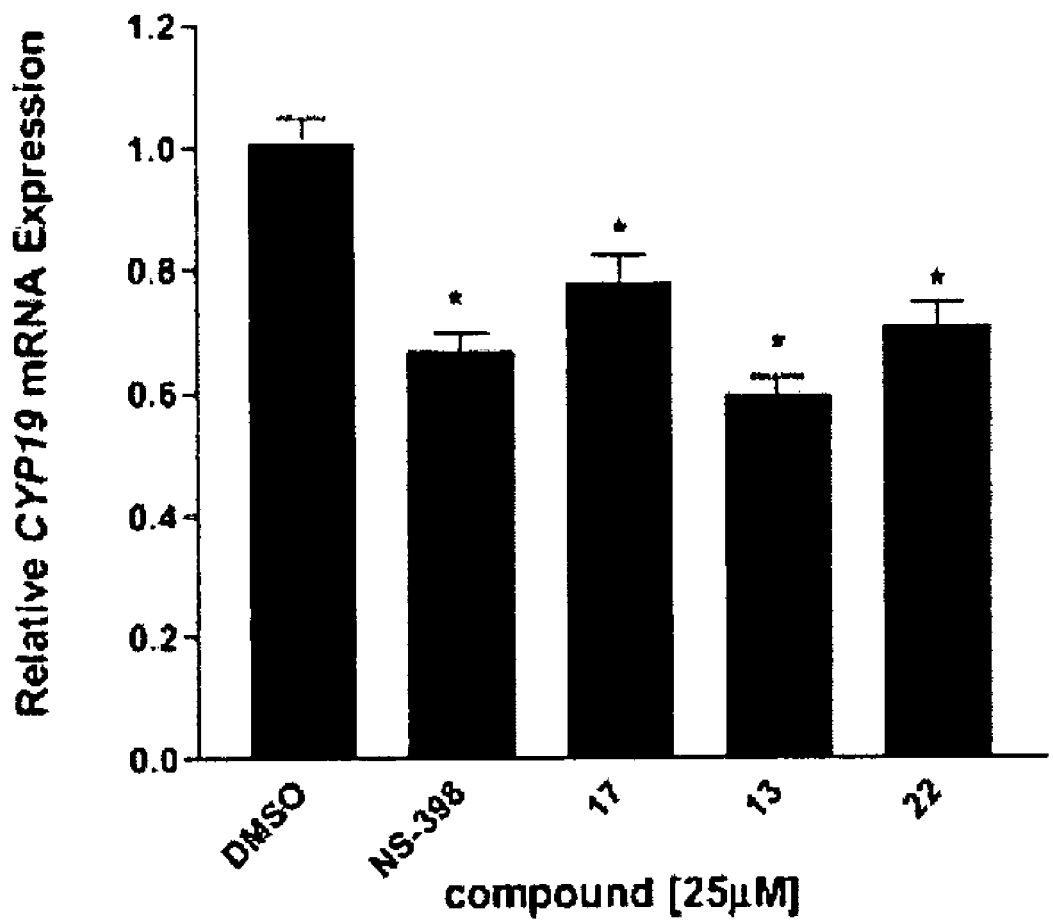
FIG. 5 shows real-time RT-PCR analysis of CYP19 mRNA expression in SK-BR-3 cells. Cells were treated for 24 h with the indicated agents at 25 µM, and total RNA was isolated. Results are expressed as means of CYP19 (normalized to 18S rRNA) ±SEM., *P<0.05 vs control by unpaired t test (n=9).

CYP19 mRNA Expression by Real-Time PCR. Analysis of total CYP19 mRNA transcripts was performed using real-time PCR in order to determine whether the decrease in aromatase activity by the base compound in SK-BR-3 cells was due to a down-regulation of aromatase expression at transcriptional level. SK-BR-3 cells were treated with the base compound, compound 17, 13, and 22 for 24 h at concentrations at 25 µM. Total RNA was extracted at 24 h, and CYP19 transcript levels were compared to control (vehicle) treatment. All four compounds significantly decreased CYP19 gene expression in SK-BR-3 cells relative to the control (FIG. 5). No effect on the expression level of the housekeeping 18S rRNA was observed with any of the compounds. Compounds 17 and 22, which do not show COX-2 inhibitory activity, decrease aromatase expression at similar levels. This suggests that the compounds interfere with pathways affecting aromatase expression in breast cancer cells that do not involve prostaglandins and COX enzyme activities.

The selective COX-2 inhibitor chosen as the base compound, proved to be a good lead compound for decreasing aromatase activity in breast cancer cells by suppression of CYP19 mRNA at the transcriptional level. The potent regulatory activity of this compound suggests that COX-2 independent mechanisms may be involved in its mechanism of action. The present study reports a convenient synthetic approach for preparation of novel sulfonanilide compounds. The sulfonanilide analogues suppress aromatase activity in a dose- and time-dependent manner in SKBR-3 breast cancer cells. Human placenta microsomal assay demonstrates that the compounds do not directly inhibit the aromatase enzyme reaction at concentration above the IC$_{50}$ from cell study. In the COX-2 inhibition study, the base compound and compound 12 and 13 showed COX-2 inhibitory activity, but their corresponding N-methyl compounds (17, 21, and 22, respectively) and compounds 11 and 20 did not have any COX-2 inhibitory activity. This suggests that COX-2 inhibitory activity is not necessary for the suppression of aromatase activity. Furthermore, real time PCR demonstrated that the base compound and derivatives decreased CYP19 gene expression. These results suggest that the novel sulfonanilide compounds suppressed aromatase activity and transcription in SK-BR-3 cells independent of COX-2 inhibition. The expression of aromatase is very complex, and researchers also found that some orphan/nuclear receptors such as ERRα-1, EAR-2, COUP-TFI, and RARγ are involved in the regulation of aromatase expression.[20,21] In addition, MAPK pathway is involved to regulate aromatase expression as well.[22] It is still too early to speculate which pathway(s) the compounds are targeting for the regulation of aromatase activity and transcription.

Additional Compounds

Chemicals were commercially available and used as received without further purification unless otherwise noted. Moisture sensitive reactions were carried out under a dry argon atmosphere in flame-dried glassware. Solvents were distilled before use under argon. Thin-layer chromatography was performed on precoated silica gel F254 plates (Whatman). Silica gel column chromatography was performed using silica gel 60A (Merck, 230-400 Mesh). High-resolution electrospray ionization mass spectra were obtained on the Micromass QTOF Electrospray mass spectrometer at The Ohio State Chemical Instrumentation Center. All the NMR spectra were recorded on a Bruker DPX 250 and DRX 400 MHz in either DMSO-$d_6$ or CDCl$_3$. Chemical shifts (δ) for $^1$H NMR spectra are reported in parts per million to residual solvent protons. Chemical shifts (δ) for $^{13}$C NMR spectra are reported in parts per million relative to residual solvent carbons.

2-Benzyloxy-4-nitroaniline (26a) $K_2CO_3$ (9.0 g, 65.1 mmol) and benzyl bromide g, 33.1 mmol) were successively added to a solution of 2-amino-5-nitrophenol (5.0 g, 32.5 mmol) in acetone (250 ml) and the mixture was refluxed for 8 h. After being cooled, the inorganic precipitate was filtered through a Celite pad and the filtrate was concentrated in vacuo. The resulting solid was recrystallized from AcOEt to afford 26a (7.2 g, 91%) as yellow needles: mp 148-149° C.; $^1$H-NMR (400 MHz, CDCl$_3$) δ7.84 (1H, dd, J=8.7, 2.4 Hz), 7.80 (1H, d, J=2.4 Hz), 7.38 (5H, m), 6.69 (1H, d, J=8.7 Hz), 4.73 (2H, br); $^{13}$C NMR (100 MHz, CDCl$_3$) δ145.20, 136.07, 129.19, 128.98, 128.33, 119.72, 112.86, 107.67, 71.32.

N,N-(2-benzyloxy-4-nitrophenyl) dimethanesulfonamide (26b) NaH (95%, 3.03 g, 120 mmol) was added to a solution of 26a (7.33 g, 30 mmol) in anhydrous DMF (80 ml) at room temperature. After being stirred at the same temperature for 30 min, MsCl (10.31 g, 90 mmol) was added to the mixture slowly and the stirring was continued over night at room temperature. 150 mL H2O and 20 mL saturated Na$_2$CO$_3$ were added to the mixture and the precipitated solid was collected by filtration and washed with H$_2$O and cold ether/hexane mixture to afford 26b as yellow powder (11.62 g, 97%): mp 188-189° C.; $^1$H-NMR (400 MHz, DMSO-$d_6$) δ8.04 (1H, d, J=1.7 Hz), 7.89 (2H, m), 7.53 (2H, d, J=7.7 Hz), 7.38 (3H, m), 5.41 (2H, s), 3.46 (6H, s); $^{13}$C NMR (100 MHz, DMSO-$d_6$) δ157.42, 150.16, 136.25, 134.69, 129.40, 129.38, 129.17, 128.57, 116.70, 109.42, 71.80, 44.59.

N,N-(2-hydroxy-4-nitrophenyl) dimethanesulfonamide (26c) To a stirred suspension of 26b (800.7 mg, 2 mmol) in Me$_2$S (15 mL) and CH$_2$Cl$_2$ (15 mL) was slowly added BF$_3$—OEt$_2$ (5.07 mL, 40 mmol) at room temperature. The resulting yellow solution was vigorously stirred at room-temperature overnight. After cooling to 0° C., the reaction mixture was quenched with water and concentrated under reduced pressure. The insoluble product was collected by filtration and washed with H$_2$O and CHCl$_3$ to give a pale yellow solid (0.554 g, 89%): mp 249-253° C. (decomposed); $^1$H-NMR (400 MHz, DMSO-$d_6$) δ11.65 (1H, s), 7.69 (3H, m), 3.56 (6H, s); $^{13}$C NMR (100 MHz, DMSO-$d_6$) δ157.29, 149.75, 134.54, 128.32, 114.83, 111.82, 44.74.

N-(2-benzyloxy-4-nitrophenyl) methanesulfonamide (26e) Compound 26c (0.4 g, 1 mmol) was added to a 3N NaOH aq solution and was stirred at 80~90° C. overnight. After cool down, it was neutralized with 5N HCl until Ph=1~2. The precipitated solid was collected and washed with H$_2$O and cold ether to provide the desired product, then it was recrystallized from ethyl acetate/hexane to afford pale yellow solid (0.30 g, 92%): mp 150-152° C.; $^1$H-NMR (400 MHz, CDCl$_3$) δ7.94 (1H, dd, J=8.9, 2.3 Hz), 7.91 (1H, d, J=2.3 Hz), 7.68 (1H, d, J=8.9 Hz), 7.43 (5H, m), 7.26 (1H, br), 5.23 (2H, s), 3.09 (3H, s); $^{13}$C NMR (100 MHz, CDCl$_3$) δ147.12, 144.14, 134.74, 133.40, 129.63, 129.53, 128.65, 118.30, 116.96, 107.90, 72.30, 40.65; HRMS calculated for $C_{14}H_{14}N_2NaO_5S$ (M+Na)$^+$ 345.0521, found 345.0531.

N-methyl-N-(2-benzyloxy-4-nitrophenyl) methanesulfonamide (26f) Compound 26e (0.16 g, 0.5 mmol) was dissolved in 3 mL dry DMF and NaH powder (15.2 mg 95%, 0.6 mmol, 1.2 eq) was added. The mixture was stirred at room temperature for 10 minutes and iodomethane (0.6 mmol, 1.2 eq) was added; the stirring was kept for 2 h at room temperature. Then the mixture was taken up with 7 mL of water and 2 mL of Na$_2$CO$_3$ aq solution. The precipitated solid was collected by filtration and washed with water and cold ether to afford the desired product, then it was recrystallized from ethyl acetate/hexane to afford pale yellow solid (0.16 g, 96%): mp 138-140° C.; $^1$H-NMR (400 MHz, CDCl$_3$) δ7.95 (1H, d, J=2.4 Hz), 7.89 (1H, dd, J=8.6, 2.5 Hz), 7.56 (1H, d, J=8.6 Hz), 7.43 (5H, m), 5.23 (2H, s), 3.28 (3H, s), 2.83 (3H, s); $^{13}$C NMR (100 MHz, CDCl$_3$) δ155.68, 148.41, 135.77, 134.97, 133.10, 129.52, 129.46, 128.60, 116.98, 108.48, 71.98, 38.91, 37.92; HRMS calculated for $C_{15}H_{16}N_2NaO_5S$ (M+Na)$^+$ 359.0678, found 359.0663. Anal. ($C_{15}H_{16}N_2O_5S$) C, H, N.

General procedure for the preparation of 27a-29a $K_2CO_3$ (0.69 g, 5 mmol) and aryl halide (5 mmol, 1.0 eq) were successively added to a solution of compound 1c (0.77 g, 5 mmol) in CH$_3$CN or acetone and the mixture was stirred at room temperature or refluxed from 3 h to overnight. After being cooled, 20 mL H$_2$O and 5 mL saturated aqueous Na$_2$CO$_3$ was added to the mixture and the precipitated solid was collected by filtration and washed with H$_2$O and cold ethyl ether to afford desired compounds.

N,N-[2-(4'-nitro-benzyloxy)-4-nitrophenyl]dimethanesulfonamide (27a) It is stirred and refluxed in acetone for 2 h. White powder, 89%: mp 265-269° C. (decomposed); $^1$H-NMR (400 MHz, DMSO-$d_6$) δ8.28 (2H, d, J=8.8 Hz), 8.05 (1H, d, J=2.3 Hz), 7.93 (1H, dd, J=8.6, 2.3 Hz), 7.89 (2H, d, J=8.6 Hz), 7.80 (2H, d, J=8.8 Hz), 5.59 (2H, s), 3.50 (6H, s); $^{13}$C NMR (100 MHz, DMSO-$d_6$) δ157.10, 150.20, 148.13, 144.10, 135.00, 129.29, 129.21, 124.55, 117.06, 109.48, 70.58, 44.61.

N,N-[2-(β-naphthylmethoxy)-4-nitrophenyl]dimethanesulfonamide (28a) It is stirred in CH$_3$CN at room temperature over night. White powder, 98%: mp 184-185° C.; $^1$H-NMR (400 MHz, CDCl$_3$) δ8.05 (1H, d, J=2.4 Hz), 8.04 (1H, s), 7.95 (2H, dd, J=8.5, 2.3 Hz), 7.88 (2H, m), 7.64 (1H, dd, J=8.5, 1.7 Hz), 7.52 (3H, m), 5.44 (2H, s), 3.37 (6H, s); $^{13}$C NMR (100 MHz, CDCl$_3$) δ157.35, 150.21, 133.77, 133.57, 133.47, 132.00, 129.24, 128.55, 128.22, 127.69, 127.11, 127.02, 125.74, 116.88, 109.14, 72.52, 44.29.

N,N-[2-(2'-phenyl benzyloxy)-4-nitrophenyl]dimethanesulfonamide (29a) It is stirred in CH$_3$CN at room temperature over night. White powder, 91%: mp 182-184° C.; $^1$H-NMR (400 MHz, CDCl$_3$) δ7.88 (1H, dd, J=8.6, 2.4 Hz), 7.68 (2H, m), 7.40 (9H, m), 5.19 (2H, s), 3.38 (6H, s); $^{13}$C NMR (100 MHz, CDCl$_3$) δ157.12, 150.10, 142.79, 140.10, 133.15, 131.84, 130.81, 130.20, 129.59, 129.49, 129.08, 129.03, 128.33, 128.22, 116.68, 109.15, 70.31, 44.24.

General procedure for the preparation of 27b-29b Compound 27a-29a was added to a 3N NaOH aq solution or CH$_3$CN/K$_2$CO$_3$ suspension and was stirred at 80~90° C. from 24 to 48 h. After cool down, H$_2$O and saturated Na$_2$CO$_3$ were added and it was stirred for 30 min. the insoluble solid was filtrated off. The mother liquid was neutralized with 5N HCl until PH=1~2. The precipitated solid was collected and washed with H$_2$O and cold ether to provide the desired product.

N-[2-(4'-nitro benzyloxy)-4-nitrophenyl]methanesulfonamide (27b) It is stirred and refluxed in CH$_3$CN for 48 h. Yellow powder, 74%: mp 168-169° C.; $^1$H-NMR (400 MHz, CDCl$_3$) δ8.32 (2H, d, J=8.7 Hz), 7.98 (1H, dd, J=8.9, 2.3 Hz), 7.86 (1H, d, J=2.3 Hz), 7.71 (1H, d, J=8.9 Hz), 7.63 (1H, d, J=8.8 Hz), 5.35 (2H, s), 3.16 (3H, s); $^{13}$C NMR (100 MHz, CDCl$_3$) δ148.73, 146.40, 143.96, 141.70, 133.38, 128.97, 124.77, 118.88, 116.90, 107.70, 70.74, 40.95; HRMS calculated for C$_{14}$H$_{13}$N$_3$NaO$_7$S (M+Na)$^+$ 390.0372, found 390.0364.

N-[2-(β-naphthylmethoxy) 4-nitrophenyl]methanesulfonamide (28b) It is stirred in 3N NaOH aq solution at 85-90° C. over night. Pale yellow solid, 95%: mp 239-243° C. (decomposed); $^1$H-NMR (400 MHz, DMSO-d$_6$) δ8.07 (1H, s), 7.92 (3H, m), 7.83 (1H, s), 7.80 (1H, d, J=2.5 Hz), 7.68 (1H, dd, J=8.4, 1.5 Hz), 7.53 (2H, m), 7.45 (1H, d, J=8.4 Hz), 5.44 (2H, s), 3.01 (3H, s); $^{13}$C NMR (100 MHz, DMSO-d$_6$) δ149.72, 135.00, 133.60, 133.48, 128.91, 128.67, 128.51, 127.40, 127.23, 127.06, 126.72, 119.89, 118.77, 109.17, 71.30, 41.54; HRMS calculated for C$_{18}$H$_{16}$N$_2$NaO$_5$S (M+Na)$^+$ 395.0678, found 395.0685.

N-[2-(2'-phenyl benzyloxy)-4-nitrophenyl]methanesulfonamide (29b) It is stirred in 3N NaOH aq solution at 85-90° C. over night. Yellow solid, 94%: mp 116-119° C.; $^1$H-NMR (400 MHz, DMSO-d$_6$) δ7.65 (2H, dd, J=9.1, 3.0 Hz), 7.51 (2H, d, J=7.0 Hz), 7.31 (7H, m), 7.19 (1H, d, J=9.2 Hz), 4.93 (2H, s), 2.73 (3H, s); $^{13}$C NMR (100 MHz, DMSO-d$_6$) δ149.33, 142.49, 140.87, 135.02, 130.63, 130.52, 130.02, 129.10, 129.00, 128.33, 128.21, 120.32, 116.59, 109.09, 69.14, 41.27; HRMS calculated for C$_{20}$H$_{18}$N$_2$NaO$_5$S (M+Na)$^+$ 421.0834, found 421.0840.

N-methyl-N-[2-(4'-nitro benzyloxy)-4-nitrophenyl]methanesulfonamide (27c) Compound 2b (0.11 g, 0.3 mmol) was dissolved in 4 mL dry DMF and K$_2$CO$_3$ powder (0.083 g, 0.6 mmol) was added. The mixture was stirred at room temperature for 10 minutes and iodomethane (0.085 g, 0.6 mmol) was added, then it was stirring at 45-50° C. over night. Then the mixture was taken up with 7 mL of water and 2 mL of Na$_2$CO$_3$ aq solution. The precipitated solid was collected by filtration and washed with water and cold ether to afford white solid 108 mg (94%): mp 209-211° C.; $^1$H-NMR (400 MHz, DMSO-d$_6$) δ8.29 (2H, d, J=8.7 Hz), 8.00 (1H, d, J=2.3 Hz), 7.89 (1H, dd, J=8.7, 2.4 Hz), 7.80 (2H, d, J=8.6 Hz), 7.64 (1H, d, J=8.7 Hz), 5.53 (2H, s), 3.22 (3H, s), 3.05 (3H, s); $^{13}$C NMR (100 MHz, DMSO-d$_6$) δ155.92, 148.23, 148.12, 144.44, 136.65, 132.64, 129.43, 124.65, 117.12, 109.49, 70.33, 39.17, 38.12. HRMS calculated for C$_{15}$H$_{15}$N$_3$NaO$_7$S (M+Na)$^+$ 404.0528, found 404.0501. Anal. (C$_{15}$H$_{15}$N$_3$O$_7$S) C, H, N.

General procedure for the preparation of 28c-39c Methanesulfonamide compound (0.5 mmol) was dissolved in 3 mL dry DMF and NaH powder (15.2 mg 95%, 0.6 mmol, 1.2 eq) was added. The mixture was stirred at room temperature for 10 minutes and iodomethane (0.6 mmol, 1.2 eq) was added; the stirring was kept for 2 h at room temperature. Then the mixture was taken up with 7 mL of water and 2 mL of Na$_2$CO$_3$ aq solution. The precipitated solid was collected by filtration and washed with water and cold ether to afford the desired product, then it was recrystallized from ethyl acetate/hexane.

N-methyl-N-[2-(β-naphthylmethoxy) 4-nitrophenyl]methanesulfonamide (28c) Pale yellow solid, 96%: mp 119-121° C.; $^1$H-NMR (400 MHz, CDCl$_3$) δ8.02 (1H, d, J=2.4 Hz), 7.96 (1H, s), 7.89 (4H, m), 7.55 (4H, m), 5.39 (2H, s), 3.30 (3H, s), 2.84 (3H, s); $^{13}$C NMR (100 MHz, CDCl$_3$) δ155.73, 148.43, 135.84, 133.79, 133.58, 133.06, 132.30, 129.44, 128.45, 128.27, 128.08, 127.29, 127.23, 125.80, 117.03, 108.52, 72.16, 38.98, 37.96. HRMS calculated for C$_{19}$H$_{18}$N$_2$NaO$_5$S (M+Na)$^+$ 409.0834, found 409.0825. Anal. (C$_{19}$H$_{18}$N$_2$O$_5$S) C, H, N.

N-methyl-N-[2-(2'-phenyl benzyloxy)-4-nitrophenyl]methanesulfonamide (29c) Pale yellow solid, 82%: mp 128-129° C.; $^1$H-NMR (400 MHz, CDCl$_3$) δ7.84 (1H, dd, J=8.6, 2.4 Hz), 7.66 (1H, d, J=2.4 Hz), 7.37 (10H, m), 5.19 (2H, s), 3.24 (3H, s), 2.83 (3H, s); $^{13}$C NMR (100 MHz, CDCl$_3$) δ55.51, 148.34, 142.74, 140.20, 132.81, 132.31, 131.05, 129.88, 129.55, 129.41, 129.04, 128.38, 128.24, 116.88, 108.59, 69.76, 38.94, 38.00. HRMS calculated for C$_{21}$H$_{20}$N$_2$NaO$_5$S (M+Na)$^+$ 435.0991, found 435.0996. Anal. (C$_{21}$H$_{20}$N$_2$O$_5$S) C, H, N.

General procedure for the preparation of 30a-39a K$_2$CO$_3$ (0.69 g, 5 mmol) and aryl halide (5 mmol, 1.0 eq) were successively added to a solution of 2-amino-5-nitrophenol (0.77 g, 5 mmol) in DMF or acetone (10 ml) and the mixture was Stirred at room temperature or 75-80° C. from 3 h to overnight. After being cooled, 20 mL H$_2$O and 5 mL saturated aqueous Na$_2$CO$_3$ was added to the mixture and the precipitated solid was collected by filtration and washed with H$_2$O and cold ethyl ether. If the product precipitated as oil, the aqueous phase was extracted with CH$_2$Cl$_2$. The organic solution was washed with saturated aqueous Na$_2$CO$_3$ solution and H$_2$O, dried over anhydrous MgSO$_4$, and concentrated. The residue was chromatographed on silica gel [AcOEt-hexane (1:5)] to afford desired compounds.

2-(4'-methyl benzyloxy)-4-nitroaniline (30a) 4-methyl benzyl chloride was used and it was stirred in DMF at 75-80° C. for 3 h. Yellow solid, 85%: mp 149-150° C.; $^1$H-NMR (400 MHz, CDCl$_3$) δ7.83 (1H, dd, J=8.7, 2.3 Hz), 7.79 (1H, d, J=2.3 Hz), 7.35 (2H, d, J=8.0 Hz), 7.24 (2H, d, J=7.8 Hz), 6.66 (1H, d, J=8.7 Hz), 5.12 (2H, s), 4.61 (2H, s), 2.41 (3H, s); $^{13}$C NMR (100 MHz, CDCl$_3$) δ144.97, 143.93, 138.97, 138.87, 133.11, 129.86, 128.49, 119.75, 112.31, 107.63, 71.23, 21.67.

2-(4'-methoxyl benzyloxy)-4-nitroaniline (31a) 4-methoxyl benzyl chloride was used and it was stirred in DMF at 75-80° C. for 3 h. Yellow solid, 89%: mp 131-132° C.; $^1$H-NMR (400 MHz, CDCl$_3$) δ7.83 (1H, dd, J=8.7, 2.3 Hz), 7.79 (1H, d, J=2.3 Hz), 7.38 (2H, d, J=8.7 Hz), 6.95 (2H, d, J=8.7 Hz), 6.65 (1H, d, J=8.7 Hz), 5.09 (2H, s), 4.60 (2H, s), 3.85 (3H, s); $^{13}$C NMR (100 MHz, CDCl$_3$) δ160.25, 144.96, 143.94, 138.96, 130.14, 128.17, 119.74, 114.54, 112.30, 107.65, 71.10, 55.75.

2-(4'-isopropyl benzyloxy)-4-nitroaniline (32a) 4-isopropyl benzyl chloride was used and it was stirred in DMF at 75-80° C. for 3 h. Yellow solid, 91%: mp 99-101° C.; $^1$H-NMR (400 MHz, CDCl$_3$) δ7.84 (1H, dd, J=8.7, 2.4 Hz), 7.80 (1H, d, J=2.4 Hz), 7.39 (2H, d, J=8.1 Hz), 7.30 (2H, d, J=8.0 Hz), 6.66 (1H, d, J=8.7 Hz), 5.13 (2H, s), 4.60 (2H, s), 2.95 (1H, m), 1.29 (6H, d, J=6.9 Hz); $^{13}$C NMR (100 MHz, CDCl$_3$) δ149.84, 145.04, 143.88, 133.48, 128.57, 127.25, 119.74, 112.30, 107.54, 71.23, 34.34, 24.38.

2-(4'-fluoro benzyloxy)-4-nitroaniline (33a) 4-fluoro benzyl chloride was used and it was stirred in DMF at room temperature over night. Yellow solid, 98%: mp 125-127° C.; $^1$H-NMR (400 MHz, CDCl$_3$) δ7.84 (1H, dd, J=8.7, 2.3 Hz), 7.78 (1H, d, J=2.3 Hz), 7.43 (2H, m), 7.08 (2H, m), 6.73 (1H, d, J=8.7 Hz), 5.15 (2H, s), 5.05 (2H, br); $^{13}$C NMR (100 MHz, CDCl$_3$) δ164.43, 161.97, 145.28, 131.83, 130.32, 130.24, 119.70, 116.26, 116.04, 113.38, 107.69, 70.66.

2-(4'-chloro benzyloxy)-4-nitroaniline (34a) 4-chloro benzyl chloride was used and it was stirred in DMF at room temperature over night. Yellow solid, 90%: mp 128-130° C.; $^1$H-NMR (400 MHz, CDCl$_3$) δ7.84 (1H, dd, J=8.7, 2.3 Hz), 7.75 (1H, d, J=2.3 Hz), 7.41 (4H, s), 6.68 (1H, d, J=8.7 Hz), 5.13 (2H, s), 4.61 (2H, s); $^{13}$C NMR (100 MHz, CDCl$_3$) δ144.64, 143.84, 138.95, 134.86, 134.60, 129.64, 129.41, 119.97, 112.50, 107.64, 70.49.

2-(4'-bromo benzyloxy)-4-nitroaniline (35a) 4-bromo benzyl bromide was used and it was stirred in DMF at room temperature over night. Yellow solid, 66%: mp 131-133° C.; $^1$H-NMR (400 MHz, CDCl$_3$) δ7.83 (1H, dd, J=8.7, 2.3 Hz), 7.75 (1H, d, J=2.3 Hz), 7.55 (2H, d, J=8.4 Hz), 7.33 (2H, d, J=8.5 Hz), 6.67 (1H, d, J=8.7 Hz), 5.12 (2H, s), 4.62 (2H, s); $^{13}$C NMR (100 MHz, CDCl$_3$) δ144.62, 143.84, 138.94, 135.12, 132.36, 129.92, 129.09, 122.99, 119.98, 112.51, 107.63, 70.51.

2-(4'-phenyl benzyloxy)-4-nitroaniline (36a) 4-phenyl benzyl chloride was used and it was stirred in DMF at room temperature for 48 h. Yellow solid, 82%: mp 151-153° C.; $^1$H-NMR (400 MHz, CDCl$_3$) δ67.84 (1H, dd, J=8.7, 2.3 Hz), 7.82 (1H, d, J=2.3 Hz), 7.61 (4H, m), 7.54 (2H, d, J=8.4 Hz), 7.46 (2H, m), 7.40 (1H, m), 6.74 (1H, d, J=8.6 Hz), 5.21 (2H, s), 5.01 (2H, br); $^{13}$C NMR (100 MHz, CDCl$_3$) δ145.33, 141.94, 140.88, 139.56, 134.99, 129.28, 128.84, 128.53, 128.01, 127.90, 119.69, 113.11, 107.70, 71.09.

2-phenylethoxy-4-nitroaniline (37a) Phenylethyl bromide was used and it was refluxed in DMF for 48 h. Yellow solid, 28%: mp 83-85° C.; $^1$H-NMR (400 MHz, CDCl$_3$) δ7.81 (1H, dd, J=8.7, 2.4 Hz), 7.68 (1H, d, J=2.4 Hz), 7.29 (5H, m), 6.62 (1H, d, J=8.7 Hz), 4.48 (2H, br), 4.31 (2H, dd, J=6.8, 6.8 Hz), 3.17 (2H, dd, J=6.7, 6.7 Hz); $^{13}$C NMR (100 MHz, CDCl$_3$) δ144.92, 143.82, 139.04, 138.12, 129.30, 129.08, 127.18, 119.65, 112.30, 107.39, 69.74, 35.96.

2-(α-naphthylmethoxy)-4-nitroaniline (38a) α-Naphthylmethyl chloride was used and it was stirred in DMF at room temperature over night. Yellow solid, 98%: mp 197-199° C.; $^1$H-NMR (400 MHz, DMSO-d$_6$) δ8.19 (1H, d, J=8.0 Hz), 7.94 (2H, m), 7.90 (1H, d, J=2.4 Hz), 7.76 (2H, m), 7.52 (3H, m), 6.70 (1H, d, J=8.9 Hz), 6.39 (2H, br), 5.70 (2H, s); $^{13}$C NMR (100 MHz, DMSO-d$_6$) δ147.08, 144.24, 136.39, 134.15, 132.85, 131.91, 129.57, 129.32, 127.41, 127.35, 126.88, 126.27, 124.81, 120.78, 112.06, 108.25, 69.17.

2-(3',6'-dimethyl benzyloxy)-4-nitroaniline (39a) 3,6-dimethyl benzyl chloride was used and it was stirred in DMF at 75-80° C. for 3 h. Yellow solid, 93%: mp 160-161° C.; $^1$H-NMR (400 MHz, DMSO-d$_6$) δ7.75 (1H, dd, J=8.7, 2.2 Hz), 7.73 (1H, d, J=2.3 Hz), 7.32 (1H, s), 7.11 (1H, d, J=7.7 Hz), 7.07 (1H, d, J=7.7 Hz), 6.70 (1H, dd, J=8.7, 1.0 Hz), 6.39 (2H, br), 5.15 (2H, s), 2.30 (3H, s), 2.29 (3H, s); $^{13}$C NMR (100 MHz, DMSO-d$_6$) δ147.05, 144.37, 136.36, 135.57, 135.00, 134.41, 130.94, 130.14, 129.54, 120.68, 112.00 107.83, 69.45, 21.44, 18.93.

General procedure for the preparation of compounds 30b-39b NaH (95% powder, 0.265 g, 10.5 mmol, 3.5 eq) was added to a solution of aryl instituted 2-amino-5-nitrophenol (3.0 mmol) in anhydrous DMF (8 ml) at room temperature. After being stirred at the same temperature for 30 min, MsCl (1.031 g, 9.0 mmol, 3 eq) was added to the mixture and the stirring was continued overnight at room temperature. H$_2$O was added to the mixture, then it was neutralized with 5N HCl until pH=1~2. The intermediate precipitated as a yellow solid. It was collected by filtration and washed with H$_2$O, which was used to the next reaction without further purification. The intermediate was added to a 3N NaOH aq solution and was stirred at 80~90° C. overnight. After cool down, then it was neutralized with 5N HCl until PH=1~2. The precipitated solid was collected and washed with H$_2$O and cold ether to provide the desired product, then it was recrystallized from ethyl acetate/hexane.

N-[2-(4'-methyl benzyloxy)-4-nitrophenyl]methanesulfonamide (30b) Pale yellow solid, 87%: mp 151-152° C.; $^1$H-NMR (400 MHz, CDCl$_3$) δ7.93 (1H, dd, J=8.9, 2.4 Hz), 7.91 (1H, d, J=2.3 Hz), 7.67 (1H, d, J=8.8 Hz), 7.32 (2H, d, J=8.0 Hz), 7.25 (2H, d, J=7.9; H), 5.19 (2H, s), 3.08 (3H, s), 2.41 (3H, s); $^{13}$C NMR (100 MHz, CDCl$_3$) δ147.20, 144.15, 133.42, 131.73, 130.17, 128.77, 118.19, 116.96, 107.91, 72.25, 40.59, 21.68; HRMS calculated for C$_{15}$H$_{16}$N$_2$NaO$_5$S (M+Na)$^+$ 359.0678, found 359.0670.

N-[2-(4'-methoxyl benzyloxy)-4-nitrophenyl]methanesulfonamide (31b) Pale yellow solid, 86%: mp 150-152° C.; $^1$H-NMR (400 MHz, CDCl$_3$) δ7.93 (1H, dd, J=8.8, 2.4 Hz), 7.91 (1H, d, J=2.2 Hz), 7.67 (1H, d, J=8.8 Hz), 7.36 (2H, d, J=8.6 Hz), 6.97 (2H, d, J=8.6 Hz), 5.16 (2H, s), 3.86 (3H, s), 3.08 (3H, s); $^{13}$C NMR (100 MHz, CDCl$_3$) δ160.72, 147.19, 144.13, 133.42, 130.50, 126.73, 118.16, 116.91, 114.87, 107.90, 72.12, 55.80, 40.60; HRMS calculated for C$_{15}$H$_{16}$N$_2$NaO$_6$S (M+Na)$^+$ 375.0627, found 375.0625.

N-[2-(4'-isopropyl benzyloxy)-4-nitrophenyl]methanesulfonamide (32b) Pale yellow solid, 86%: mp 171-172° C.; $^1$H-NMR (400 MHz, CDCl$_3$) δ7.95 (1H, dd, J=8.8, 2.5 Hz), 7.92 (1H, d, J=2.4 Hz), 7.68 (1H, d, J=8.8 Hz), 7.35 (2H, d, J=8.2 Hz), 7.31 (2H, d, J=8.3 Hz), 7.25 (1H, br), 5.18 (2H, s), 3.08 (3H, s), 2.96 (1H, m), 1.30 (6H, d, J=6.9 Hz); $^{13}$C NMR (100 MHz, CDCl$_3$) δ150.63, 147.25, 144.18, 133.39, 132.02, 128.97, 127.60, 118.20, 116.92, 107.84, 72.30, 40.58, 34.39, 24.33; HRMS calculated for C$_{17}$H$_{20}$N$_2$NaO$_5$S (M+Na)$^+$ 387.0991, found 387.0981.

N-[2-(4'-fluoro benzyloxy)-4-nitrophenyl]methanesulfonamide (33b) Yellow solid, 83%: mp 162-164° C.; $^1$H-NMR (400 MHz, CDCl$_3$) δ7.95 (1H, dd, J=8.9, 2.4 Hz), 7.89 (1H, d, J=2.4 Hz), 7.68 (1H, d, J=8.9 Hz), 7.41 (2H, m), 7.25 (1H, br), 7.13 (2H, m), 5.19 (2H, s), 3.11 (3H, s); $^{13}$C NMR (100 MHz, CDCl$_3$) δ164.79, 162.32, 146.93, 144.06, 133.38, 130.76, 130.68, 130.60, 130.56, 118.38, 116.86, 116.67, 116.46, 107.76, 71.54, 40.71; HRMS calculated for C$_{14}$H$_{13}$FN$_2$NaO$_5$S (M+Na)$^+$ 363.0427, found 363.0417.

N-[2-(4'-chloro benzyloxy)-4-nitrophenyl]methanesulfonamide (34b) Pale yellow solid, 90%: mp 171-173° C.; $^1$H-NMR (400 MHz, CDCl$_3$) δ7.94 (1H, dd, J=8.9, 2.4 Hz), 7.87 (1H, d, J=2.3 Hz), 7.68 (1H, d, J=8.9 Hz), 7.43 (2H, d, J=8.5 Hz), 7.37 (2H, d, J=8.5 Hz), 5.20 (2H, s), 3.11 (3H, s); $^{13}$C NMR (100 MHz, CDCl$_3$) δ146.85, 144.04, 135.62, 133.38, 133.19, 130.01, 129.76, 118.46, 116.89, 107.77, 71.43, 40.74; HRMS calculated for C$_{14}$H$_{13}$ClN$_2$NaO$_5$S (M+Na)$^+$ 379.0131, found 379.0136.

N-[2-(4'-bromo benzyloxy)-4-nitrophenyl]methanesulfonamide (35b) Pale yellow solid, 82%: mp 183-185° C.; $^1$H-NMR (400 MHz, CDCl$_3$) δ7.94 (1H, dd, J=8.9, 2.4 Hz), 7.97 (1H, d, J=2.3 Hz), 7.68 (1H, d, J=8.9 Hz), 7.59 (2H, d, J=8.4 Hz), 7.31 (2H, d, J=8.4 Hz), 5.18 (2H, s), 3.11 (3H, s); $^{13}$C NMR (100 MHz, CDCl$_3$) δ146.81, 144.04, 133.69, 133.38, 132.73, 130.25, 123.78, 118.48, 116.89, 107.78, 71.47, 40.75; HRMS calculated for C$_{14}$H$_{13}$BrN$_2$NaO$_5$S (M+Na)$^+$ 422.9626, found 422.9636.

N-[2-(4'-phenyl benzyloxy)-4-nitrophenyl]methanesulfonamide (36b) Yellow solid, 94%: mp 253-255° C.; $^1$H-NMR (400 MHz, DMSO-d$_6$) δ9.68 (1H, br), 7.87 (1H, s), 7.84 (1H, d, J=2.5 Hz), 7.64 (6H, m), 7.46 (3H, m), 7.36 (1H, m), 5.35 (2H, s), 3.08 (3H, s); $^{13}$C NMR (100 MHz, DMSO-d$_6$) δ149.70, 140.76, 140.61, 136.25, 129.82, 129.43, 128.41, 127.61, 127.56, 118.32, 108.80, 70.89, 41.53; HRMS calculated for C$_{20}$H$_{18}$N$_2$NaO$_5$S (M+Na)$^+$ 421.0834, found 421.0815.

N-(2-phenylethoxy 4-nitrophenyl) methanesulfonamide (37b) Yellow solid, 77%: mp 120-121° C.; $^1$H-NMR (400 MHz, CDCl$_3$) δ7.90 (1H, dd, J=8.9, 2.5 Hz), 7.78 (1H, d, J=2.4Hz), 7.63 (1H, d, J=8.9 Hz), 7.38 (2H, m), 7.29 (3H, m), 7.05 (1H, br), 4.38 (2H, dd, J=6.6, 6.6 Hz), 3.19 (2H, dd, J=6.6, 6.6 Hz), 2.89 (3H, s); $^{13}$C NMR (100 MHz, CDCl$_3$) δ147.40, 144.33, 137.55, 133.23, 129.43, 129.21, 127.52, 118.10, 117.42, 107.43, 70.54, 40.27, 35.76; HRMS calculated for C$_{15}$H$_{16}$N$_2$NaO$_5$S (M+Na)$^+$ 359.0678, found 359.0668. Anal. (C$_{15}$H$_{16}$N$_2$O$_5$S) C, H, N.

N-[2-(α-naphthylmethoxy) 4-nitrophenyl]methanesulfonamide (38b) Pale yellow solid, 83%: mp 193-195° C.; $^1$H-NMR (400 MHz, CDCl$_3$) δ8.09 (1H, d, J=2.4 Hz), 7.96 (4H, m), 7.69 (1H, d, J=8.9 Hz), 7.58 (3H, m), 7.53 (1H, J=8.1 Hz), 7.14 (1H, br), 5.66 (2H, s), 2.90 (3H, s); $^{13}$C NMR (100 MHz, CDCl$_3$) δ147.24, 144.24, 134.39, 133.62, 132.03, 130.81, 130.23, 129.58, 128.62, 127.58, 126.83, 125.71, 123.37, 118.44, 117.33, 108.20, 71.07, 40.35; HRMS calculated for C$_{18}$H$_{16}$N$_2$NaO$_5$S (M+Na)$^+$ 395.0678, found 395.0686.

N-[2-(3',6'-dimethyl benzyloxy)-4-nitrophenyl]methanesulfonamide (39b) Pale yellow solid, 93%: mp 178-179° C.; $^1$H-NMR (400 MHz, DMSO-d$_6$) δ7.95 (1H, d, J=2.5 Hz), 7.88 (1H, dd, J=8.9, 2.5 Hz), 7.55 (1H, d, J=8.9 Hz), 7.32 (1H, s), 7.14 (1H, d, J=7.7 Hz), 7.08 (1H, d, J=7.6 Hz), 5.25 (2H, s), 3.10 (3H, s), 2.32 (3H, s), 2.28 (3H, s); $^{13}$C NMR (100 MHz, DMSO-d$_6$) δ150.09, 144.19, 135.59, 134.80, 134.47, 131.01, 130.73, 129.85, 121.28, 117.81, 108.61, 70.30, 41.61, 21.45, 18.97; HRMS calculated for C$_{16}$H$_{18}$N$_2$NaO$_5$S (M+Na)$^+$ 373.0834, found 373.0829.

Preparation of 30c-39c with General Procedures:

N-methyl-N-[2-(4'-methyl benzyloxy)-4-nitrophenyl]methanesulfonamide (30c) Yellow solid, 87%: mp 96-98° C.; $^1$H-NMR (400 MHz, CDCl$_3$) δ7.95 (1H, d, J=2.4 Hz), 7.88 (1H, dd, J=8.6, 2.4 Hz), 7.55 (1H, d, J=8.6 Hz), 7.33 (2H, d, J=8.0 Hz), 7.25 (2H, d, J=7.8 Hz), 5.18 (2H, s), 3.27 (3H, s), 2.83 (3H, s), 2.41 (3H, s); $^{13}$C NMR (100 MHz, CDCl$_3$) δ155.72, 148.42, 139.48, 135.73, 133.14, 131.93, 130.10, 128.73, 116.86, 108.46, 71.89, 38.90, 37.90, 21.69; HRMS calculated for C$_{16}$H$_{18}$N$_2$NaO$_5$S (M+Na)$^+$ 373.0834, found 373.0825. Anal. (C$_{16}$H$_{18}$N$_2$O$_5$S) C, H, N.

N-methyl-N-[2-(4'-methoxyl benzyloxy)-4-nitrophenyl]methanesulfonamide (31c) Pale yellow solid, 92%: mp 108-109° C.; $^1$H-NMR (400 MHz, CDCl$_3$) δ7.95 (1H, d, J=2.5 Hz), 7.87 (1H, dd, J=8.6, 2.5 Hz), 7.54 (1H, d, J=8.6 Hz), 7.37 (2H, d, J=8.6 Hz), 6.96 (2H, d, J=8.7 Hz), 5.15 (2H, s), 3.86 (3H, s), 3.25 (3H, s), 2.81 (3H, s); $^{13}$C NMR (100 MHz, CDCl$_3$) δ160.58, 155.70, 148.39, 135.78, 133.05, 130.42, 126.95, 116.83, 114.76, 108.44, 71.73, 55.75, 38.88, 37.88; HRMS calculated for C$_{16}$H$_{18}$N$_2$NaO$_6$S (M+Na)$^+$ 389.0783, found 389.0774.

N-methyl-N-[2-(4'-isopropyl benzyloxy)-4-nitrophenyl] methanesulfonamide (32c) Yellow solid, 85%: mp 83-85° C.; $^1$H-NMR (400 MHz, CDCl$_3$) δ7.96 (1H, d, J=2.4 Hz), 7.88 (1H, dd, J=8.6, 2.4 Hz), 7.56 (1H, d, J=8.6 Hz), 7.37 (2H, d, J=8.1 Hz), 7.30 (2H, d, J=8.1 Hz), 5.19 (2H, s), 3.28 (3H, s), 2.95 (1H, m), 2.83 (3H, s), 1.29 (6H, d, J=6.9 Hz); $^{13}$C NMR (100 MHz, CDCl$_3$) δ155.74, 150.40, 148.43, 135.72, 133.16, 132.28, 128.70, 127.49, 116.87, 108.48, 71.87, 38.89, 37.93, 34.32, 24.32; HRMS calculated for C$_{18}$H$_{22}$N$_2$NaO$_5$S (M+Na)$^+$ 401.1147, found 401.1143.

N-methyl-N-[2-(4'-fluoro benzyloxy)-4-nitrophenyl] methanesulfonamide (33c) Pale yellow solid, 92%: mp 168-169° C.; $^1$H-NMR (400 MHz, CDCl$_3$) δ7.94 (1H, d, J=2.4 Hz), 7.90 (1H, dd, J=8.4, 2.4 Hz), 7.55 (1H, d, J=8.6 Hz), 7.44 (2H, m), 7.13 (2H, m), 5.20 (2H, s), 3.27 (3H, s), 2.84 (3H, s); $^{13}$C NMR (100 MHz, CDCl$_3$) δ164.67, 162.20, 155.57, 148.36, 135.86, 132.87, 130.89, 130.86, 130.63, 130.55, 117.10, 116.62, 116.41, 108.46, 71.24, 38.97, 37.93; HRMS calculated for C$_{15}$H$_{15}$FN$_2$NaO$_5$S (M+Na)$^+$ 377.0583, found 377.0586. Anal. (C$_{15}$H$_{15}$FN$_2$O$_5$S) C, H, N.

N-methyl-N-[2-(4'-chloro benzyloxy)-4-nitrophenyl] methanesulfonamide (34c) Pale yellow solid, 93%: mp 168-170° C.; $^1$H-NMR (400 MHz, CDCl$_3$) δ7.90 (2H, m), 7.55 (1H, m), 7.40 (4H, m), 5.20 (2H, s), 3.27 (3H, s), 2.86 (3H, s); $^{13}$C NMR (100 MHz, CDCl$_3$) δ155.54, 148.36, 135.85, 135.49, 133.48, 132.87, 129.91, 129.72, 117.17, 108.48, 71.15, 39.03, 37.95; HRMS calculated for C$_{15}$H$_{15}$ClN$_2$NaO$_5$S (M+Na)$^+$ 393.0288, found 393.0268.

N-methyl-N-[2-(4'-bromo benzyloxy)-4-nitrophenyl] methanesulfonamide (35c) Pale yellow solid, 90%: mp 151-152° C.; $^1$H-NMR (400 MHz, CDCl$_3$) δ7.90 (2H, m), 7.55 (3H, m), 7.34 (2H, d, J=8.3 Hz), 5.19 (2H, s), 3.28 (3H, s), 2.86 (3H, s); $^{13}$C NMR (100 MHz, CDCl$_3$) δ155.52, 148.36, 135.86, 133.99, 132.87, 132.68, 130.15, 123.63, 117.19, 108.48, 71.18, 39.05, 37.96; HRMS calculated for C$_{15}$H$_{15}$BrN$_2$NaO$_5$S (M+Na)$^+$ 436.9783, found 436.9791.

N-methyl-N-[2-(4'-phenyl benzyloxy)-4-nitrophenyl] methanesulfonamide (36c) Pale yellow solid, 94%: mp 152-153° C.; $^1$H-NMR (400 MHz, CDCl$_3$) δ7.98 (1H, d, J=2.3 Hz), 7.90 (1H, dd, J=8.6, 2.3 Hz), 7.68 (2H, d, J=8.1 Hz), 7.63 (2H, dd, J=7.8, 1.4 Hz), 7.48 (5H, m), 7.41 (1H, d, J=7.4 Hz), 5.28 (2H, s), 3.31 (3H, s), 2.88 (3H, s); $^{13}$C NMR (100 MHz, CDCl$_3$) δ155.70, 148.42, 142.42, 140.56, 135.80, 133.87, 133.08, 129.35, 129.05, 128.20, 128.12, 127.52, 117.02, 108.53, 71.71, 39.00, 37.97; HRMS calculated for C$_{21}$H$_{20}$N$_2$NaO$_5$S (M+Na)$^+$ 435.0991, found 435.0985.

N-methyl-N-(2-phenylethoxy 4-nitrophenyl) methanesulfonamide (37c) Yellow solid, 93%: mp 126-128° C.; $^1$H-NMR (400 MHz, CDCl$_3$) δ7.85 (2H, m), 7.52 (1H, m), 7.35 (2H, m), 7.30 (2H, m), 4.45 (2H, dd, J=6.5, 6.5 Hz), 3.21 (2H, dd, J=6.4, 6.4 Hz), 3.13 (3H, s), 2.63 (3H, s); $^{13}$C NMR (100 MHz, CDCl$_3$) δ155.73, 148.45, 137.51, 135.20, 133.53, 129.32, 129.08, 127.55, 116.73, 108.00, 69.83, 38.34, 37.60, 35.76; HRMS calculated for C$_{16}$H$_{18}$N$_2$NaO$_5$S (M+Na)$^+$ 373.0834, found 373.0829.

N-methyl-N-[2-(α-naphthylmethoxy) 4-nitrophenyl] methanesulfonamide (38c) Pale yellow solid, 94%: mp 163-165° C.; $^1$H-NMR (400 MHz, CDCl$_3$) δ8.12 (1H, d, J=2.4 Hz), 8.01 (1H, dd, J=6.2, 3.5 Hz), 7.92 (3H, m), 7.51 (5H, m), 5.65 (2H, s), 3.13 (3H, s), 2.55 (3H, s); $^{13}$C NMR (100 MHz, CDCl$_3$) δ155.79, 148.46, 135.89, 134.28, 133.22, 131.88, 130.70, 130.57, 129.46, 128.38, 127.32, 126.84, 125.77, 123.74, 117.07, 108.37, 71.37, 38.62, 37.96; HRMS calculated for $C_{19}H_{18}N_2NaO_5S$ $(M+Na)^+$ 409.0834, found 409.0842.

N-methyl-N-[2-(3',6'-dimethyl benzyloxy)-4-nitrophenyl] methanesulfonamide (39c) Yellow solid, 87%: mp 137-139° C.; $^1$H-NMR (400 MHz, DMSO-$d_6$) δ8.05 (1H, d, J=2.5 Hz), 7.86 (1H, dd, J=8.6, 2.5 Hz), 7.61 (1H, d, J=8.6 Hz), 7.30 (1H, s), 7.14 (1H, d, J=7.7 Hz), 7.11 (1H, d, J=7.6 Hz), 5.28 (2H, s), 3.15 (3H, s), 2.94 (3H, s), 2.32 (3H, s), 2.28 (3H, s); $^{13}$C NMR (100 MHz, DMSO-$d_6$) δ156.34, 148.19, 136.80, 135.72, 134.52, 134.36, 132.01, 131.06, 130.56, 129.97, 116.75, 109.33, 70.17, 39.04, 38.07, 21.44, 18.84; HRMS calculated for $C_{17}H_{20}N_2NaO_5S$ $(M+Na)^+$ 387.0991, found 387.0983.

Biological Study

Cell Culture. AR and SK-BR-3 cells were obtained from ATCC (Rockville, Md.). SK-BR-3 cells were maintained in phenol red-free custom media (MEM, Earle's salts, 1.5× amino acids, 2× non-essential amino acids, L-glutamine, 1.5× vitamins, Gibco BRL) supplemented with 10% fetal bovine serum (FBS), 2 mM L-glutamine and 20 mg/L gentamycin. JAR cells were maintained in RPMI 1640 medium with 2 mM L-glutamine adjusted to contain 1.5 g/L sodium bicarbonate, 4.5 g/L glucose, 10 mM HEPES, and 1.0 mM sodium pyruvate, 90%; FBS, 10%. Fetal bovine serum was heat inactivated for 30 min in a 56° C. water bath before use. Cell cultures were grown at 37° C., in a humidified atmosphere of 5% $CO_2$ in a Hereaus $CO_2$ incubator. For all experiments, cells were plated in 6 well plates and grown to subconfluency. Before treatment, the media was changed to a defined one containing DMEM/F12 media (Sigma) with 1.0 mg/mL human albumin (OSU Hospital Pharmacy), 5.0 mg/L human transferin and 5.0 mg/L bovine insulin.

Tritiated water-release assay in JAR and SK-BR-3 cell lines. Measurement of aromatase enzyme activity was based on the tritium water release assay. Cells in six well plates were treated with 0.1% DMSO (control), and inhibitors at the indicated concentrations. After 24 hours, the cells were incubated 3 hours (SK-BR-3 cells) or 1 hour (JAR cells) with fresh media along with 100 nM [1β-$^3$H]-androst-4-ene-3,17-dione (1 μCi). Subsequently, the reaction mixture was removed, and proteins were precipitated using 10% trichloroacetic acid at 42° C. for 20 min. After a brief centrifugation, the media was extracted three times with an equal amount of chloroform to remove remaining substrate and further treated with dextran-treated charcoal. After centrifugation, a 250-μl aliquot containing the product was counted in 5 ml of liquid scintillation mixture. Results were corrected for blanks and for the cell contents of culture flasks, and results were expressed as picomoles of $^3H_2O$ formed per hour incubation time per million live cells (pmol/h/$10^6$ cells). To determine the amount of cells in each flask, the cells were lysed and analyzed using the diphenylamine DNA assay adapted to a 96-well plate. $IC_{50}$ sigmoidal dose-response data were analyzed with Microsoft Excel and the Graphpad Prism (Version 3.0) program.

Diphenylamine DNA Assay To determine the amount of viable cells in each flask, the cells were lysed with 0.5N NaOH aqueous solution and analyzed using the diphenylamine DNA assay adapted to a 96-well plate. DNA standards (0-30 μg) were prepared using double-stranded DNA reconstituted in PBS and added in triplicates directly to the wells. A uniform cell suspension was prepared from the 6 well plate in 300 μl 0.5N NaOH aqueous solution, and 60 μl of the unknown samples were added in triplicates to separate wells. A solution of 0.16% acetaldehyde in water was prepared and mixed at a 1:5 ratio with perchloric acid (20% vol/vol). This solution (60 μl) was added to each well along with 100 μl of a 4% diphenylamine solution in glacial acetic acid. The plates were incubated at 37° C. for 24 hours. After centrifugation, 100 μl supernatant of each well was transferred to a new 96 well plate, and the $OD_{595}$ was measured using a microplater reader. The DNA concentration was determined by extrapolation to the standard curve and the amount of cells/well was calculated using the equation: 1 cell≈7 pg DNA.

RNA extraction. Total RNA was isolated using the TRIzol reagent according to the manufacturer's protocol. Total RNA pellets were dissolved in DNase, RNase-free water and quantitated using a spectrophotometer. The quality of RNA samples was determined by electrophoresis through agarose gels and staining with ethidium bromide; the 18S and 28S rRNA bands were visualized under ultraviolet light.

cDNA synthesis. Isolated total RNA (2 μg) was treated with DNase I Amplification grade, according to the recommended protocol to eliminate any DNA before reverse transcription. Treated total RNA was denatured at 65° C. for 5 min in the presence of 2.5 ng/μL random hexamers and 0.5 mM dNTP mix. The samples were snap-cooled on ice and centrifuged briefly. Complementary DNA (cDNA) was synthesized using Superscript II reverse transcriptase according to the recommended protocol. Briefly, the reactions were conducted in the presence of 1× First-Strand Buffer and 20 mM DTT at 42° C. for 50 min and consequently inactivated at 70° C. for 15 min. The cDNA generated was used as a template in real-time PCR reactions.

Real-time PCR. Real-time PCR was performed using the Opticon™ 2 system from MJ Research (Waltham, Mass.). For the CYP19 total gene the PCR reaction mixture consisted of Taqman® Universal PCR Master Mix (Applied Biosystems), 600 nM of CYP19 primer (sense: 5'-TGT CTC TTT GTT CTT CAT GCT ATT TCT C-3' (SEQ ID NO: 1); antisense: 5'-TCA CCA ATA ACA GTC TGG ATT TCC-3') (SEQ ID NO: 2); 250 nM Taqman probe (6FAM 5'-TGC AAA GCA CCC TAA TGT TGA AGA GGC AAT-3'TAMRA) (SEQ ID NO: 3) (Invitrogen), and 2.0 μL of each cDNA sample in a final volume of 20 μL. For the 18S house keeping total gene the PCR reaction mixture consisted of Taqman® Universal PCR Master Mix (Applied Biosystems), 500 nM of 18S primer (sense: 5'-GAG TTC ATA CAG CGG AAC ACT G-3' (SEQ ID NO: 4); antisense: 5'-TTT GCT GGA GAA GAG GGC TG-3') (SEQ ID NO: 5); 50 nM Taqman probe (6FAM 5'-TGC TGG CAC CAG ACT TGC CCT C-3'TAMRA) (SEQ ID NO: 6) (Invitrogen), and 2.0 μl of each cDNA sample in a final volume of 20 μL. The Taqman probes for aromatase and 18S were designed to anneal to a specific sequence of the aromatase and 18S gene correspondingly between the forward and the reverse primers. Cycling conditions were 50° C. for 2 mm and 95° C. for 10 mm, followed by 50 cycles at 95° C. for 15 s and 60° C. for 1 mm.

Cell Viability Analysis. The effect of nimesulides derivatives on SK-BR-3 cell viability was assessed by using the 3-(4,5-dimethylthiazol-2-yl)-2,5-diphenyl-2H-tetrazolium bromide assay in six replicates. Cells were grown in custom media in 96-well, flat-bottomed plates for 24 h, and were exposed to various concentrations of nimesulide derivatives dissolved in DMSO (final concentration ≦0.1%) in define media for different time intervals. Controls received DMSO vehicle at a concentration equal to that in drug-treated cells. The medium was removed, replaced by 200 μl of 0.5 mg/ml of 3-(4,5-dimethylthiazol-2-yl)-2,5-diphenyl-2H-tetrazolium bromide in fresh media, and cells were incubated in the $CO_2$ incubator at 37° C. for 2 h. Supernatants were removed from the wells, and the reduced 3-(4,5-dimethylthiazol-2-yl)-2,5- diphenyl-2H-tetrazolium bromide dye was solubilized in 200 µl/well DMSO. Absorbance at 570 nm was determined on a plate reader.

Analysis of apoptosis. Apoptosis was determined by selective denaturation of DNA in apoptotic cells by formamide and detection of denatured DNA with a monoclonal antibody to single-stranded DNA using an ELISA kit (CHEMICON, Temecula, Calif.). Cells were plated in a 96-well flat bottom plate from $0.5 \times 10^4$ to $1 \times 10^4$ cells/well in custom media. Cells were allowed to adhere to wells overnight. Following incubation, compounds were made up in define media and a 5 µM screen was performed in each cell line with respective compounds in triplicate for 24 hours. Following treatment, the plate was centrifuged at 200×g for 5 min, media was removed followed by the addition of 200 µl of fixative. The plate was incubated for 30 min at 37° C., at which point the fixative was removed and the plate dried for 1-2 hours at room temperature. Fifty microliters of formamide was added to each well following a brief incubation at room temperature for 10 min. The DNA in apoptotic cells was denatured by heating the plate for 10 min, then briefly cooling the plate for 5 min at 4° C. following removal of formamide. The plate was rinsed three times with 200 µl of PBS following one hour incubation at 37° C. with 200 µl of 3% blocking agent. After removal of the blocking agent, 100 µl of antibody mixture were added to each well for 30 min at room temperature. The plate was washed three times with 1× wash buffer using 250 µl of wash buffer/well followed by the addition of 200 µl of ABTS solution added to each well for a 15-60 minute incubation. The reaction was stopped by the addition of 100 µl of a stop solution added to each well and absorbance was measured at 405 nm on a SpectroMax 340 UV PlateReader.

Biological Evaluation Aromatase in the endoplasmic reticulum of cells catalyzes the biosynthesis of estrogen. The regulation of aromatase is complex and different in various tissues, and several tissue-specific promoter regions have been identified upstream from the CYP19 gene. These tissue-specific promoters include promoter PI.1, PI.3, PI.4, PI.6, PI.7, and PII. Promoter PI.1 is the major promoter used in placental tissues and the PII and I.3 promoters are used in the ovary and in breast cancer tissues. Due to the unique organization of tissue-specific promoters, various promoters employ different signaling pathways and different transcription factors. This use of tissue-specific promoters allows for the development of possible selective aromatase expression regulators. Promoter I.1 (mainly used in placenta) is regulated through a protein kinase C-mediated mechanism. Studies from several research groups indicated that promoters II and I.3, which are adenosine 3',5'-cyclic monophosphate (cAMP) regulated promoters, are the major promoters driving aromatase expression in breast cancer and surrounding adipose stromal cells. In addition, alternate exon PII and I.3 were also found to be the major exons in aromatase transcripts in four breast cancer cell lines (MCF-7, T-47D, SK-BR-3, and MDA-MB-231 cells). Therefore, the major promoter used in breast tumors and the four breast cancer cells (i.e., cAMP-stimulated promoters I.3 and II) is different from that placental tissue (i.e., protein kinase C-mediated promoter I.1).

Evaluations of the synthetic compounds were performed in both SK-BR-3 breast cancer cells (which produce aromatase expression from promoter II and I.3 mediated by cAMP) and JAR choriocarcinoma placental cells (which produce aromatase expression from promoter I.1 mediated by protein kinase C). Comparisons of bioactivity between these two cell lines enable us differentiate compounds that can only suppress aromatase activity in breast cancer cells and not suppress aromatase activity in placental cells. Those compounds with differential effects of aromatase activity were further investigated for their potential suppressing CYP19 transcription in breast cancer cells.

The cellular aromatase assays for these compounds were performed in the choriocarcinoma placental JAR cell line and the breast cancer SK-BR-3 cell line according to the modified method of the procedure previously reported by our laboratory. (Diaz-Cruz, E. S.; Shapiro, C. L.; and Brueggemeier, R. W. Cyclooxygenase inhibitors suppress aromatase expression and activity in breast cancer cells. J. Clin. Endocrinol. Metab 2005, 90, 2563-2570; and Su, B.; Diaz-Cruz, E. S.; Landini, S.; and Brueggemeier, R. W. Novel sulfonanilide analogues suppress aromatase expression and activity in breast cancer cells independent of COX-2 inhibition. J. Med. Chem. 2006, 49, 1413-1419; each incorporated herein by reference). These two cell lines, the SK-BR-3 and JAR cells, were used because of their high cellular aromatase enzyme activity and their different regulation of CYP19 expression. Other human breast cancer cell lines express lower levels of aromatase activity. If the compounds decrease aromatase activity effectively in JAR cells, they may decrease aromatase transcription from promoter I 1 by interfering with protein kinase C pathway. If the compounds decrease aromatase activity effectively in SK-BR-3 breast cancer cells, these compounds may decrease aromatase expression from promoter II and I.3 mediated by cAMP. If the compounds decrease aromatase activity in both cells lines, then several alternative mechanisms for these compounds may be involved, including (1) they may directly inhibit aromatase enzyme, (2) they may increase aromatase degradation, or (3) they may decrease aromatase mRNA stability. In addition, the compounds were tested for their general cell cytotoxicity and the ability to induce apoptosis. Compounds only targeting aromatase expression in breast cancer cells and not affecting other cell functions will be the ideal final target compounds.

Figure 11:
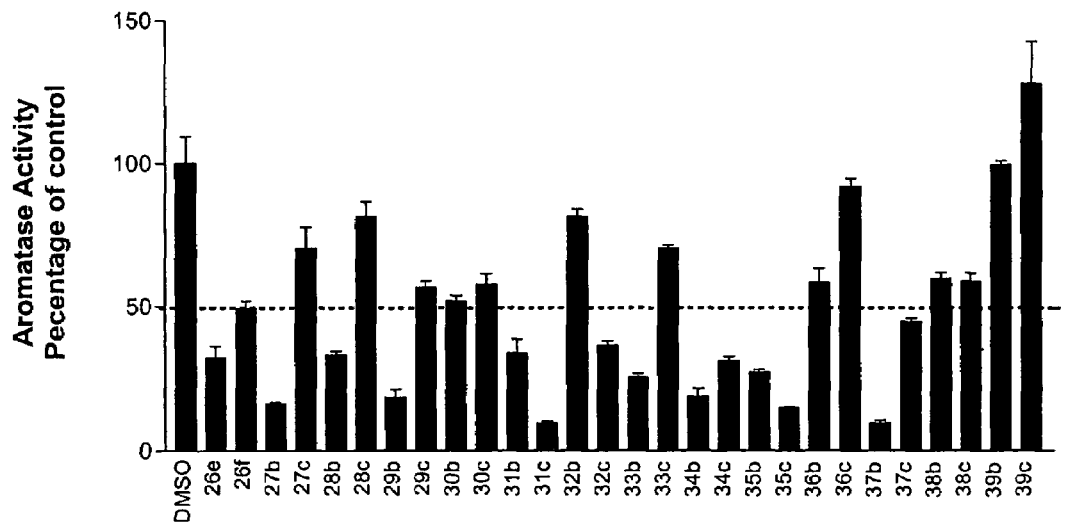
FIG. 11 shows aromatase activity in JAR cells treated with novel sulfonanilide. JAR cells were treated with indicated compounds at 15 µM, and aromatase activity was measured as described in the experimental section. The results were normalized against a control treatment with vehicle, and the value of 100% is equal to 4.0 pmol/hr/$10^6$ cells. Each data bar represents the mean results of three independent determinations.
Figure 12:
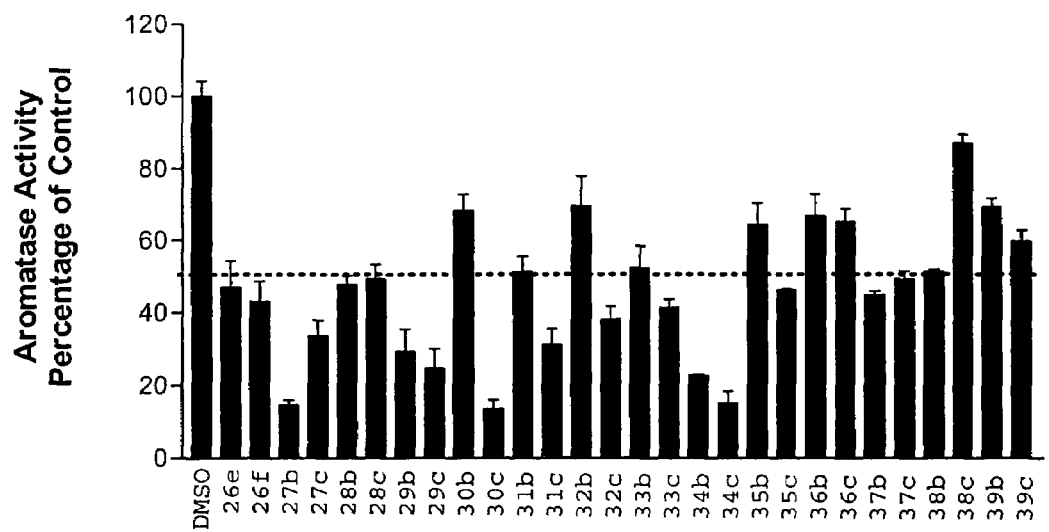
FIG. 12 shows the aromatase activity in SK-BR-3 cells treated with novel sulfonanilide. SK-BR-3 cells were treated with indicated compounds at 2.5 µM and aromatase activity was measured as described in the experimental section. The results were normalized against a control treatment with vehicle, and the value of 100% is equal to 0.03 pmol/hr/$10^6$ cells. Each data bar represents the mean results of three independent determinations.

The ability of the synthesized compounds to suppress aromatase activity was performed in JAR cells (FIG. 11). Unexpectedly, most of the compounds tested exhibited aromatase suppression activity at 15 µM concentration. The results indicate that the compounds may be involved in multiple pathways to decrease aromatase activity. Most of the compounds significantly decrease aromatase activity in SK-BR-3 cells as well at 2.5 µM (FIG. 12). Among all the compounds tested, only the ones that do not affect aromatase activity in JAR cells but decrease aromatase activity in SK-BR-3 breast cancer cells might be selective aromatase expression regulators. In FIG. 11, compounds 26f, 27c, 28c, 29c, 30b, 30c, 32b, 33c, 36b, 36c, 38b, 38c, 39b, 39c at 15 µM decrease aromatase activity less than 50% in JAR cells. In FIG. 12, compounds 26e, 26f, 27b, 27c, 28b, 28c, 29b, 29c, 30c, 31c, 32c, 33c, 34b, 34c, 35c, 37b, 37c, 38b decrease aromatase activity greater than 50% at 2.5 µM in SK-BR-3 cells. Compounds 26f, 27c, 28c, 29c, 30c, 33c may be potential selective aromatase expression regulators because they do not decrease aromatase activity very effectively in JAR cells at 15 µM but significantly suppress aromatase activity in SK-BR-3 breast cancer cells at 2.5 µM.

Figure 13:
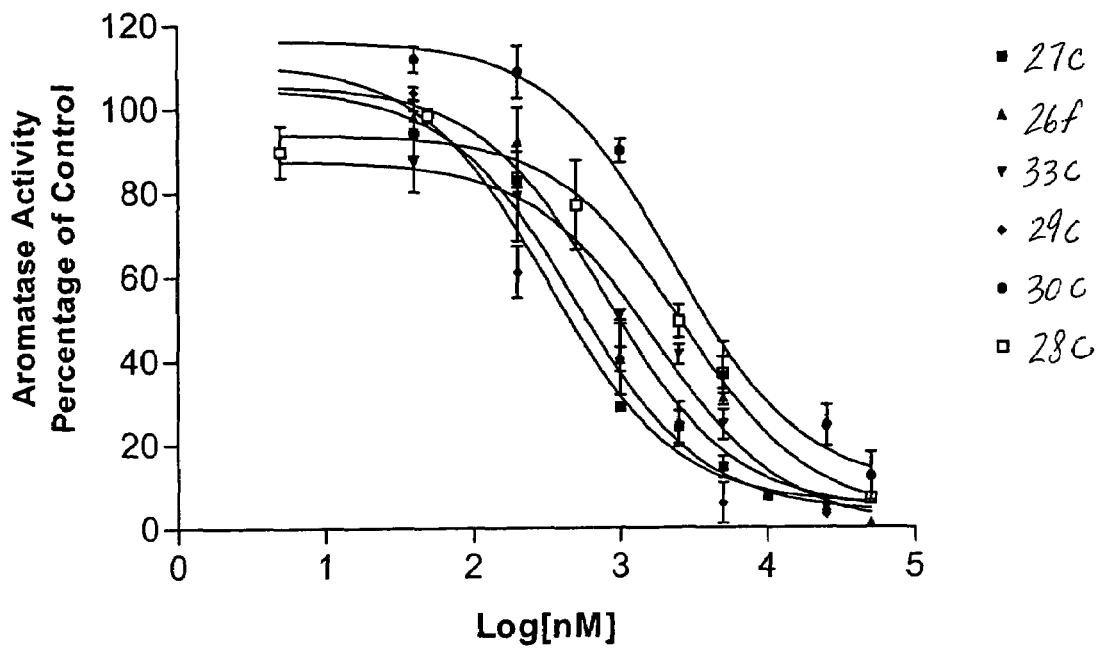
FIG. 13 shows the dose-response suppression of aromatase activity in SK-BR-3 cells by novel sulfonanilide. SK-BR-3 cells were treated with 27c (■), 26f (▲), 33c (▼), 29c (♦), 30c (●) and 28c (□) and aromatase activity was measured as described in the experimental section. The results were normalized against a control treatment with vehicle, with the value of 100% is equal to 0.03 pmol/hr/$10^6$ cells. Each data point represents the mean results of three independent determinations, and the data were statistically analyzed by a non-linear regression analysis method.
Figure 14:
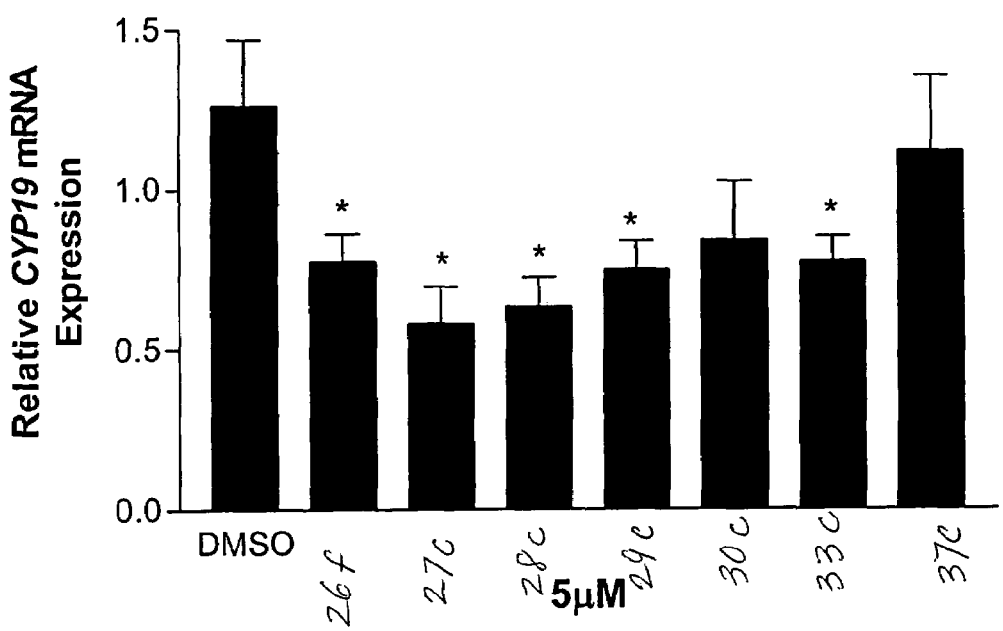
FIG. 14 shows real-time RT-PCR analysis of CYP19 mRNA expression in SK-BR-3 cells treated by novel sulfonanilide. Cells were treated for 24 h with the indicated agents at 5 µM, and total RNA was isolated. Results are expressed as means of CYP19 (normalized to 18S rRNA) ±SEM., *P<0.05 vs. control by unpaired t test (n=9).

To further investigate the six compounds, dose-response studies on aromatase activity were performed in SK-BR-3 cells. All six compounds exhibited dose-response of suppression aromatase activity (FIG. 13) and the corresponding $IC_{50}$ values are listed in Table 2. The $IC_{50}$ of nimesulide is listed as well. The results of the cellular aromatase assay exhibited that extending one carbon at 2-position of nimesulide results in significant increase in suppression of aromatase in breast cancer cells compared with nimesulide. Compound 29c, which is the most bulky compound, showed the best $IC_{50}$ value with an eighty fold increase. Furthermore, real time PCR demonstrated that compounds 26f, 27c, 28c, 29c, 33c at 5 µM significantly decreased CYP19 gene expression in SK-BR-3 cells (FIG. 14). This suggests that the suppression of aromatase enzyme activity occurs at the transcriptional level. Compound 38b was chosen as a negative control because it inhibited aromatase activity in both JAR cells and SK-BR-3 cells. Real time RT-PCR assay of CYP19 demonstrated that compound 37b might only decrease aromatase enzyme, but not affect the CYP19 gene expression. This result suggests that 37b decreases aromatase activity through a posttranscriptional mechanism. In addition, some researchers found that aromatase was also regulated via phosphorylation processes. Possible mechanisms by which an agent only decreases aromatase enzyme activity without suppression of its gene expression are direct enzyme inhibition, increased enzyme degradation, or alterations in posttranslational modifications.

TABLE 2

Suppression of aromatase activity in SK-BR-3 breast cancer cells

| Compd | Chemical Description | $IC_{50}$ (µM)[a] |
|---|---|---|
| Nimesulide | N-(2-phenoxy-4-nitrophenyl)-methanesulfonamide | 27.0 ± 4.70[b] |
| 26f | N-methyl-N-(2-benzyloxy-4-nitrophenyl) methanesulfonamide | 0.81 ± 0.29 |
| 27c | N-methyl-N-[2-(4'-nitro benzyloxy)-4-nitrophenyl] methanesulfonamide | 0.49 ± 0.14 |
| 28c | N-methyl-N-[2-(β-naphthylmethoxy) 4-nitrophenyl] methanesulfonamide | 2.68 ± 0.91 |
| 29c | N-methyl-N-[2-(2'-phenyl benzyloxy)-4-nitrophenyl] methanesulfonamide | 0.33 ± 0.15 |
| 30c | N-methyl-N-[2-(4'-methyl benzyloxy)-4-nitrophenyl] methanesulfonamide | 2.33 ± 0.66 |

TABLE 2-continued

Suppression of aromatase activity in SK-BR-3 breast cancer cells

| Compd | Chemical Description | $IC_{50}$ (µM)[a] |
|---|---|---|
| 33c | N-methyl-N-[2-(4'-fluoro benzyloxy)-4-nitrophenyl] methanesulfonamide | 1.78 ± 0.63 |

Figure 15:
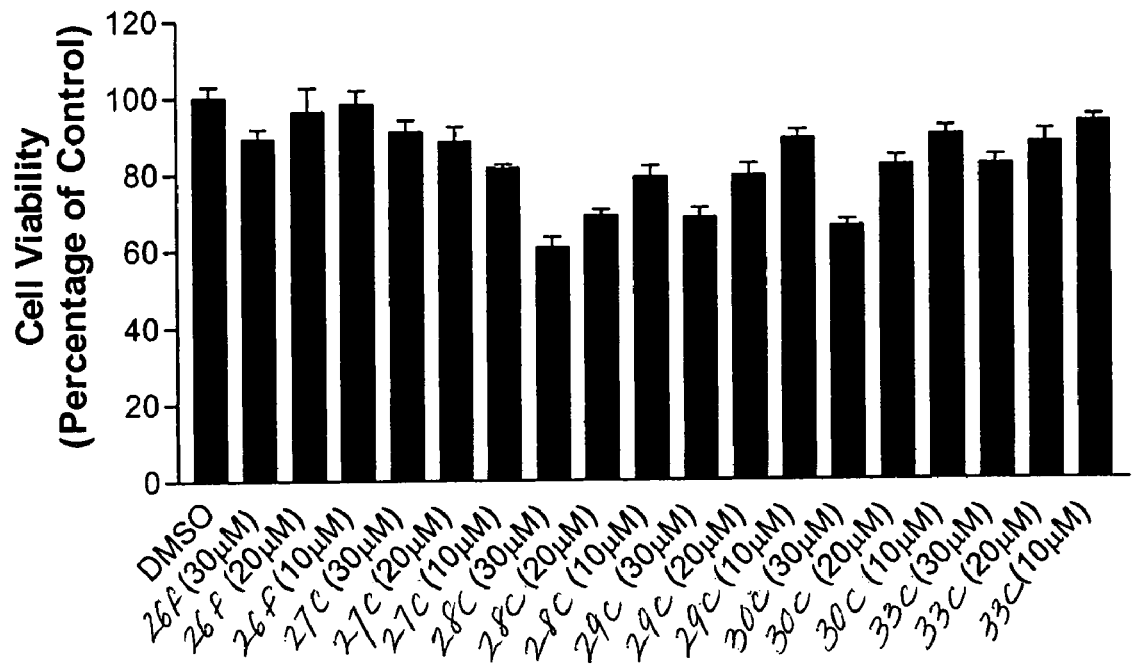
FIG. 15 shows cell cytotoxicity in SK-BR-3 cells treated with novel sulfonanilide. SK-BR-3 cells were treated with indicated compounds at different concentrations and cell viability was measured by MTT assay as described in the experimental section.
Figure 16:
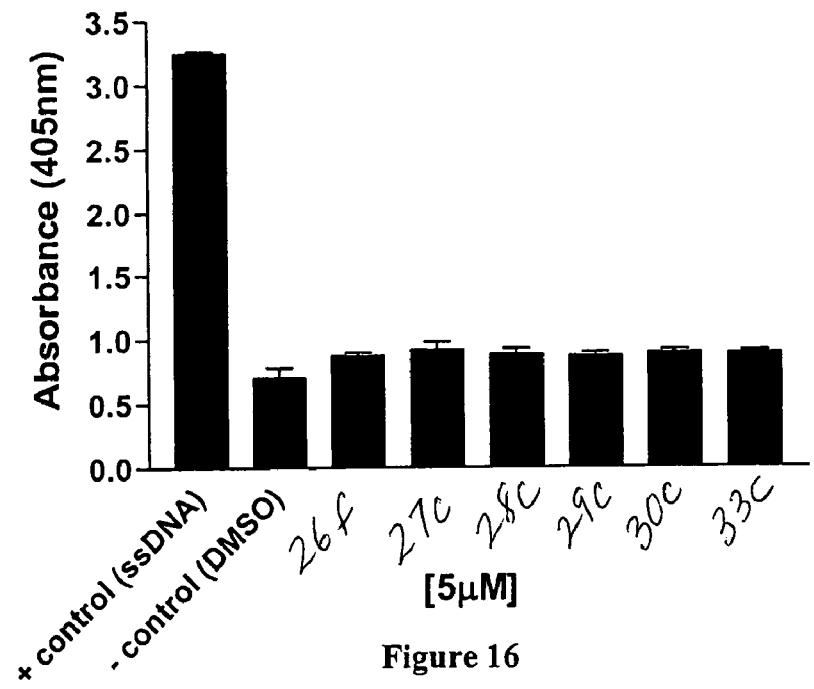
FIG. 16 shows cell apoptosis in SK-BR-3 cells treated with novel sulfonanilide. SK-BR-3 cells were treated with indicated compounds at different concentrations and apoptotic cells was measured as described in the experimental section.

Fortunately, all six compounds, 26f, 27c, 28c, 29c, 30c, and 33c, did not cause significant cell cytotoxicity in SK-BR-3 breast cancer cells at higher concentrations (10 µM) than the effective dose for suppression of aromatase expression (FIG. 15). However, some of them induce some cytotoxicity at higher concentrations (30 µM). The compounds do not produce apoptotic effects in SK-BR-3 cells at 5 µM, which is effective dose for suppressing aromatase expression (FIG. 16). These two results show that, at low micromolar concentrations, the six compounds did not cause any cytotoxicity and apoptotic effects.

In summary, the biological results indicated that several agents selectively decreased aromatase activity and enzyme gene expression at low micromolar concentrations in SK-BR-3 breast cancer cells. These compounds were ten- to eighty-fold more active than nimesulide and did not affect the aromatase activity in choriocarcinoma placental JAR cells. Furthermore, this suppression of aromatase activity occurs at the transcriptional level.

All documents referenced herein are incorporated by reference.

Although this invention has been described with respect to specific embodiments, the details of these embodiments are not to be construed as limitations.

The invention claimed is:

1. A compound of formula I:

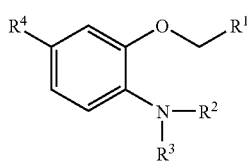

wherein $R^1$ is selected from the group consisting of cycloalkyl, haloalkyl, aryl, substituted aryl, haloaryl, alkoxy, alkylaryl, and arylalkyl, $R^2$ is selected from the group consisting of alkyl, aryl, alkylaryl, arylalkyl, and cycloalkyl;

$R^3$, with the base nitrogen, forms a sulfonamide;

$R^4$ is selected from the group consisting of nitro, amine, amide, and benzamide;

or a pharmaceutically acceptable salt thereof.

2. The compound of claim 1 wherein $R^1$ is selected from the group consisting of cyclopentyl, cyclohexyl, methylcyclohexyl, benzyl, nitrobenzyl, alkylbenzyl, dialkylbenzyl, alkoxybenzyl, halobenzyl, phenylalkyl, phenylbenzyl, phenylbenzyloxy, naphthyl, and naphthylmethyl; or a pharmaceutically acceptable salt thereof.

3. The compound of claim 2 wherein $R^1$ is selected from the group consisting of cyclopentyl, cyclohexyl, methylcyclohexyl, ethylcyclohexyl, 1-methoxypropyl, and 1-ethoxypropyl; or a pharmaceutically acceptable salt thereof.

4. The compound of claim 2 wherein $R^1$ is selected from the group consisting of nitrobenzyl, phenylbenzyl, naphthyl, naphthylmethyl, methoxybenzyl, isopropylbenzyl, fluorobenzyl, chlorobenzyl, bromobenzyl, dimethylbenzyl, and phenylethyl; or a pharmaceutically acceptable salt thereof.

5. The compound of claim 4 wherein $R^1$ is selected from 4-nitrobenzyl, 2-phenylbenzyl, naphthyl, α-naphthylmethyl, β-naphthylmethyl, 4-methoxybenzyl, 4-isopropylbenzyl, 4-fluorobenzyl, 4-chlorobenzyl, 4-bromobenzyl, 3,6-dimethylbenzyl, and phenylethyl; or a pharmaceutically acceptable salt thereof.

6. The compound of claim 5 wherein $R^1$ is selected from the group consisting of phenylbenzyl and methylnaphthyl; or a pharmaceutically acceptable salt thereof.

7. The compound of claim 1 wherein $R^1$ is substituted aryl, and wherein the aryl substituent is selected from the group consisting of alkyl, aryl, halo, alkylaryl, arylalkyl, and combinations thereof or a pharmaceutically acceptable salt thereof.

8. The compound of claim 1 wherein $R^2$ is selected from $C_1$ to $C_{10}$ alkyl, wherein the alkyl may be straight chain, branched, or cyclic, or a combination thereof or a pharmaceutically acceptable salt thereof.

9. The compound of claim 8 wherein $R^2$ is selected from the group consisting of methyl, ethyl, n-propyl, isopropyl, pentyl, hexyl or cyclohexyl; or a pharmaceutically acceptable salt thereof.

10. The compound of claim 9 wherein $R^2$ is methyl; or a pharmaceutically acceptable salt thereof.

11. The compound of claim 1 wherein $R^2$ is selected from the group consisting of alkylaryl, benzyl, alkoxybenzyl, alkylbenzyl, halobenzyl, biphenyl, and naphthyl; or a pharmaceutically acceptable salt thereof.

12. The compound of claim 11 wherein $R^2$ is selected from the group consisting of benzyl, methoxybenzyl, methylbenzyl, fluorobenzyl, chlorobenzyl, bromobenzyl, isopropylbenzyl, dimethylbenzyl, phenylbenzyl, and naphthyl; or a pharmaceutically acceptable salt thereof.

13. The compound of claim 12 wherein $R^2$ is selected from the group consisting of benzyl, 4-methoxybenzyl, 4-methylbenzyl, 4-fluorobenzyl, 4-chlorobenzyl, 4-bromobenzyl, 4-isopropylbenzyl, 2,5-dimethylbenzyl, 4-phenylbenzyl, and 2-naphthyl; or a pharmaceutically acceptable salt thereof.

14. The compound of claim 1 wherein $R^4$ is selected from the group consisting of benzyl, cyanobenzamide, halobenzamide, dihalobenzamide, nitrobenzamide, naphthylamide; or a pharmaceutically acceptable salt thereof.

15. The compound of claim 14 wherein $R^4$ is selected from the group consisting of 4-cyanobenzamide, 3,4-dichlorobenzamide, 3-nitrobenzamide, and 2-naphthylamide; or a pharmaceutically acceptable salt thereof.

16. The compound of claim 1 wherein $R^4$ is an alkylamide; or a pharmaceutically acceptable salt thereof.

17. The compound of claim 16 wherein $R^4$ is cyclohexylamide; or a pharmaceutically acceptable salt thereof.

18. A method for suppressing aromatase activity expression in cancer cells comprising the step of administering a pharmaceutically effective amount of an aromatase inhibitor of structure I:

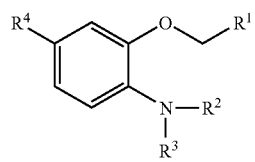

wherein $R^1$ is selected from the group consisting of cycloalkyl, haloalkyl, aryl, substituted aryl, haloaryl, alkoxy, alkylaryl, and arylalkyl, $R^2$ is selected from the group consisting of alkyl, aryl, alkylaryl, arylalkyl, and cycloalkyl;

$R^3$, with the base nitrogen, forms a sulfonamide;

$R^4$ is selected from the group consisting of nitro, amine, amide, and benzamide;

or a pharmaceutically acceptable salt thereof to a subject in need of such treatment.

19. The method of claim 18 wherein the cancer cells are breast cancer cells.

* * * * *

SEQUENCE LISTING

<160> NUMBER OF SEQ ID NOS: 6

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtctctttg ttcttcatgc tatttctc                                    28

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcaccaataa cagtctggat ttcc                                        24

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic

```
                        -continued probe

<400> SEQUENCE: 3
tgcaaagcac cctaatgttg aagaggcaat                              30

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagttcatac agcggaacac tg                                      22

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tttgctggag aacagggctg                                         20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
tgctggcacc agacttgccc tc                                      22
```